(12) United States Patent
Gonenc et al.

(10) Patent No.: US 10,369,045 B2
(45) Date of Patent: Aug. 6, 2019

(54) MICROMANIPULATION SYSTEMS AND METHODS

(71) Applicants: The Johns Hopkins University, Baltimore, MD (US); CARNEGIE MELLON UNIVERSITY, Pittsburgh, PA (US)

(72) Inventors: Berk Gonenc, Baltimore, MD (US); Iulian Iordachita, Lutherville-Timonium, MD (US); Russell H. Taylor, Severna Park, MD (US); Cameron Riviere, Pittsburgh, PA (US); Peter Gehlbach, Monkton, MD (US); James Handa, Baltimore, MD (US)

(73) Assignees: The Johns Hopkins University, Baltimore, MD (US); Carnegie Mellon University, Pittsburgh, PA (US)

( * ) Notice: Subject to any disclaimer, the term of this patent is extended or adjusted under 35 U.S.C. 154(b) by 196 days.

(21) Appl. No.: 14/810,277

(22) Filed: Jul. 27, 2015

(65) Prior Publication Data
US 2016/0030240 A1 Feb. 4, 2016

Related U.S. Application Data

(60) Provisional application No. 62/030,465, filed on Jul. 29, 2014.

(51) Int. Cl.
*A61F 9/007* (2006.01)
*G01L 5/22* (2006.01)
(Continued)

(52) U.S. Cl.
CPC .......... *A61F 9/00736* (2013.01); *A61B 5/065* (2013.01); *A61B 17/2909* (2013.01);
(Continued)

(58) Field of Classification Search
CPC .. A61F 9/00736; A61F 9/008; A61F 9/00745; G01L 5/226; A61B 34/72;
(Continued)

(56) References Cited

U.S. PATENT DOCUMENTS 6,238,384 B1 5/2001 Peer
6,402,734 B1 6/2002 Weiss
(Continued)

FOREIGN PATENT DOCUMENTS

WO WO-2012/018821 A2 2/2012
WO WO 2012047626 A1 * 4/2012 ............. A61B 42/10

OTHER PUBLICATIONS

Almony et al., "Techniques, rationale, and outcomes of internal limiting membrane peeling," Retina (Philadelphia, Pa.), vol. 32, No. 5, pp. 877-891, May 2012.
(Continued)

*Primary Examiner* — Kami A Bosworth
*Assistant Examiner* — Alexandra LaLonde
(74) *Attorney, Agent, or Firm* — Venable LLP; Henry J. Daley; Laura G. Remus

(57) ABSTRACT

A micromanipulation system includes a micromanipulator that includes a handpiece, and a micromanipulation tool that includes a tool shaft and is operatively connected to the handpiece. The micromanipulator further includes an actuator assembly connected to the micromanipulation tool to provide manual control of the micromanipulation tool, and a force sensing system comprising a force sensor attached to the tool shaft. The force sensing system is configured to provide an output signal that indicates a force imposed on the tool shaft. The micromanipulation system also includes a processor that is in communication with the force sensing system, and is configured to receive the output signal and compensate for forces due to actuation of the micromanipulation tool to determine a force due to interaction of the micromanipulation tool with a region of interest. The processor outputs an indication of at least one of a magnitude and a direction of the determined force.

19 Claims, 43 Drawing Sheets

(51) Int. Cl.
| A61B 17/29 | (2006.01) |
| A61B 5/06 | (2006.01) |
| A61B 34/00 | (2016.01) |
| G01L 25/00 | (2006.01) |
| G01L 1/24 | (2006.01) |
| A61B 5/00 | (2006.01) |
| A61B 17/30 | (2006.01) |
| A61B 90/00 | (2016.01) |

(52) U.S. Cl.
CPC .............. *A61B 34/70* (2016.02); *A61B 34/72* (2016.02); *A61B 34/75* (2016.02); *G01L 1/246* (2013.01); *G01L 5/226* (2013.01); *G01L 25/00* (2013.01); *A61B 5/489* (2013.01); *A61B 5/6848* (2013.01); *A61B 2017/2902* (2013.01); *A61B 2017/2912* (2013.01); *A61B 2017/305* (2013.01); *A61B 2090/064* (2016.02)

(58) Field of Classification Search
CPC ......... A61B 34/75; A61B 34/77; A61B 34/76; A61B 34/70; A61B 5/065; A61B 2090/064; A61M 2205/332
See application file for complete search history.

(56) References Cited

U.S. PATENT DOCUMENTS

| 6,702,761 | B1 | | 3/2004 | Damadian et al. | |
| 2001/0012932 | A1* | | 8/2001 | Peer ..................... | A61B 17/062 606/1 |
| 2010/0152586 | A1* | | 6/2010 | Grant ..................... | A61B 5/489 600/454 |
| 2011/0301500 | A1* | | 12/2011 | Maguire ................ | A61B 5/489 600/583 |
| 2012/0209303 | A1* | | 8/2012 | Frankhouser ........ | A61B 10/025 606/169 |
| 2013/0012930 | A1* | | 1/2013 | Ruiz Morales ........ | B25J 13/085 606/1 |
| 2014/0303660 | A1* | | 10/2014 | Boyden ................. | A61B 17/32 606/170 |

OTHER PUBLICATIONS

Balicki et al., "Micro-force Sensing in Robot Assisted Membrane Peeling for Vitreoretinal Surgery," *Med Image Comput Comput Assist Interv.*, 2010, pp. 303-310.
Becker et al., "Vision-based control of a handheld surgical micromanipulator with virtual fixtures," *IEEE Trans. Robotics*, vol. 29, No. 3, pp. 674-683, Jun. 2013.
Becker et al., "Towards vision-based control of a handheld micromanipulator for retinal cannulation in an eyeball phantom," in *Proc. 4th IEEE RAS EMBS Int. Conf. Biomed. Robot. Biomechatron.*, Rome, 2012, pp. 44-49.
Chang et al., "Design of a novel tremor suppression device using a linear delta manipulator for micromanipulation," in *Proc. IEEE Int. Conf. on Intelligent Robots and Systems (IROS '13)*, 2013, pp. 413-418.
Charles, "Techniques and tools for dissection of epiretinal membranes," *Graefe's Archive for Clinical and Experimental Ophthalmology*, vol. 241:5, pp. 347-352, May 2003.
Cutler et al., "Auditory force feedback substitution improves surgical precision during simulated ophthalmic surgery," *Investigative Ophthalmology & Visual Science*, vol. 54, pp. 1316-1324 2013.
Das et al., "Evaluation of a telerobotic system to assist surgeons in microsurgery," *Comput Aided Surg*, vol. 4:1, pp. 15-25, 1999.
Elble et al., "Mechanistic Components of Normal Hand Tremor," *Electroencephalography and Clinical Neurophysiology*, vol. 44:1, pp. 72-82, Jan. 1978.
Ergeneman et al., "Characterization of puncture forces for retinal vein cannulation," *J. Med. Dev.*, vol. 5, No. 4, pp. 044504, Dec. 2011.
Fleming et al., "Cooperative robot assistant for retinal microsurgery," Med. Image Comput. Comput. Assist. Interv., vol. 5242, 2008, pp. 543-550.
Gijbels et al., "Design and realisation of a novel robotic manipulator for retinal surgery," in Proc. IEEE Int. Conf. on Intelligent Robots and Systems, Tokyo, 2013, pp. 3598-3603.
Glucksberg et al., "In vivo micropuncture of retinal vessels," Graefe's Archive for Clinical and Experimental Ophthalmology, vol. 231, No. 7, pp. 405-407, Jul. 1993.
Gonenc et al., "Towards Robot-Assisted Vitreoretinal Surgery: Force-Sensing Micro-Forceps Integrated with a Handheld Micromanipulator," in Proc. IEEE Int. Conf. on Robotics and Automation (ICRA'14), 2014, pp. 1399-1404.
Gonenc et al., "A Comparative Study for Robot Assisted Vitreoretinal Surgery: Micron vs. the Steady-Hand Robot," in Proc. IEEE Int. Conf. on Robotics and Automation (ICRA '13), 2013, pp. 4832-4837.
Gonenc et al., "Design of 3-DOF Force Sensing Micro-Forceps for Robot Assisted Vitreoretinal Surgery," in *Proc. International Conference of the IEEE EMBS (EMBC '13)*, 2013, pp. 5686-5689.
Gonenc et al., "Preliminary Evaluation of a Micro-Force Sensing Handheld Robot for Vitreoretinal Surgery," in *Proc. IEEE Int. Conf. Intelligent Robots and Systems (IROS '12)*, 2012, pp. 4125-4130.
Gonenc et al., "Force-Sensing Microneedle for Assisted Retinal Vein Cannulation," in Proc. IEEE SENSORS 2014, 2014, pp. 698-701.
Gonenc et al., "Motorized Force-Sensing Micro-Forceps with Tremor Cancelling and Controlled Micro-Vibrations for Easier Membrane Peeling," in Proc. IEEE RAS EMBS Int. Conf. Biomed. Robot. Biomechatron. (BioRob'14), 2014, pp. 244-251.
Gupta et al., "Surgical forces and tactile perception during retinal microsurgery," in Proc. MICCAI'99, 1999, pp. 1218-1225.
He et al., "A sub-milimetric 3-dof force sensing instrument with integrated fiber Bragg grating for retinal microsurgery," IEEE Trans. Biomed. Eng., vol. 61:2, pp. 522-534, Feb. 2014.
He et al., "Force sensing micro-forceps with integrated fiber bragg grating for vitreoretinal surgery," in Proc. of SPIE, vol. 8218, pp. 82180W 1-7, Feb. 2012.
He et al., "A multi-function force sensing instrument for variable admittance robot control in retinal microsurgery," in Proc. Robotics and Automation (ICRA'14), 2014, pp. 1411,1418.
Hunter et al., "Opthalmic microsurgical robot and associated virtual environment," Comput Biol Med, vol. 25:2, pp. 173-182, Mar. 1995.
Iordachita et al., "A sub-millimetric, 0.25 mn resolution fully integrated fiber-optic force-sensing tool for retinal microsurgery," Int J Comput Assist Radiol Surg., vol. 4, No. 4, pp. 383-390, Jun. 2009.
Jensen et al., "Toward robot-assisted vascular in the retina," Graefe's Arch Clin Exp Ophthalmol, vol. 235, No. 11, pp. 696-701, Nov. 1997.
Kadonosono et al., "An experimental study of retinal endovascular surgery wih a fabricated needle," Invest. Opthalmol. Vis. Sci., vol. 52, No. 8, pp. 5790-5793, Jul. 2011.
Kadonosono et al., "Endovascular cannulation with a microneedle for central retinal vein occlusion," JAMA Ophthalmol, vol. 131, No. 6, pp. 783-786, Jun. 2013.
Kuru et al., "Force Sensing Micro-Forceps for Robot Assisted Retinal Surgery," in Proc. International Conference of the IEEE EMBS (EMBC '12), 2012, pp. 1401-1404.
Latt et al., "A compact handheld active physiological tremor compensation instrument," in Proc. IEEE/Amer.Soc. Mech. Eng. Int. Conf. Adv. Intell. Mechatronics, 2009, pp. 711-716.
Latt et al., "Compact sensing design of a hand-held active tremor compensation instrument for better ergonomics," in Proc. 2nd IEEE RAS EMBS Int Conf Biomed Robot Biomechatron (BioRob), 2008, pp. 276-281.
Leng et al., "The chick chorioallantoic membrane as a model tissue for surgical retinal research and simulation," Retina, vol. 24, No. 3, pp. 427-434, Jun. 2004.

(56) References Cited

OTHER PUBLICATIONS

MacLachlan et al., "Micron: an actively stabilized handheld tool for microsurgery," *IEEE Trans Robot*, vol. 28:1, pp. 195-212, Feb. 2012.
MacLachlan et al., "High-speed microscale optical tracking using digital frequency-domain multiplexing," *IEEE Trans. Instrumentation and Measurement*, vol. 58, No. 9, pp. 1991-2001, 2009.
Mulgaonkar et al., "A prototype surgical manipulator for robotic intraocular micro surgery," *Stud Health Technol Inform*, vol. 142, pp. 215-217, 2009.
Nakata et al., "Sub-retinal hemorrhage during internal limiting membrane peeling for a macular hole," *Graefes Arch Clin Exp Ophthalmol*, vol. 241, pp. 582-584, Jul. 2003.
Payne et al., "An ungrounded hand-held surgical device incorporating active constraints with force-feedback," in *Proc. IEEE Int. Conf. on Intelligent Robots and Systems (IROS '13)*, 2013, pp. 2559-2565.
Rogers et al., "The prevalence of retinal vein occlusion: Pooled data from population studies from the United States, Europe, Asia, and Australia," *Ophthalmology*, vol. 117, pp. 313-19.e1, 2010.
Saito et al., "Detection of needle puncture to blood vessel using puncture force measurement," *Med. Biol. Eng. Comput.*, vol. 43, No. 2, pp. 240-244, Mar. 2005.
Saxena et al., "An active handheld device for compensation of physiological tremor using an ionic polymer metallic composite actuator," in *Proc. IEEE Int. Conf. on Intelligent Robots and Systems (IROS '13)*, 2013, pp. 4275-4280.
Schenker et al., "Development of a telemanipulator for dexterity enhanced microsurgery," in *Proc. 2nd Int Symp Med Rob Comput Asst Surg*, 1995, pp. 81-88.
Singh et al., "Physiological tremor amplitude during retinal microsurgery," in *Proc. IEEE 28th Annu. Northeast Bioeng. Conf.*, Philadelphia, 2002, pp. 171-172.
Sjaarda et al., "Distribution of iatrogenic retinal breaks in macular hole surgery," *Ophthalmology*, vol. 102:9, pp. 1387-1392, Sep. 1995.
Skovborg et al., "Diameters of the retinal vessels in diabetic and normal subjects," *Diabetes*, vol. 18, No. 5, pp. 292-298, May 1969.
Sun et al., "Development and preliminary data of novel integrated optical micro-force sensing tools for retinal microsurgery," in *Proc. IEEE Int. Conf. on Robotics and Automation (ICRA '09)*, 2009, pp. 1897-1902.
Tanaka et al., "Quantitative assessment of manual and robotic microcannulation for eye surgery using new eye model," *Int J Med Robotics Comput Assist Surg*, Apr. 2014.
Tsilimbaris et al., "Retinal microvascular surgery: A feasibility study," *Invest. Ophthalmol. Vis. Sci.*, vol. 45, No. 6, pp. 1963-1968, Jun. 2004.
Ueta et al., "Robot-assisted vitreoretinal surgery: Development of a prototype and feasibility studies in an animal model," *Ophthalmology*, vol. 116:8, pp. 1538-1543, Aug. 2009.
Uneri et al., "New steady-hand Eye Robot with micro-force sensing for vitreoretinal surgery," in *Proc. 3rd IEEE RAS EMBS Int Conf Biomed Robot Biomechatron (BioRob)*, 2010, pp. 814-819.
Wei et al., "Enabling technology for microvascular stenting in ophthalmic surgery," *Journal of Medical Devices*, vol. 4, No. 1, Mar. 2010.
Weiss et al., "Injection of tissue plasminogen activator into a branch retinal vein in eyes with central vein occlusion," *Ophthalmology*, vol. 108, No. 12, pp. 2249-2257, Jul. 2001.
Yang et al., "Design and Analysis of 6 DOF Handheld Micromanipulator," in *Proc. IEEE Int. Conf. on Robotics and Automation (ICRA '12)*, 2012, pp. 1946-1951.
Zivanovic et al., "A robotic system for blood sampling," *IEEE Trans. Inf. Technol. Biomed.*, vol. 4:1, pp. 8-14, Mar. 2000.

\* cited by examiner

| | Experiments | Number of Trials | Peeling Force [mN] | | Peeling Speed [mm/s] | |
|---|---|---|---|---|---|---|
| | | | Mean | Std. Dev. | Mean | Std. Dev. |
| Bandages | Freehand | 15 | 6.8584 | 0.3676 | 0.1392 | 0.0216 |
| | Tremor Cancellation | 15 | 6.7762 | 0.2894 | 0.1459 | 0.0229 |
| | Tremor Cancellation + 10Hz Vibrations | 15 | 7.0480 | 0.3469 | 0.1789 | 0.0237 |
| | Tremor Cancellation + 30Hz Vibrations | 15 | 6.9440 | 0.3221 | 0.2232 | 0.0472 |
| | Tremor Cancellation + 50Hz Vibrations | 15 | 6.9217 | 0.4403 | 0.2809 | 0.0580 |
| Eggs | Freehand | 5 | 7.7113 | 0.6999 | 0.0868 | 0.0190 |
| | Tremor Cancellation | 5 | 7.3107 | 1.2647 | 0.1005 | 0.0288 |
| | Tremor Cancellation + 10Hz Vibrations | 5 | 7.2937 | 0.9752 | 0.1416 | 0.0649 |
| | Tremor Cancellation + 30Hz Vibrations | 5 | 6.9590 | 1.5154 | 0.1850 | 0.0315 |
| | Tremor Cancellation + 50Hz Vibrations | 5 | 6.3405 | 1.3542 | 0.2948 | 0.0609 |

FIG. 21

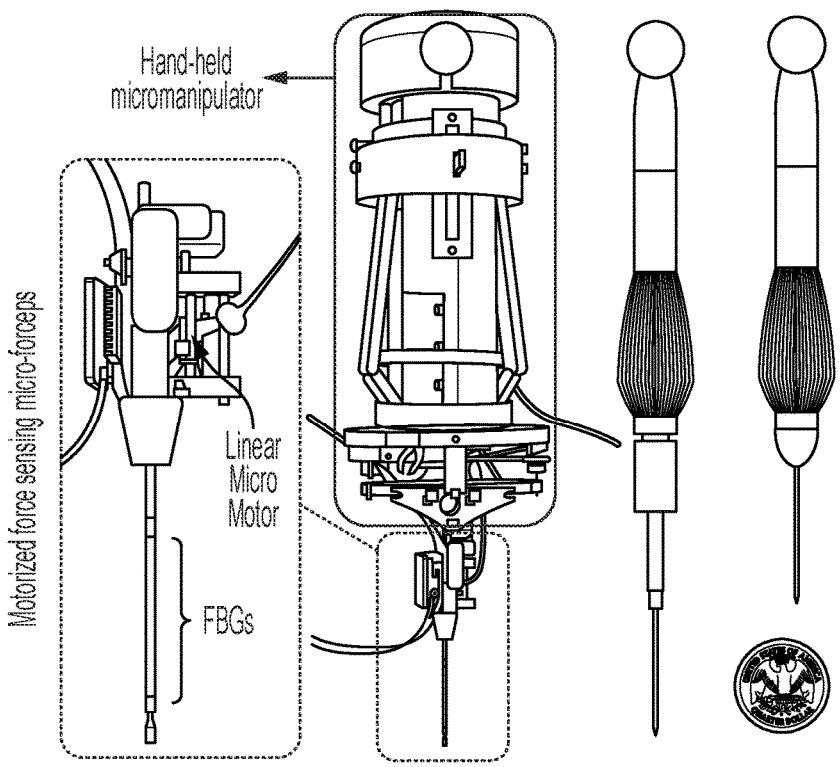

FIG. 22

TABLE 1  MEAN AND STANDARD DEVIATION OF THE MEASURED AVERAGE AND PEAK PEELING FORCE FOR EACH MICRO-VIBRATION SETTING

| NUMBER OF TRIALS | AMPLITUDE | PEELING SPEED = 0.15 mm/s | | | | PEELING SPEED = 0.30 mm/s | | | |
|---|---|---|---|---|---|---|---|---|---|
| | | $f = 0$ Hz | $f = 10$ Hz | $f = 30$ Hz | $f = 50$ Hz | $f = 0$ Hz | $f = 10$ Hz | $f = 30$ Hz | $f = 50$ Hz |
| BANDAGES | | | | | | | | | |
| 15 | 50μm | 5.02±0.19 | 4.98±0.17 | 4.96±0.09 | 4.96±0.10 | | 7.96±0.40 | 8.01±0.44 | 7.86±0.56 |
| 15 | 100mm | | 4.90±0.09 | 4.80±0.09 | 4.84±0.06 | 8.28±0.44 | 8.17±0.44 | 7.88±0.35 | 7.53±0.48 |
| 15 | 150mm | | 4.81±0.07 | 4.64±0.08 | 4.76±0.10 | | 7.80±0.55 | 7.19±0.45 | 7.42±0.47 |
| 15 | 50mm | 6.32±0.28 | 6.07±0.15 | 6.13±0.21 | 6.25±0.25 | | 10.57±1.46 | 11.53±1.69 | 12.04±1.51 |
| 15 | 100mm | | 6.05±0.14 | 7.00±0.26 | 7.91±0.39 | 10.86±1.61 | 11.48±1.62 | 14.30±1.93 | 15.17±2.26 |
| 15 | 150mm | | 6.24±0.30 | 8.12±0.34 | 8.09±0.42 | | 11.49±1.19 | 14.92±2.05 | 17.98±3.06 |
| EGGS | | | | | | | | | |
| 10 | 100mm | 20.24±2.75 | — | 19.14±3.64 | 14.38±5.65 | | | | |
| 10 | 150mm | | — | 12.92±3.39 | 9.02±3.16 | | | | |
| 10 | 100mm | 25.07±3.47 | — | 28.46±5.04 | 27.06±7.72 | | | | |
| 10 | 150mm | | — | 23.92±4.01 | 22.91±4.88 | | | | |

MICRON MODE REGULATION LOGIC

| Condition | Puncture? | Operation Mode |
|---|---|---|
| $\dfrac{d\vec{F}_{needle}}{dt} \cdot \dfrac{d\vec{p}_{needle}}{dt} \leq 0$ | No | Only Tremor Canceling |
| $\dfrac{d\vec{F}_{needle}}{dt} \cdot \dfrac{d\vec{p}_{needle}}{dt} > 0$ | Yes | Active Position Holding |

MICROMANIPULATION SYSTEMS AND METHODS

CROSS REFERENCE TO RELATED APPLICATIONS

This application claims priority to U.S. Provisional Patent Application No. 62/030,465, filed Jul. 29, 2014, which is hereby incorporated herein by reference in its entirety.

This invention was made with government support under EB 000526 and EB 007969 awarded by the National Institutes of Health. The government has certain rights in the invention.

BACKGROUND

1. Field of Invention

The field of the currently claimed embodiments of this invention relates to micromanipulation systems and methods.

2. Discussion of Related Art

Arguably the most technically demanding field of ophthalmic surgery, vitreoretinal practice has faced significant challenges due to present technical and human limitations. A prototypical vitreoretinal task is membrane peeling, where the surgeon delaminates a very thin fibrous membrane adherent to the retinal surface, using either a pick or microforceps. Successful execution of this task requires extensive experience, and is extremely difficult to master due to suboptimal visualization, inconsistent tissue properties, the surgeon's physiological hand tremor, fatigue and involuntary patient motion. During the operation, the instruments need to be moved very slowly, within a range of 0.1-0.5 mm/s, in an extremely delicate environment. Furthermore, application of excessive forces should be avoided. The required forces for delamination routinely lie below the surgeon's sensory threshold. These forces were shown to be below 7.5 mN in porcine cadaver eyes and only 19% of events with this force magnitude can be felt by surgeons [1]. Unintentional motion and application of excessive forces can damage retinal veins [2] and give rise to serious complications such as iatrogenic retinal breaks [3], vitreous hemorrhage, or subretinal hemorrhage [4] leading to potentially irreversible damage and loss of vision.

Retinal vein cannulation (RVC) proposes to treat retinal vein occlusion by direct therapeutic agent delivery methods. During the procedure, clot-dissolving plasminogen activator (t-PA) is injected into the occluded vein [5]. The fine, sharp tips of drawn glass micropipettes enable injection into very small veins. However, their transparency and fragility result in visibility and safety issues. As a more rigid and visible alternative, stainless steel microneedles were proposed [6]. Tests on porcine eyes showed that microneedles are more feasible instruments for microvascular surgery than the glass micropipettes, which was further supported by successful clinical demonstrations on human retinal veins [7]. Despite these improvements, visualizing the tool tip using the operating biomicroscope is still not trivial, and the operation still requires accurate manipulation of extremely delicate tissues inside of the eye, which puts RVC at the limits of human performance.

SUMMARY

According to some embodiments of the present invention, a micromanipulation system includes a micromanipulator that includes a handpiece, and a micromanipulation tool operatively connected to the handpiece. The micromanipulation tool includes a tool shaft. The micromanipulator further includes an actuator assembly connected to the micromanipulation tool to provide manual control of the micromanipulation tool during use, and a force sensing system comprising a force sensor attached to the tool shaft of the micromanipulation tool. The force sensing system is configured to provide an output signal that indicates a force imposed on the tool shaft. In addition to the micromanipulator, the micromanipulation system also includes a processor in communication with the force sensing system. The processor is configured to receive the output signal from the force sensing system and compensate for forces due to actuation of the micromanipulation tool to determine a force due to interaction of the micromanipulation tool with a region of interest. The processor is further configured to output an indication of at least one of a magnitude and a direction of the determined force.

According to some embodiments of the present invention, a method of performing a micromanipulation includes actuating a manual operation of a micromanipulation tool to manipulate an object, and detecting a force on the micromanipulation tool resulting from the manipulation. The method further includes compensating for forces due to actuation of the micromanipulation tool to determine a force due to interaction of the micromanipulation tool with the object, and providing an indication of at least one of a magnitude and a direction of the determined force.

BRIEF DESCRIPTION OF THE DRAWINGS

Further objectives and advantages will become apparent from a consideration of the description, drawings, and examples.

FIG. 21 shows the mean peeling force and speed for peeling bandages and the inner shell membrane of raw chicken eggs;

FIG. 22 shows a motorized force-sensing micro-forceps integrated with a handheld micromanipulator (Micron) according to some embodiments of the invention;

DETAILED DESCRIPTION

Figure 1:
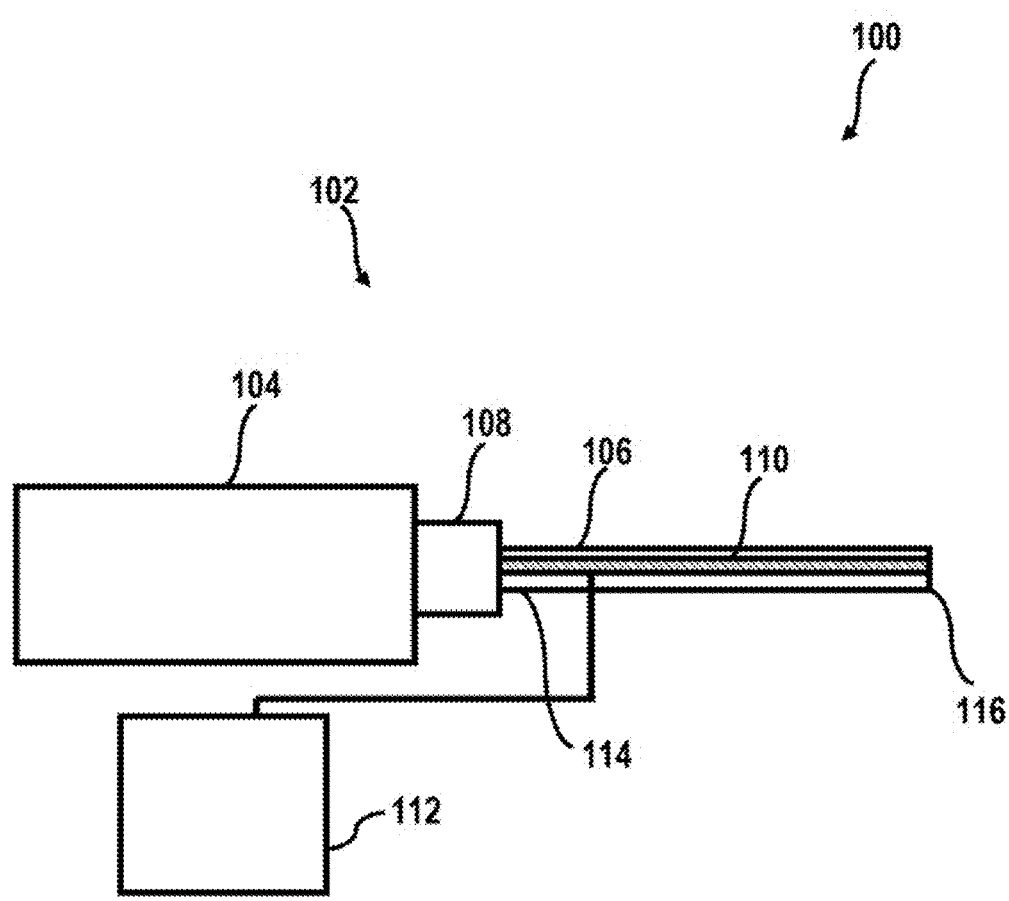
FIG. 1 shows a micromanipulation system according to some embodiments of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Some embodiments of the current invention are directed to a system for providing precise, safe and easier tissue handling capabilities for handheld robotic/manual devices, teleoperated and/or cooperatively controlled robots during microsurgery tasks. Microsurgery routinely requires the manipulation of extremely delicate tissues by various micron scale maneuvers and the application of very small forces. A prototypical procedure in retinal microsurgery is membrane peeling requiring the delamination of a very thin fibrous membrane adherent to the delicate retinal surface. Another demanding application is retinal vein cannulation, which requires injection of clot dissolving agents into very thin and fragile retinal veins. A handheld micromanipulator, a teleoperated system or a cooperatively controlled robot can assist such challenging procedures by providing better stability (i.e., eliminating hand tremor and other unwanted motion). However, in order to make this a viable option, a proper end-effector, for example, a micro-forceps tip for membrane peeling or a micro-needle for vein cannulation, is required to enable such systems.

Some embodiments of the invention provide the design of a novel micromanipulator having an actuator assembly and a force sensing system that can transform into various forms (different micro-forceps forms, or a micro-needle) and can easily be mounted onto a manual handle, or a robotic device. When combined with a robotic device, the attachment forms an integrated assistive system. The resulting micromanipulation system can provide firm tissue grasping (micro-forceps mode) and/or fine injection (micro-needle mode) capabilities while preserving the state-of-the art tremor attenuation functionality of the robotic device. The system can also accurately sense the tool-to-tissue forces, and can provide tool motion assistance to make the procedure easier. The micromanipulator may include a vibrator assembly for pulsating the tool tip at a high frequency to facilitate membrane delamination and/or needle insertion, or a position holding system for holding the tool tip at a fixed location after venous puncture to maintain cannulation for a longer period. The approach can be applied to various handheld micromanipulators as well as the teleoperated and cooperatively controlled devices in the field. Although many of the specific embodiments and working examples provided in this specification are directed to microsurgery, the embodiments of the current invention can apply to other types of micromanipulation.

The terms "micromanipulation" and "micromanipulator" are not meant to indicate that the systems and methods are only applicable to micron-scale procedures. The systems and methods described herein may be used for manipulations on the scale of 100 microns, but are not limited to this scale. The range of motion of the micromanipulation system, as well as the size of the objects with which the micromanipulator interacts, may range, for example, from about 1 μm to about 5 mm. Further, the concepts described herein are not limited to these dimensions, and may be applied to larger and small objects and systems.

Some embodiments of the current invention can provide a micromanipulation tool, actuator assembly, and force sensing system that can be mounted onto any manual handle, handheld micromanipulator, or teleoperated/cooperatively controlled robot to form a complete microsurgery instrument. The actuator assembly can be operated independently from the attached device (handheld micromanipulator or teleoperated/cooperatively controlled robot) via a proper control interface, such as foot pedal, voice control, or a squeeze mechanism clamping on the handle of the attached manual/robotic device. The micromanipulation tool, actuator assembly, and force sensing system can take in different inserts to transform into various surgical instruments (such as a micro-forceps with the firm grasping functionality that the standard manual micro-forceps instruments have, or a micro-needle that enables injection into very small veins). The system can be used to accurately sense the forces applied on the instrument tip and shaft. According to some embodiments, lateral force sensing is provided, i.e. sensing in two degrees-of-freedom (DOF). This can also be extended to three DOF sensing, including axial tool-to-tissue forces as well. According to some embodiments of the invention, the system can sense and distinguish between the forces at the tool tip and forces along the tool shaft, and can effectively cancel out errors due to variations in friction and/or deformation during actuation and ambient temperature.

Some embodiments of the invention provide robotic assistance methods for easier operation and better safety during microsurgery. In addition to hand tremor suppression and auditory force feedback techniques, a method according to an embodiment of the current invention identifies the direction of the exerted force, and pulsates the tool tip at a high frequency along this direction. The force information is provided by the force sensing system while the pulses are generated by the robotic device (a handheld micromanipulator, or a teleoperated/cooperatively controlled robot). This can facilitate delamination of membranes and cannulation of veins, and can significantly lower the exerted forces in retinal microsurgery. The method may be applied in other microsurgical subspecialties as well including neurosurgery, otolaryngology, and vascular surgery. Another distinct assistance method relates to cannulation of veins, and uses measured forces together with tool position information to identify the moment of venous puncture. By continuously monitoring the dot product of the tool tip velocity and the time derivative of the force, the instant when the needle tip enters into the vein lumen can be captured, which is a critical moment in the case of retinal vein cannulation since the needle needs to be fixed at that position throughout the drug delivery period which can take several minutes. After venous puncture detection, the robotic device can be used to compensate for any involuntary operator motion and fix the tool tip position.

Some embodiments can also include software to control the opening/closing action of micro-forceps, or microneedle deployment. Some embodiments can also include software to capture and process force sensor measurements (light wavelength from the optical fibers), convert these measurements into force information, correct the force information so that it is free from the deformation/friction that occurs during tool actuation, and generate an indication of the magnitude and/or direction of the sensed force. The indication may be auditory signals based on the magnitude of the sensed force. The software can also control the micromanipulator/robot to generate micro-vibrations along the direction of the sensed force.

The control protocol and algorithms described herein may be implemented by a processor. The processor can be a dedicated "hard-wired" device, or it can be a programmable device. For example, it can be, but is not limited to, a personal computer, a work station, or any other suitable electronic device for the particular application. In some embodiments, it can be integrated into a unit or it can be attachable, remote, and/or distributed.

FIG. 1 shows a micromanipulation system 100 according to some embodiments of the invention. The micromanipulation system 100 includes a micromanipulator 102. The micromanipulator 102 includes a handpiece 104, and a micromanipulation tool 106 operatively connected to the handpiece 104, the micromanipulation tool 106 comprising a tool shaft. The micromanipulator 102 also includes an actuator assembly 108 connected to the micromanipulation tool 106 to provide manual control of the micromanipulation tool 106 during use. The micromanipulator 102 also includes a force sensing system 110 comprising a force sensor attached to the tool shaft of the micromanipulation tool 106, the force sensing system 110 being configured to provide an output signal that indicates a force imposed on the tool shaft. The micromanipulation system 100 also includes a processor 112 in communication with the force sensing system 110. The processor 112 is configured to receive the output signal from the force sensing system and compensate for forces due to actuation of the micromanipulation tool 106 to determine a force due to interaction of the micromanipulation tool 106 with a region of interest. The processor 112 is further configured to output an indication of at least one of a magnitude and a direction of the determined force.

According to some embodiments of the invention, the tool shaft 106 has a connecting end 114 and a manipulation end 116, and the force sensing system 110 is configured to provide an output signal that indicates a force imposed at the manipulation end 116 of the tool shaft.

According to some embodiments of the invention, the micromanipulation system 100 includes a tool vibrating system comprising a vibrator assembly mechanically coupled to the tool shaft. The tool vibrating system further comprises a vibration controller that is configured to communicate with the processor to receive the indication of at least one of a magnitude and a direction of the determined force and to cause the vibrator assembly to impose a vibration to the tool shaft along the direction of the force imposed on the tool shaft.

According to some embodiments of the invention, the micromanipulator 102 further includes a tremor cancellation system comprising a motor within the handpiece 104, the motor being operatively attached to the micromanipulation tool 106 to provide active cancellation of tremor on the micromanipulator 102 during use independently of vibrations from the tool vibrating system.

According to some embodiments of the invention, the micromanipulation system 100 includes a position detection system configured to detect a position of the micromanipulator 102 and transmit a signal to the processor 112 indicating the detected position.

According to some embodiments of the invention, a method of performing a micromanipulation includes actuating a manual operation of a micromanipulation tool to manipulate an object, detecting a force on the micromanipulation tool resulting from the manipulation, compensating for forces due to actuation of the micromanipulation tool to determine a force due to interaction of the micromanipulation tool with the object, and providing an indication of at least one of a magnitude and a direction of the determined force.

Figure 2:
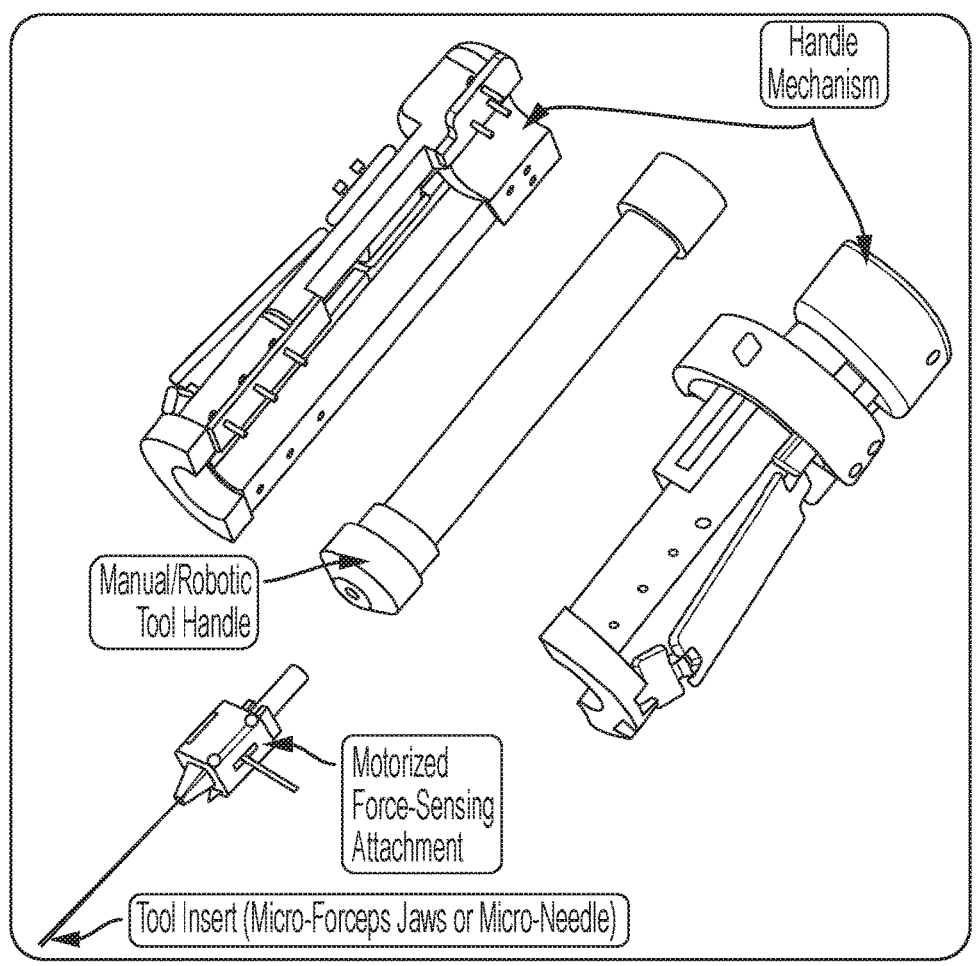
FIG. 2 illustrates how the motorized force-sensing attachment can be independently actuated from the micromanipulator, with the handle mechanism providing easy control of the attachment.
Figure 3:
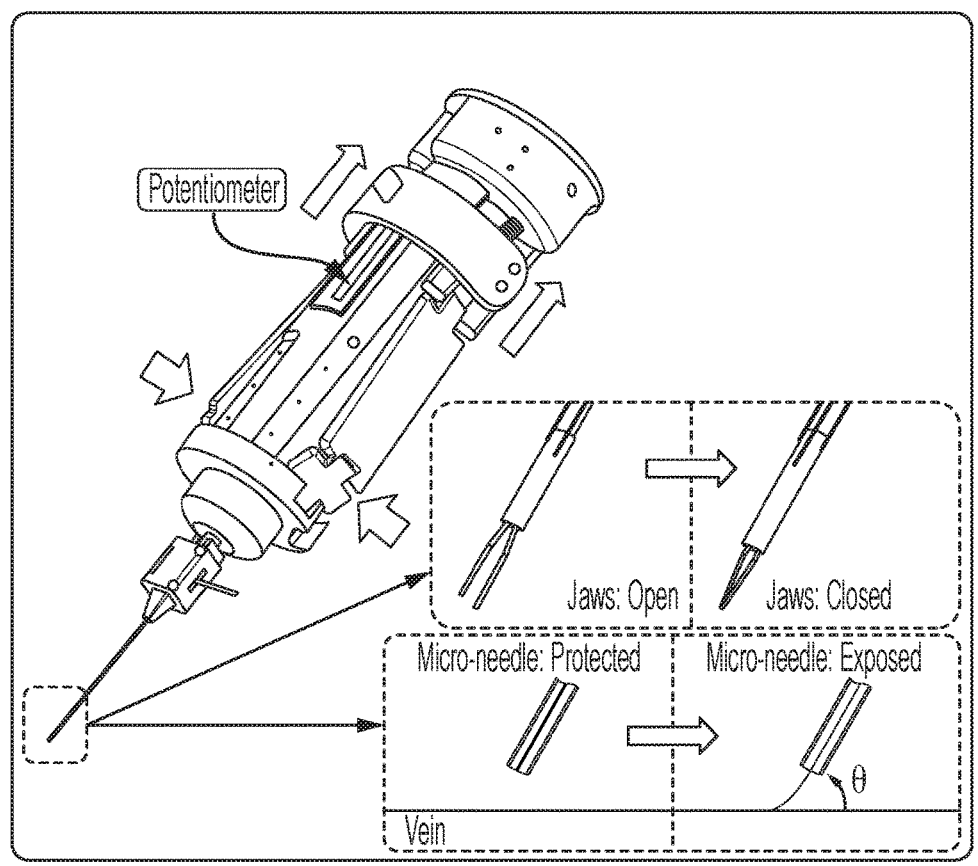
FIG. 3 shows how the attachment can function as a micro-forceps for fine grasping, or as a micro-needle for performing injections into small veins, depending on the tool insert.

The motorized force-sensing attachment and the tool handle (a hand-held micromanipulator is used in some examples, but the approach is applicable to manual tool handles and the other teleoperated/cooperatively controlled robots in the field as well) can be two separate structures which can be independently actuated. FIG. 2 illustrates how the motorized force-sensing attachment can be independently actuated from the micromanipulator, with the handle mechanism providing easy control of the attachment. This can ensure little or no interference between the actuation of the tool tip (micro-forceps or micro-needle) and the motion of the micromanipulator. If a robotic handle (micromanipulator or teleoperated/cooperatively controlled robot) is used, the tool can be used for canceling hand tremor and/or pulsating the tip at a desired frequency/amplitude set by the user. By plugging in various inserts (micro-forceps jaws or a micro-needle), the motorized attachment can be trans-formed into different actuated tools to accomplish various surgical tasks. This is illustrated in FIG. 3.

When a micro-forceps insert is attached, the embodiment can provide strong and safe manipulation of the tissue during surgical tasks like membrane peeling. For easy and intuitive control of the grasping action, the handpiece of the manual/robotic device can easily be converted into a micro-forceps handle via a simple clamp-on handle mechanism. When the sides of the spring loaded mechanism are squeezed, the potentiometer on the handle mechanism is triggered, and the motor of the attachment is driven closing the grasper jaws as shown in FIG. 3. When released, they open back. For triggering the micro-forceps actuation, other interfaces such as a foot pedal, a touch sensor on the tool handle, or the use of simple voice commands are also possible [8].

In the case of a micro-needle insert, the motorized tool can be used to perform injections into very delicate and small vessels. The same actuation principle and the control interfaces can be used to deploy the sharp micro-needle tip and bend it at an optimal angle before insertion into the vein ($\theta$ in FIG. 3).

There are various hand-held micromanipulators [9-15] and teleoperated/cooperatively controlled robots [16-22] that are currently available. The motorized attachment according to some embodiments of the current invention can be integrated with these existing devices since its operation is completely independent. It can be a new end effector to such robotic devices that now provide fine grasping and micro-injection capabilities, and thus enhanced manipulation and safety during microsurgery tasks.

The micromanipulation tool, actuator assembly, and force sensing system can be designed as a "drop-in" standalone module which carries all the necessary sensors and an actuator.

Figure 4:
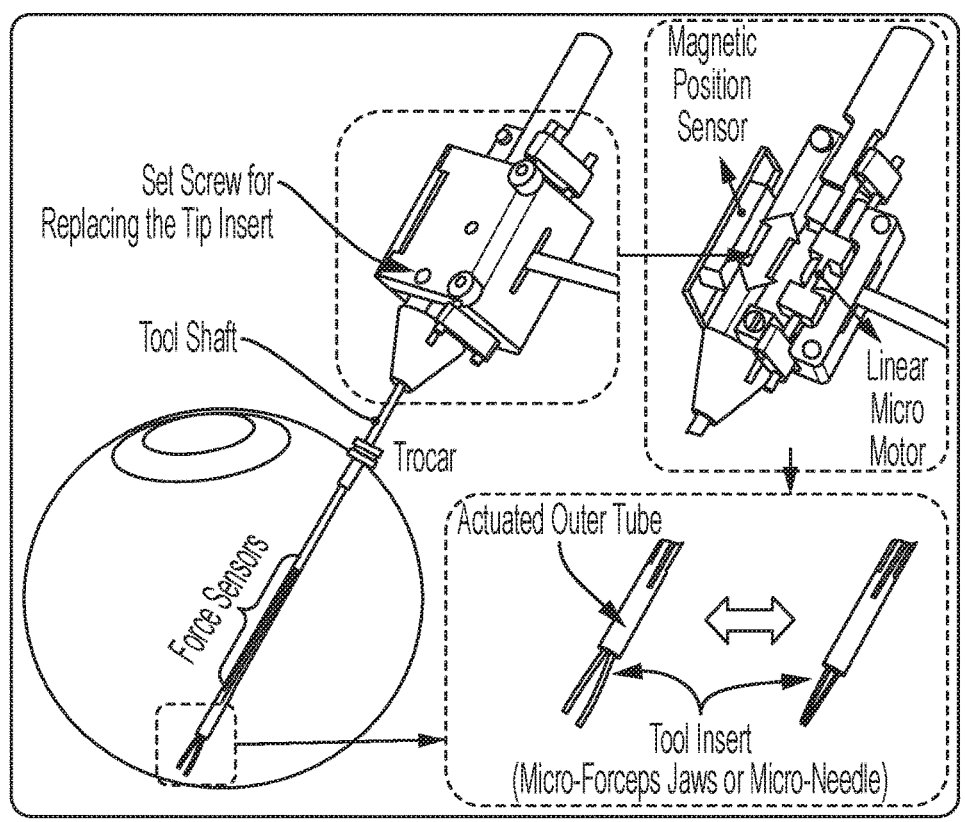
FIG. 4 illustrates actuation of the modular attachment by a linear micro-motor, which translates an outer tube (with the force sensors attached thereon) up and down along the tool axis.
Figure 5:
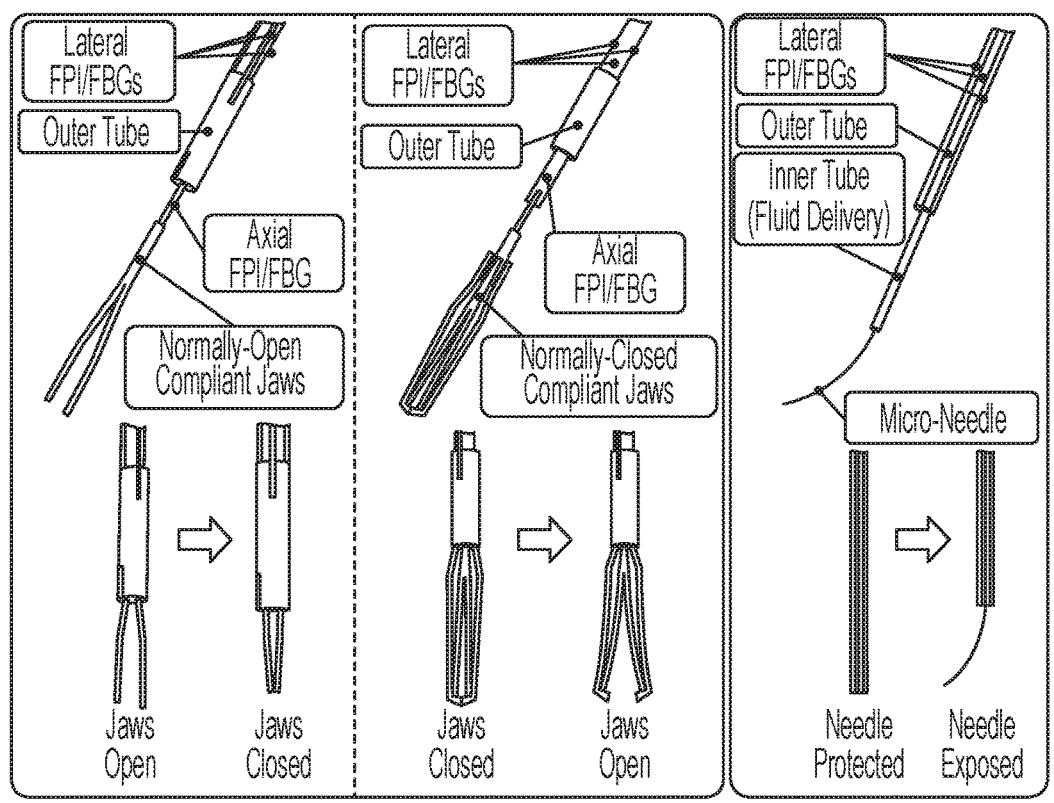
FIG. 5 shows how the attachment can function as a micro-forceps or a micro-needle tool, where the actuation by the linear micro-motor is used either for opening/closing the forceps jaws or deploying the micro-needle.

The module can be actuated by a linear micro-motor, which translates an outer tube (with the force sensors attached thereon) up and down along the tool axis. This is illustrated in FIG. 4. During this actuation, the insert at the tool tip (the forceps jaws or the micro-needle) remains fixed relative to the module body. It can be removable and replaceable to be changed, for example, by using a set screw located on the module. This enables the micromanipulation tool to accommodate various forceps jaw profiles and/or a micro-needle, as shown in FIG. 5, and allows a user to easily switch between different forms (micro-forceps or micro-needle) while preserving the sensorized motorized unit. Such easy replacement principle enables disposable use of the tip inserts (the use of a new tip insert for each operation), prevents the wear and failure of the tool due to sterilization cycles, and thus makes the operation safer.

Figure 6:
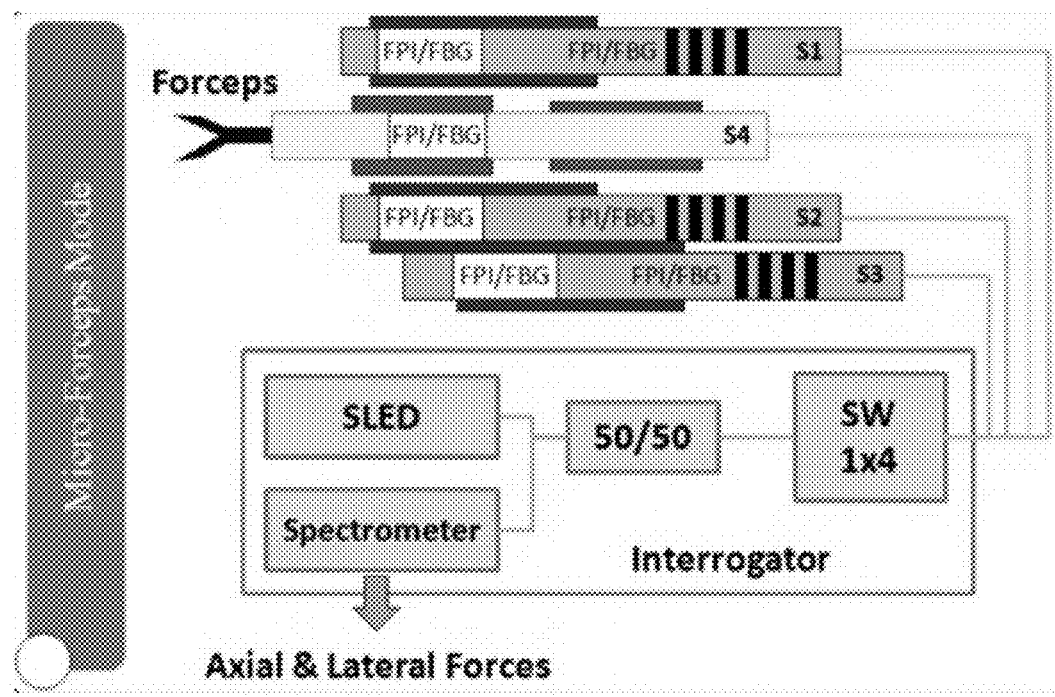
FIG. 6 shows sensors S1-4 (Fabry-Pérot interferometers (FPI)/fiber Bragg grating (FBG)) providing axial and lateral force-sensing capabilities when the system is in micro-forceps mode.
Figure 7:
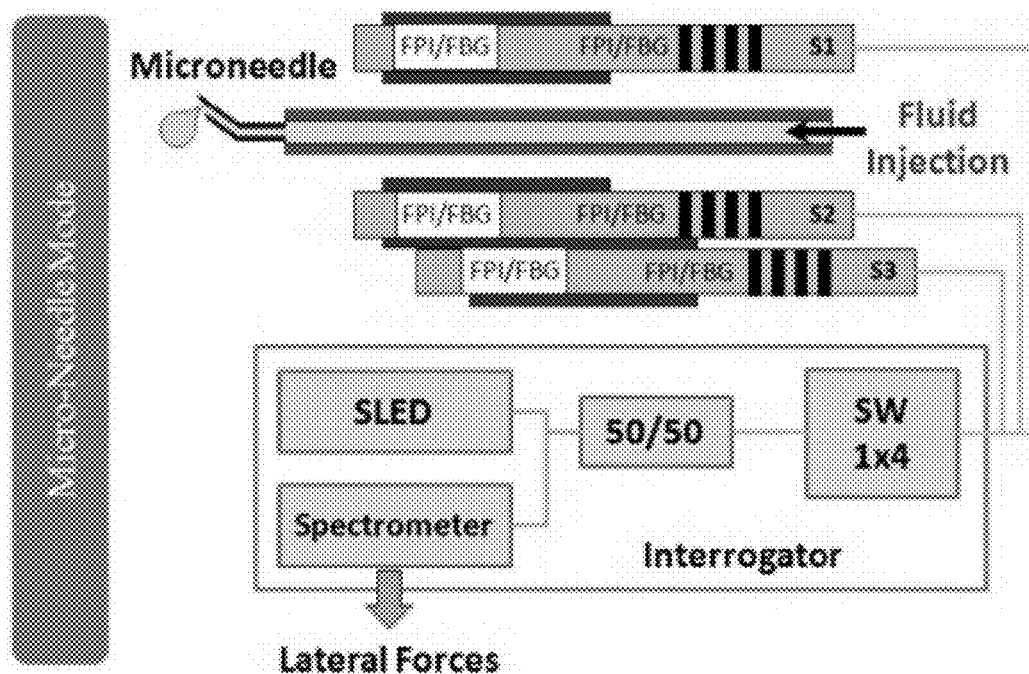
FIG. 7 shows sensors S1-4 (FPI/FBG) providing axial and lateral force-sensing capabilities when the system is in micro-needle mode.

The sensors provide accurate measurement of the forces on the tool tip and/or along the tool shaft. The sensing principle is based on optical strain-gauges. FIGS. 6 and 7 illustrate a plurality of sensors providing axial and lateral force sensing capabilities when the system is in micro-forceps mode and micro-needle mode, respectively. According to some embodiments of the invention, fiber optical sensors, i.e. fiber Bragg gratings (FBG in FIGS. 6 and 7) and/or Fabry-Pérot interferometers (FPI in FIGS. 6 and 7), can be used for their small dimension, high sensitivity, biocompatibility, sterilizability, and immunity from electrostatic and electromagnetic noise. However, the general concepts of the current invention are not limited to only fiber optic sensors. An embodiment can provide lateral force sensing, i.e. sensing in two degrees-of-freedom (DOF), if three sensors (lateral FPI/FBGs in FIG. 5, corresponding to S1, S2 and S3 in FIGS. 6 and 7) are attached around the tool shaft. Each of these three sensors can contain multiple sensing regions to measure not only the tool tip forces, but also to separately measure the forces along the tool shaft (for example at the trocar in FIG. 5—see reference [23]). This concept can further be extended to 3 DOF sensing (to measure not only lateral but also the axial tool-to-tissue forces) by adding an axial sensor connected to the tip in the center (S4 in FIG. 6).

The sensed forces are important for at least three main uses. First, in micro-forceps mode, the magnitude of sensed forces can be used to provide auditory feedback to the operator to help prevent excessive manipulation forces, and thus various clinical complications. This is an extension of a previously presented method to a micro-forceps instrument [24].

Second, in micro-needle mode, the time derivative of the measured force magnitude can be combined with the tool tip velocity information to capture the instant when the needle punctures through the vein wall. When the needle enters into vein, there is a sharp drop in force, which results in a negative value in the time derivative of the measured force magnitude. However, such drops can also happen if needle is retracted back, thus is not sufficient alone to detect venous puncture. Venous puncture is associated with such a force drop only if it occurs during needle insertion (not retraction). There have been robotic systems using only the force information alone to detect venous puncture [25], but none of these systems are handheld devices (they are grounded systems which move the needles with uniform constant speed only inserting it without any retraction). With a handheld device, a constant speed continuous needle insertion is hard to guarantee. Thus using both the force derivative and needle tip speed information is critical to capture the moment of puncture correctly. This corresponds to the instant when the dot product of the two quantities become positive instantaneously (i.e. throughout the insertion period until puncture, the dot product value is either negative or zero). After venous puncture detection, the operator can be warned via auditory feedback, and/or the robotic device (if any) can be used to fixate the tool tip at the detected position to keep the needle tip inside the vein for a longer period (during drug delivery in retinal vein cannulation for example) while causing less trauma on the tissue (see FIG. 8).

Third, in either micro-forceps or micro-needle mode, the direction of the sensed forces can be used for controlling the micromanipulator to generate high frequency and small amplitude vibrations. This can assist the operator in certain microsurgery tasks. For instance, in micro-forceps mode, while delaminating membranes, vibrating the tool tip in the direction of peel (which is determined by the direction of the measured forces) can provide much easier operation, i.e., faster peeling with the same amount of applied force [8]. In micro-needle mode, these micro-vibrations can facilitate the cannulation of thin vessels by providing easier penetration of the needle tip.

Figure 8:
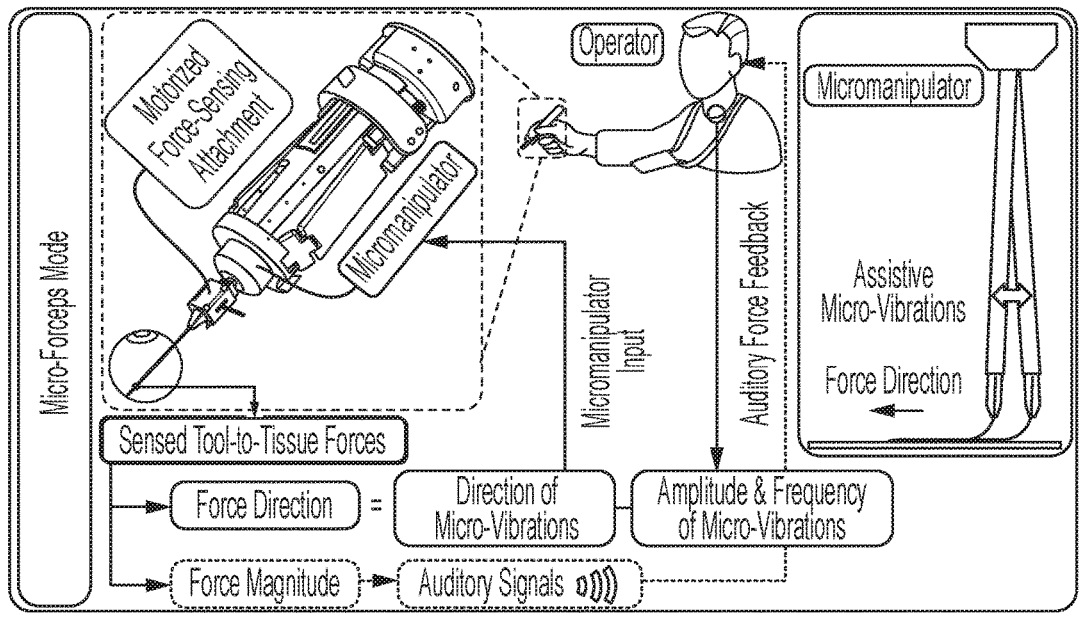
FIG. 8 illustrates the information flow when the system is in micro-forceps mode.
Figure 9:
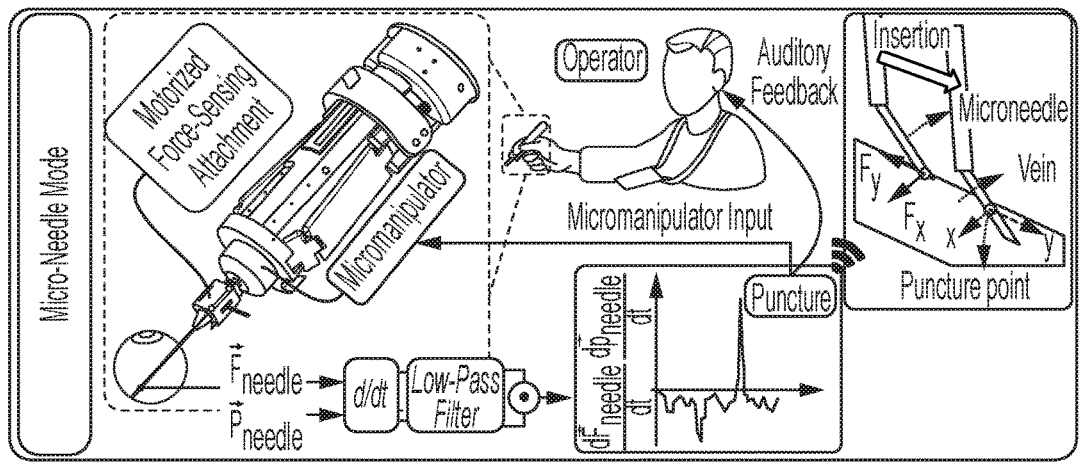
FIG. 9 illustrates the information flow when the system is in micro-needle mode.

The actuation of vibrations for peeling membranes or cannulating veins has not previously been available, which may be due to the lack of robotic force-sensing forceps/micro-needle tools and the computational algorithms used to support them. The motorized force-sensing tool according to some embodiments of the current invention can enable the peeling/cannulation to be done with the help of micro-vibrations along the direction of peeling/needle insertion. The diagrams in FIGS. 7 and 8 summarize the information flow during respectively membrane peeling and vein cannulation procedures according to some embodiments of the current invention. First, the magnitude of the sensed forces are used to provide auditory force feedback to the surgeon in either mode. Second, based on the direction of sensed forces, micro-vibrations are generated on the tool tip by the micromanipulator. This facilitates delamination of membranes and cannulation of veins. Third, in micro-needle mode, the dot product of the tool speed and the time derivative of the measured forces reveals the instant when the needle tip punctures through the vein wall, which can be used to warn the operator and stop further needle penetration with the help of the micromanipulator. Although a handheld micromanipulator is shown in these diagrams, the embodiments of the present invention are not limited to this case, and apply to other robotic systems (teleoperated and/or cooperatively-controlled devices) in the field as well.

For the aforementioned assistive system to work properly, accurate sensing of applied forces should be implemented. There are two potential sources that can result in erroneous force measurements: ambient temperature changes, and the stresses induced on the mechanism during the actuation (opening/closing of forceps, or deployment and bending of the micro-needle).

The software developed that processes the raw measurements from the optical fibers according to an embodiment of the current invention reduces or eliminates the adverse effect of ambient temperature change on the sensed forces. Since the sensors are distributed around the tool shaft equally, assuming that the ambient temperature affects each sensor equally, the software takes the average of all sensor readings and subtracts the average from each of the raw sensor readings. Then the processed reading from each sensor is used to compute a force value. In this way, the computed force is not affected even if the ambient temperature changes.

Figures 10A, 10B:
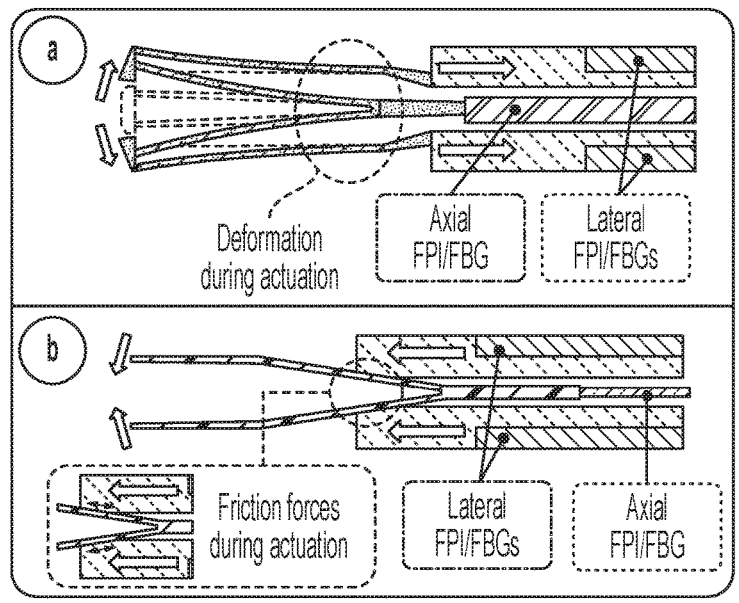
FIG. 10A illustrates how actuation of the motorized tool induces additional forces on the sensors (axial FPI/FBG, and lateral FPI/FBGs) due to structural deformation.
FIG. 10B illustrates how actuation of the motorized tool induces additional forces on the sensors (axial FPI/FBG, and lateral FPI/FBGs) due to frictional forces.
Figure 11:
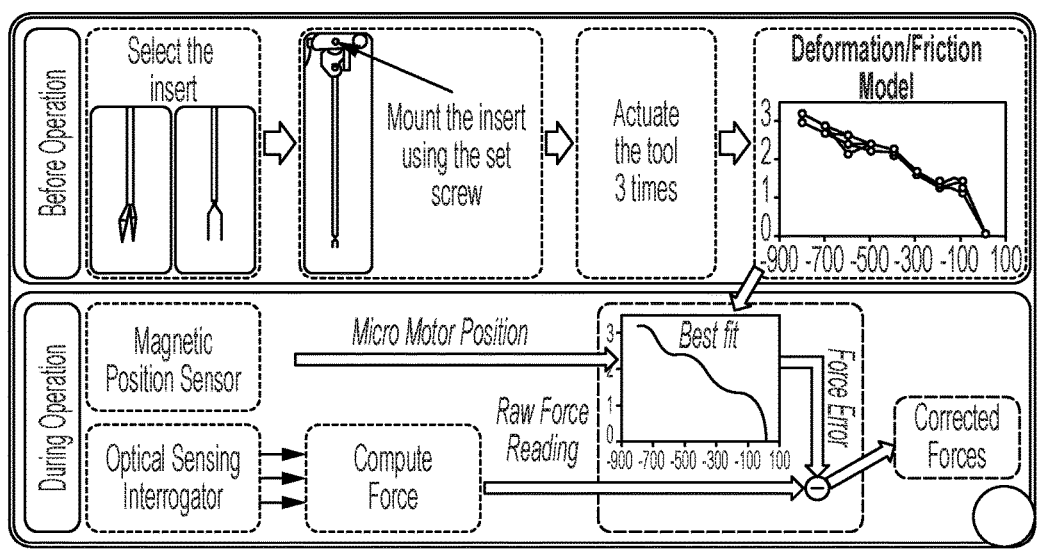
FIG. 11 shows how the forces induced by actuation can be modeled as a function of motor position before operation, and can be compensated based on this model for an accurate force measurement during operation.

The second major issue about actuated tools is the stress induced on the components during actuation, and its erroneous affect in force measurements. To address this, we envision two approaches. The first approach uses customized inserts (such as the micro-forceps tip in FIG. 5) that are connected to both the outer tube and inner tube (carrying the axial FPI/FBG), functioning as a flexure between the two. As the motorized mechanism moves the outer tube relative to the inner tube, the insert deforms to accomplish the desired task (i.e. grasping in case of a micro-forceps), and induces stress on the force sensors. This is illustrated in FIG. 10A, where the force sensors are labeled FPI/FBGs. In the second approach, the outer tube moves relative to the inserts (forceps jaws, or a micro-needle) as in FIG. 5, resulting in varying frictional forces between the two during actuation. This is illustrated in FIG. 10B. In this case, customized insert profiles can be used to fix the contact angle between the insert and the outer tube, and eventually create a more uniform force error throughout the actuation. In either approach, the use of an encoded motor for actuation enables the modeling of the deformation/frictional forces as a function of motor position. In other possible embodiments the encoded motorized actuation could be replaced with encoded manual actuation. After obtaining such a model, the error in force measurement due to the deformation/friction can be estimated and subtracted from the readings to ensure accurate force sensing regardless of tool actuation. The compensation process is illustrated in FIG. 11.

REFERENCES

1. P. Gupta, P. Jensen, and E. de Juan, "Surgical forces and tactile perception during retinal microsurgery," in *Proc. MICCAI'99*, 1999, pp. 1218-1225.
2. M. K. Tsilimbaris, E. S. Lit, D. J. D'Amico, "Retinal microvascular surgery: A feasibility study," *Invest Ophthalmol Vis Sci*, vol. 45(6), pp. 1963-1968, June 2004.
3. R. N. Sjaarda, B. M. Glaser, J. T. Thompson, R. P. Murphy, and A. Hanham, "Distribution of iatrogenic retinal breaks in macular hole surgery," *Ophthalmology*, vol. 102:9, pp. 1387-1392, September 1995.
4. K. Nakata, M. Ohji, Y. Ikuno, S. Kusaka, F. Gomi, and Y. Tano, "Sub-retinal hemorrhage during internal limiting membrane peeling for a macular hole," *Graefes Arch Clin Exp Ophthalmol*, vol. 241, pp. 582-584, July 2003.
5. J. N. Weiss, and L. A. Bynoe, "Injection of tissue plasminogen activator into a branch retinal vein in eyes with central vein occlusion," Ophthalmology, vol. 108:12, pp. 2249-2257, July 2001.
6. K. Kadonosono, A. Arakawa, S. Yamane, E. Uchio, and Y. Yanagi, "An experimental study of retinal endovascular surgery with a fabricated needle," Invest. Opthalmol. Vis. Sci., vol. 52:8, pp. 5790-5793, July 2011.
7. K. Kadonosono, S. Yamane, A. Arakawa, M. Inoue, T. Yamakawa, E. Uchio, Y. Yanagi, and S. Amano, "Endovascular cannulation with a microneedle for central retinal vein occlusion," JAMA Ophthalmol, vol. 131:6, pp. 783-786, June 2013.
8. B. Gonenc, P. Gehlbach, J. Handa, R. H. Taylor, and I. Iordachita, "Motorized Force-Sensing Micro-Forceps with Tremor Cancelling and Controlled Micro-Vibrations for Easier Membrane Peeling," in Proc. IEEE RAS EMBS Int. Conf. Biomed. Robot. Biomechatron. (BioRob'14), 2014, pp. 244-251.
9. W. T. Latt, U-X. Tan, F. Widjaja, C. Y. Shee, and W. T. Ang, "Compact sensing design of a hand-held active tremor compensation instrument for better ergonomics," in *Proc. $2^{nd}$ IEEE RAS EMBS Int Conf Biomed Robot Biomechatron (BioRob)*, 2008, pp. 276-281.
10. R. A. MacLachlan, B. C. Becker, J. Cuevas Tabarés, G. W. Podnar, L. A. Lobes, and C. N. Riviere, "Micron: an actively stabilized handheld tool for microsurgery," *IEEE Trans Robot*, vol. 28:1, pp. 195-212, February 2012.
11. S. Yang, R. A. MacLachlan, and C. N. Riviere, "Design and Analysis of 6 DOF Handheld Micromanipulator," in *Proc. IEEE Int. Conf on Robotics and Automation (ICRA '12)*, 2012, pp. 1946-1951.
12. W. T. Latt, U-X. Tan, C. Y. Shee, and W. T. Ang, "A compact handheld active physiological tremor compensation instrument," in *Proc. IEEE/Amer. Soc. Mech. Eng. Int. Conf. Adv. Intell. Mechatronics*, 2009, pp. 711-716.
13. C. J. Payne, K. Kwok; and G. Yang, "An ungrounded hand-held surgical device incorporating active constraints with force-feedback," in *Proc. IEEE Int. Conf on Intelligent Robots and Systems (IROS '13)*, 2013, pp. 2559-2565.
14. D. Chang, G. M. Gu, and J. Kim, "Design of a novel tremor suppression device using a linear delta manipulator for micromanipulation," in *Proc. IEEE Int. Conf on Intelligent Robots and Systems (IROS '13)*, 2013, pp. 413-418.
15. A. Saxena and R. V. Patel, "An active handheld device for compensation of physiological tremor using an ionic polymer metallic composite actuator," in *Proc. IEEE Int. Conf on Intelligent Robots and Systems (IROS '13)*, 2013, pp. 4275-4280.
16. A. Uneri, M. A. Balicki, J. Handa, P. Gehlbach, R. H. Taylor, and I. Iordachita, "New steady-hand Eye Robot with micro-force sensing for vitreoretinal surgery," in *Proc. $3^{rd}$ IEEE RAS EMBS Int Conf Biomed Robot Biomechatron (BioRob)*, 2010, pp. 814-819.

17. P. S. Schenker, E. C. Barlow, C. D. Boswell, H. Das, S. Lee, T. R. Ohm, E. D. Paljug, G. Rodriguez, and S. T. Charles, "Development of a telemanipulator for dexterity enhanced microsurgery," in Proc. 2nd Int Symp Med Rob Comput Asst Surg, 1995, pp. 81-88.
18. I. W. Hunter, L. A. Jones, M. A. Sagar, S. R. Lafontaine, and P. J. Hunter, "Opthalmic microsurgical robot and associated virtual environment," Comput Biol Med, vol. 25:2, pp. 173-182, March 1995.
19. T. Ueta, Y. Yamaguchi, Y. Shirakawa, T. Nakano, R. Ideta, Y. Noda, A. Morita, R. Mochizuki, N. Sugita, M. Mituishi, and Y. Tamaki, "Robot-assisted vitreoretinal surgery: Development of a prototype and feasibility studies in an animal model," Ophthalmology, vol. 116:8, pp. 1538-1543, August 2009.
20. H. Das, H. Zak, J. Johnson, J. Crouch, and D. Frambach, "Evaluation of a telerobotic system to assist surgeons in microsurgery," Comput Aided Surg, vol. 4:1, pp. 15-25, 1999.
21. P. S. Jensen, K. W. Grace, R. Attariwala, J. E. Colgate, and M. R. Glucksberg, "Toward robot-assisted vascular microsurgery in the retina," Graefes Arch Clin Exp Ophthalmol, vol. 235:11, pp. 696-701, November 1997.
22. A. P. Mulgaonkar, J. P. Hubschman, J. L. Bourges, B. L. Jordan, C. Cham, J. T. Wilson, T. C. Tsao, and M. O. Culjat, "A prototype surgical manipulator for robotic intraocular micro surgery," Stud Health Technol Inform, vol. 142, pp. 215-217, 2009.
23. X. He, M. A. Balicki, J. U. Kang, P. L. Gehlbach, J. T. Handa, R. H. Taylor, and I. I. Iordachita, "Force sensing micro-forceps with integrated fiber bragg grating for vitreoretinal surgery," in *Proc. of SPIE*, vol. 8218, pp. 82180W 1-7, February 2012.
24. The Johns Hopkins University, "Method for presenting force sensor information using cooperative robot control and audio feedback," PCT Patent Publication No. WO 2012018821 A2, Feb. 9, 2012.
25. A. Zivanovic, and B. L. Davies, "A robotic system for blood sampling," IEEE Trans. Inf. Technol. Biomed., vol. 4:1, pp. 8-14, March 2000.

The following examples describe some further concepts of the invention with reference to particular examples. The general concepts of the current invention are not limited to the particular examples.

Example 1—Force-Sensing Micro-Forceps

The vitreoretinal practice is a target domain for robotic assistive systems, which can provide fine motion control, limit applied forces, and thus improve surgical outcomes. In order to eliminate hand tremor of the surgeon, and thus provide more accurate manipulation of the tissue, several teleoperated systems have been previously proposed [1-6]. Among these systems is the Steady-Hand Robot which is a distinct approach to providing passive tremor suppression. It is based on a cooperative control scheme where the surgeon and a stiff robot arm hold the surgical instrument together [7]. In contrast grounded approaches, fully handheld micromanipulators have been developed with a recent increase in interest [8-12]. Such systems offer a smaller footprint, greater ease in integration into the surgical workflow, and more intuitive operation. These devices share a common operation strategy to correct erroneous motion due to hand tremor of the surgeon. They first sense their own motion via either optical tracking or inertial sensing, then decompose this motion into tremulous and voluntary components, and finally use their actuators to move the tool tip and counteract the tremulous components. One of the instruments that falls into this category is Micron, a handheld actively stabilized micromanipulator developed by Riviere et al. at Carnegie Mellon University [8]. It uses optical tracking and piezoelectric actuators for deflecting the tool tip. Micron was shown to suppress tremor effectively, but it still has unexplored potential utility for tasks such as membrane peeling by operating in different modes rather than solely in tremor canceling mode. Developing such assistive modes for using Micron in a membrane peeling task first requires the advent of a proper micro-forceps tip that will firmly grasp the tissue while not interferin 13 with Micron's tremor canceling behavior and this was not available until recently [50].

Membrane peeling is essentially a two-phase procedure. In the first phase, the surgeon needs to approach the membrane, grasp and lift it to create an edge. For this task, positioning accuracy, and thus tremor suppression is important. The second phase is the delamination of the grasped membrane, where the main concern is limiting the exerted forces on the retina rather than canceling the tremor. Although several micromanipulators were developed for assisting vitreoretinal surgery before, the focus has so far been on suppressing the hand tremor, primarily focusing on the initial phase. For assisting the second phase of this procedure, there are motivating applications in other fields, such as inserting a biopsy needle [14] and suturing [24], where reciprocation of the needle was shown to facilitate the advance of the needle through tissue and penetration of the site of interest. The potential impact of introducing such vibrations while delaminating membranes in vitreoretinal practice is novel.

In order to limit the applied forces in vitreoretinal practice, a family of force-sensing instruments has been developed at Johns Hopkins University using fiber Bragg grating (FBG) strain sensors to measure the forces directly at the tool tip. First, a single degree of freedom (DOF) force sensing tool [15] and then a 2-DOF pick-like instrument [16] were built with FBG sensors. The 2-DOF pick was used in combination with the Steady-Hand Robot [17] as well as with Micron [18]. Compared with a pick tool, forceps provide increased control due to the additional degree of freedom for grasping the tissue. This enables removal of the membrane from the eye in a single step [19], which is why forceps are more practical and more commonly used in vitreoretinal surgery. With this motivation, tool development continued with a manual pair of 2-DOF force-sensing forceps [20], followed by a 2-DOF forceps that can be used with the Steady-Hand Robot [21]. We recently presented a 2-DOF force-sensing micro-forceps for Micron [13]. This design was shown to be sufficiently compact and lightweight for Micron to operate properly, and benefits of such force-sensing tremor-canceling system for membrane peeling was demonstrated on artificial bandage phantoms. However, tests on biological tissues revealed limitations and clinical feasibility issues.

Described herein are the design and evaluation of an integrated system combining Micron and a new force-sensing motorized micro-forceps which in fact also can be used in combination with any of the currently available active tremor-canceling handheld micromanipulators such as in [11] and [12]. The target clinical application is membrane peeling in vitreoretinal surgery, though the system can certainly be used for other applications. The system (1) attenuates hand-tremor when accurate positioning is needed, (2) provides auditory force feedback to the user so that the exerted forces are kept at a safe level, and (3) pulsates the tool tip at high frequency to provide ease in delaminating membranes. We will first present the design and calibration of our new tool addressing the previously encountered clinical challenges. This will be followed by system integration steps and the operation mode. We also present experimental performance assessment for membrane peeling on two types of phantoms: a bandage phantom and raw chicken eggs.

Figures 12A, 12B:
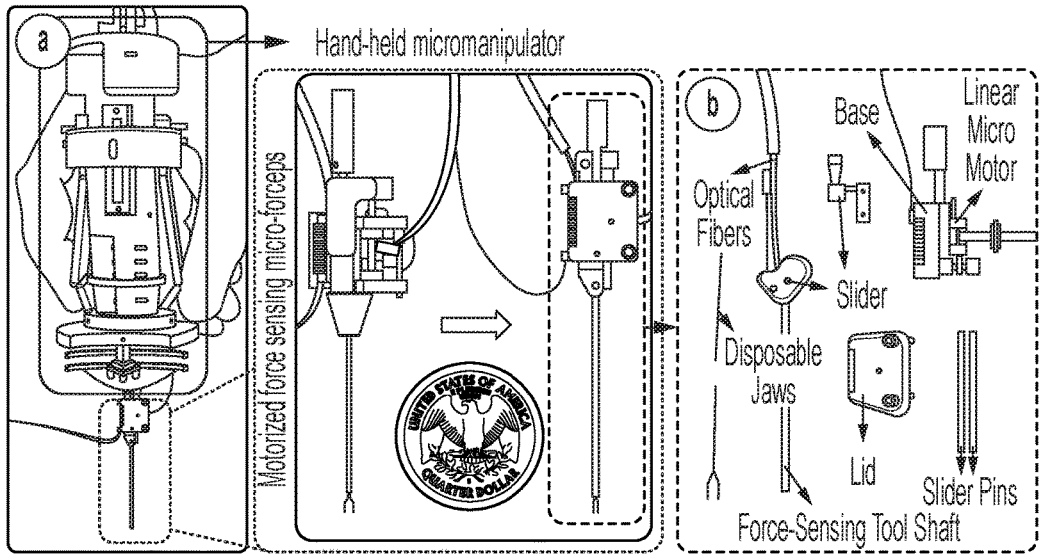
FIG. 12A shows a hand-held manipulator with motorized force sensing microforceps according to some embodiments of the invention.
FIG. 12B shows components of the motorized force sensing microforceps shown in FIG. 12A.

FIG. 12A shows a hand-held manipulator with motorized force sensing microforceps according to some embodiments of the invention. An earlier prototype of the motorized force sensing microforceps is shown on the left, and a more compact design is shown on the right. FIG. 12B shows components of the more compact design. The tip can be easily replaced to accommodate different jaw types for different surgical tasks and prolonged use.

Figures 13A, 13B:
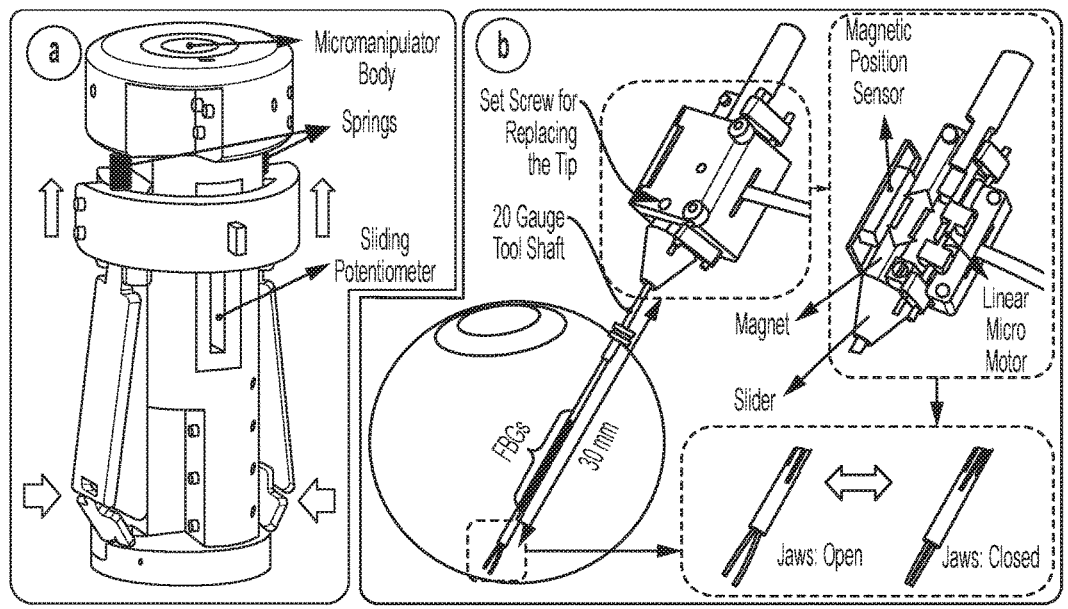
FIG. 13A shows the handle mechanism of the force-sensing microforceps.
FIG. 13B shows the motorized force-sensing tip with replacable jaws.

The micro-forceps consists of two mechanically decoupled pieces: the handle mechanism, and the motorized force-sensing tip. The handle mechanism, shown in FIG. 13A, is designed as a clamp-on component to convert the handpiece of any tremor-canceling micromanipulator into a micro-forceps handle while preserving the intuitive actuation mechanism on the existing disposable forceps from Alcon, Inc. (Fort Worth, Tex.), and not interfering with the operation of the micromanipulator. Disposable Alcon forceps are some of the most common standard instruments for membrane peeling today and are actuated simply by squeezing the sides of the instrument handle. The squeezing motion causes the tube forming the tool shaft to slide in the distal direction so that the graspers are closed [21]. In our case, however, such rigid coupling between handle motion and tip actuation is not possible since it would significantly interfere with the actuators of the micromanipulator. Instead of such a mechanical coupling, we use a sliding potentiometer on the handle to assess forceps closure. The sides of the handle mechanism are normally kept propped open by two springs as shown in FIG. 13A. Compressing the sides causes the sliders to move up along the tool handle, inducing a voltage change in the potentiometer output, and providing the required input to the motorized force-sensing tip. With the help of set screws, this mechanism can clamp around any cylindrical micromanipulator body up to 25 mm in diameter, transforming it into a micro-forceps handle.

The motorized force-sensing tip is now described. To design a clinically feasible micro-forceps tip that is compatible with various micromanipulators, there are four main challenges that need to be resolved: (1) integrating accurate force sensing capabilities while preserving the grasping motion of the forceps, (2) avoiding interference between the micromanipulator's own actuation and the opening/closing action of the forceps, (3) generating a self-standing universal module for compatibility with various handheld manipulators, and (4) enabling easy replacement of the grasper jaws for accommodating different jaw types for different surgical tasks, and for disposable use. This requires a very compact and lightweight micro-forceps module that can be actuated independently regardless of the attachment site on the micromanipulator, and that carries all of the force-sensing elements on it. Under these constraints we designed our "drop-in" micro-forceps as shown in FIG. 13B using the components shown in FIG. 12B.

Figures 14A, 14B, 14C:
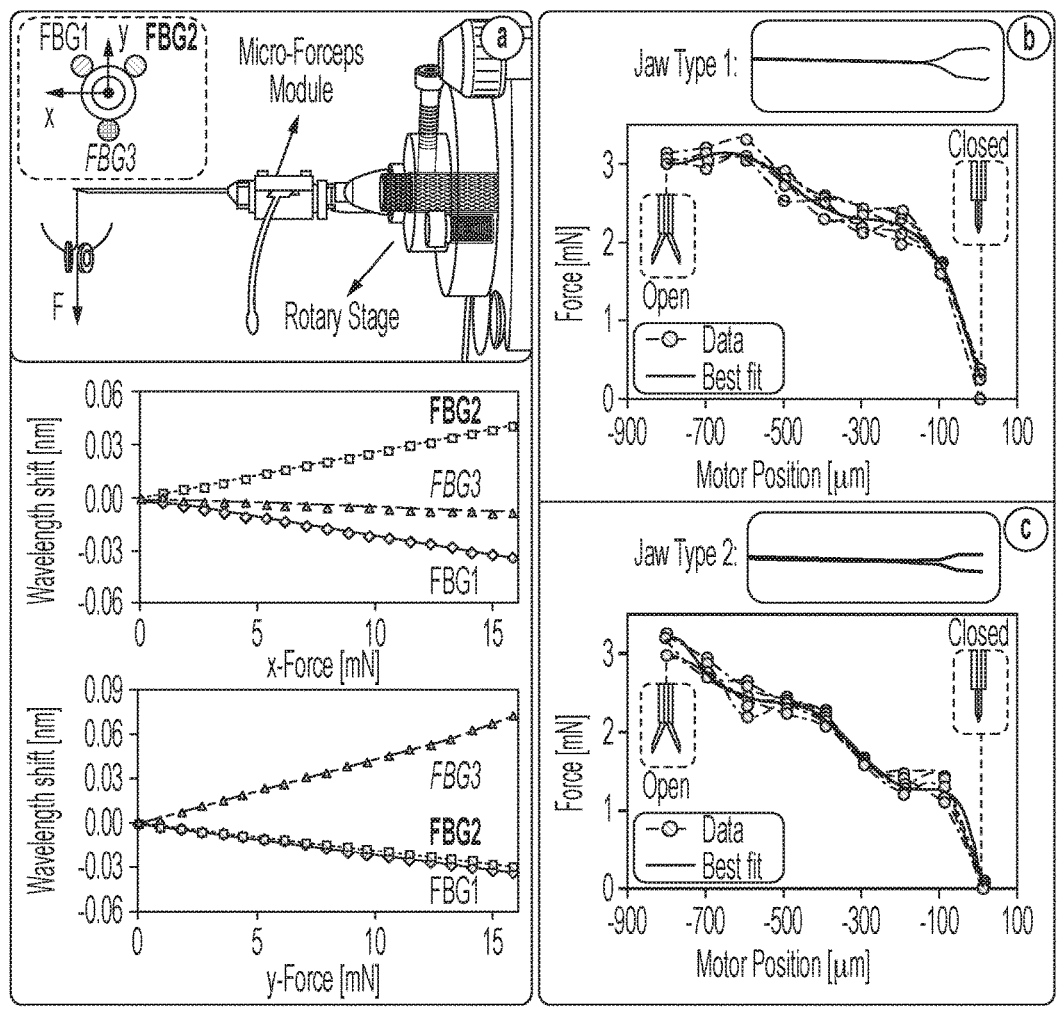
FIG. 14A shows calibration results for all FBGs with tip loading in the x-axis direction (upper) and y-axis direction (lower)
FIG. 14B shows measured forces versus motor position for jaw type 1 while no external force is applied on the tool tip.
FIG. 14C shows measured forces versus motor position for jaw type 2 while no external force is applied on the tool tip.

Reusable forceps require cleaning and sterilization after every operation. As the tool goes through many cycles of operation, the resulting material fatigue and change in surface properties diminish the grasping quality. Consequently, the forceps jaws cannot grasp the membrane as required and in the worst case they may break during the surgery. In addition, depending on the thickness of targeted tissue, surgeons may need to use micro-forceps with varying grasper jaw profiles. For instance, the grasper jaws shown in FIG. 14B are used for peeling thinner membranes such as internal limiting membranes, whereas the jaws in FIG. 14C are often used for thicker layers such as epiretinal membranes.

In order to avoid the problems and costs associated with reusable forceps, and to accommodate different jaw types for various clinical tasks, our micro-forceps module uses easily replaceable disposable forceps jaws that are at this time taken from the standard 23 Ga Alcon disposable microforceps. The normally open jaws are fixed to the base via a set screw located on the lid. The lid, base and slider shown in FIG. 12B are polycarbonate parts, though the design is not limited to these materials. According to some embodiments of the invention, the tool shaft is a 23 Ga stainless steel tube. It is attached to a slider, which is moved back and forth along the pins of the base by a linear micro motor, Squiggle-RV-1.8 by New Scale Technologies Inc. Driving the slider forward pushes the tool shaft towards the tip, thus squeezing and closing the forceps jaws. The selected micro motor supplies enough force for this task in a very small (2.8× 2.8×6 mm), and light weight (0.16 grams) package. Fully opening and closing the jaws requires a travel distance of 0.8 mm, which is well below the motor's limit (6 mm). A bar magnet is attached on the side of the slider. The position of the slider, and thus of the micro motor, is tracked via the magnetic position sensor fixed on the side of the base.

To integrate force sensing capabilities, FBG strain sensors (Smart Fibers, UK) were selected due to their small dimension, high sensitivity, biocompatibility, sterilizability, and immunity from electrostatic and electromagnetic noise. Following the fabrication method presented in [16], three FBGs were fixed evenly around the 23 Ga tubular tool shaft using medical epoxy adhesive. In order to monitor the FBGs, an optical sensing interrogator, sm130-700 from Micron Optics Inc. (Atlanta Ga.), was used. The outer diameter of the finalized tool shaft is approximately 0.9 mm, and is small enough to fit through a 20 Ga trocar. The module weighs about 1.9 grams. While specific materials and instrument models are listed herein, these are purely exemplary, and the present invention is not limited to these materials and models. Other materials and instrument models may be utilized, as will be appreciate by one of ordinary skill in the art.

Calibration and force computations are now described. The setup and protocol presented in [16] was followed to calibrate the new micro-forceps module. A linear reproducible behavior was observed for all FBGs as the transverse loading on the tool tip was gradually increased and decreased. The slopes of the response curves presented in FIG. 14A correspond to the following calibration matrix:

$$K = \begin{bmatrix} 0.00211 & -0.00264 \\ 0.00262 & -0.00184 \\ -0.00052 & 0.00448 \end{bmatrix}$$

The pseudo-inverse of the calibration matrix (K+) is used in the linear relationship given by (1.1) to compute the tip forces (F) from FBG wavelength shifts ($\Delta S$).

$$F = K + \Delta S \qquad (1.1)$$

This algorithm was shown to remove the influence of temperature effectively [16]. Thus, the sensed forces are immune to ambient temperature changes. Furthermore, the shaft of the disposable tip in comparison to the actuation tube is very thin, and thus has no significant effect on the overall stiffness of the tool shaft. Thus even if the tip is replaced, the calibration matrix remains the same.

The grasping action in this design is provided by squeezing the forceps jaws by sliding the tubular tool shaft forward. During this motion, various external loads and friction forces are exerted on this tube, which is also carrying the force-sensing FBGs. As the forceps are closed and opened, FBGs are influenced by these inner actuation forces resulting in a repeated and consistent change in force readings even when there is no external loading on the tip. The force variation due to actuation depends on (1) the type of the attached forceps jaws, and (2) the jaw orientation relative to the base. The sensed actuation forces are usually comparable (up to 3 mN as in FIGS. 14B and 14C) with the amplitude of most forces during vitreoretinal practice (routinely below 7.5 mN). Due to various structural factors, such as the grasper jaw geometry, friction forces and material properties, the effect of inner actuation forces is usually complex, and thus hard to predict. In order to cancel this systematic error, we implemented a correction routine, illustrated in FIG. 15, that can be performed after each jaw replacement.

Figure 15:
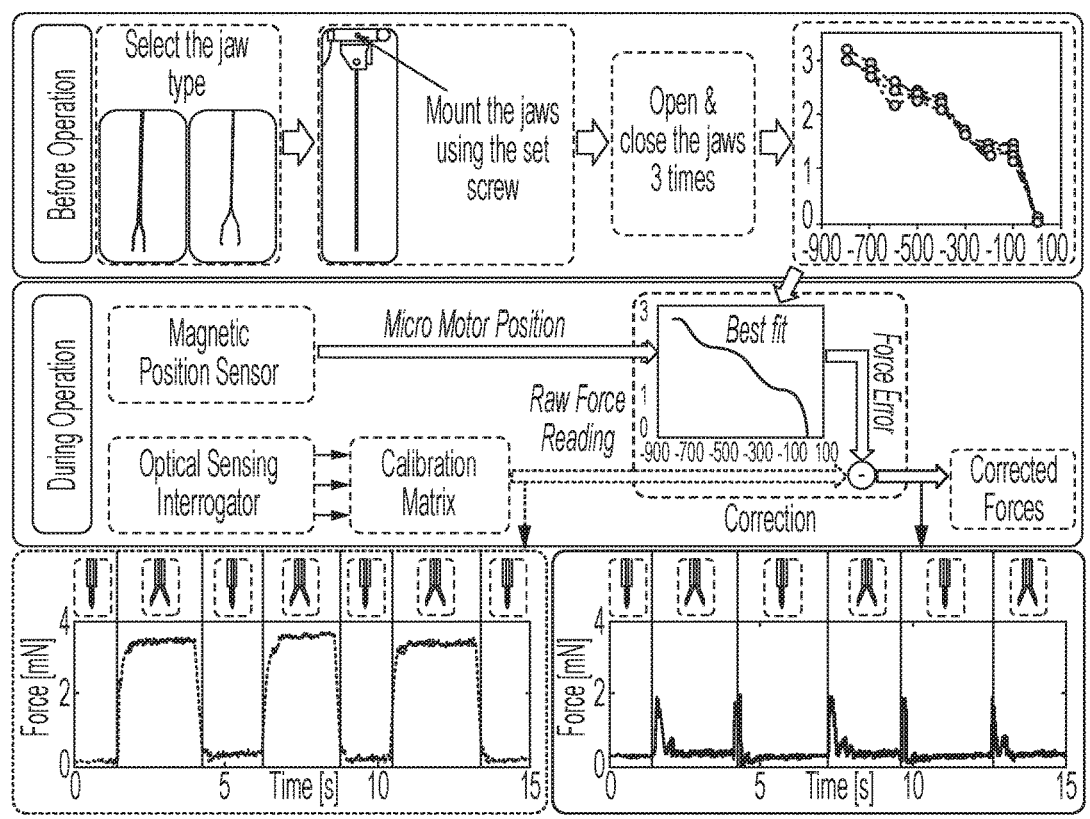
FIG. 15 illustrates the correction routine for compensating against the inner actuation forces and maintaining accuracy of force readings while opening and closing the grasper jaws.

Before the operation, the desired jaws are mounted using the set screw on the lid (FIG. 13B). Then, with no external loading on the tip, the grasper jaws are opened and closed three times while the variation in sensed forces is recorded. This results in a mapping between the micro motor position and force error specific to that particular jaw type and mounting orientation. Then a polynomial is fit to the acquired data. Based on the best fit and sensed motor position, the induced forces due to actuation can be estimated (within a ±0.15 mN envelope) and subtracted from the measured values to obtain a corrected force reading. This provides a significant reduction in force variation as the forceps is closed and opened repeatedly. As shown in FIG. 15, without such correction, opening the forceps jaws induces an error that is slightly larger than 3 mN. The correction routine lowers the error down to 0.3 mN. This indicates that our tool is able to sense transverse forces within an accuracy of 0.3 mN after correction. The jumps on the corrected data correspond to the instant when the actuation tube starts and stops moving, and are mainly due to inertial effects. These jumps can further be reduced by integrating the acceleration term in the correction routine, but has no significance for practical use since the forces while grasping the tissue (while the jaws are stationary) are of interest.

Figure 16:
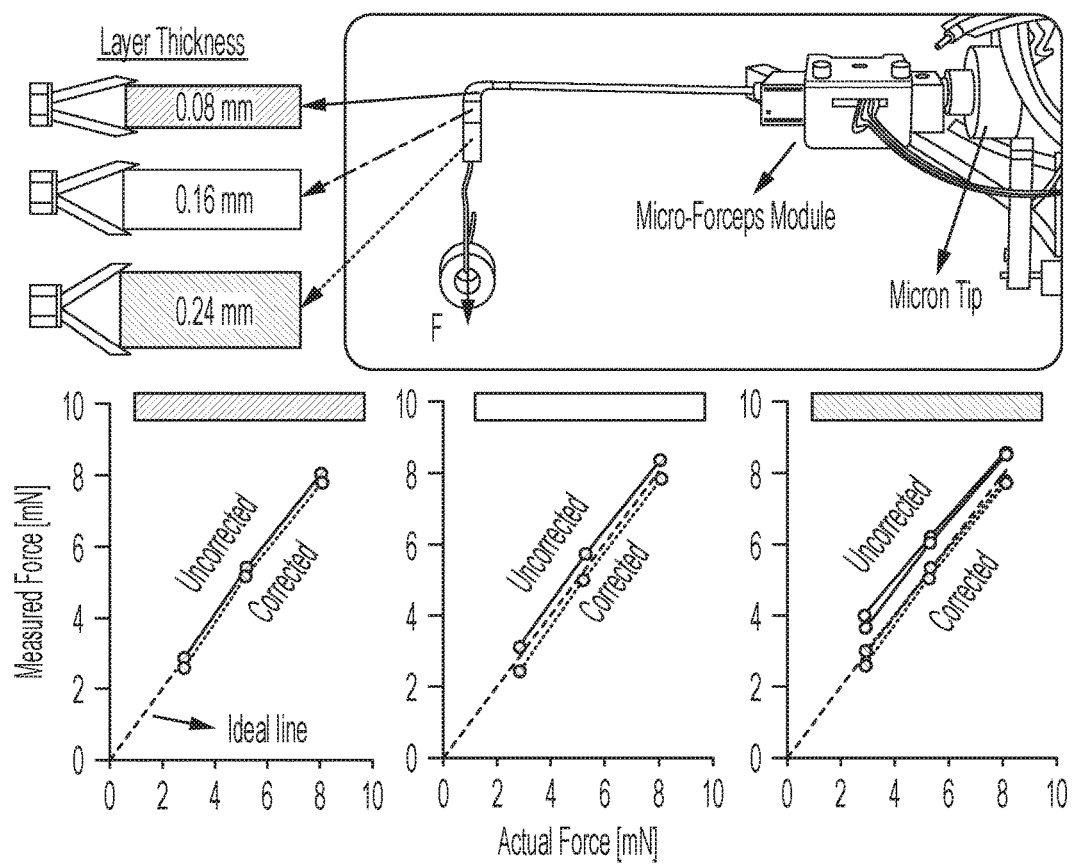
FIG. 16 shows the effect of grasped layer thickness on the force sensing accuracy of the system in micro-forceps mode.

In vitreoretinal practice, surgeons may need to manipulate tissues with varying thickness. Depending on the grasped layer thickness, the jaw opening and the final motor position would change, resulting in different offsets in the raw force reading. The force correction routine based on motor position ensures that the computed tip forces remain accurate regardless of the thickness of the grasped material. In order to validate this, we did experiments for three different layer thicknesses, and three different tip load levels on the setup shown in FIG. 16. The grasping tab carrying the loads is made of bandages and has a non-uniform cross section. The top segment consists of a single layer bandage, while adjacent white and black segments have layers stacked on top of each other, resulting in 0.08 mm, 0.16 mm and 0.24 mm thick material respectively. During the test, the strip was grasped from one of these segments, and washers were hung to increase the forces on the tool tip gradually. The force readings were recorded with and without the correction routine while loading and removing washers. The test was repeated for each segment on the strip. When grasped from the thinnest segment, the measured forces were observed to be very close to the actual values, even without the correction routine. However, as the grasped layer got thicker, the measured values deviated from the ideal line, and thus the correct force value, more if the correction routine was not applied. With the correction routine, the measured forces always remained accurate, regardless of the thickness of the grasped segment.

Software implementations were completed using LabVIEW control software. The control scheme of the developed system consists of three independent loops as shown in FIG. 17: micron control, forceps tip control, and auditory force feedback loops.

Micron uses ASAP optical sensors to determine its handle motion [8]. Then this motion is separated into its voluntary and tremulous components, since the vibrations have different frequencies. In the frequency domain the tremulous components are generally around 8-12 Hz. The system is able to automatically identify them and compensate. The voluntary components can be in the range of 2-4 Hz. Based on the tremulous components, the required actuator input to Micron's piezoelectric actuators are determined, and the tip is deflected. This completes the tremor suppression control loop which was previously developed by Riviere et al. Herein, we extended the existing LabVIEW control software to include an additional operation mode to assist membrane peeling. This optional mode enables the user to inject controlled high frequency pulses on the tool tip trajectory. The frequency and amplitude of the vibrations are set by the user. When this mode is inactive, the system works in regular tremor cancellation mode, which is good for accurate tool tip motion while approaching the tissue and grasping it. Upon activation of the new mode, Micron not only cancels hand tremor but also starts vibrating the tool tip at the set frequency and amplitude. This feature, by providing an analogous tip motion to the reciprocating needle in biopsy applications [14], may theoretically help break the bonds between the fibrous tissue and the retina surface for easier delamination.

Figure 17:
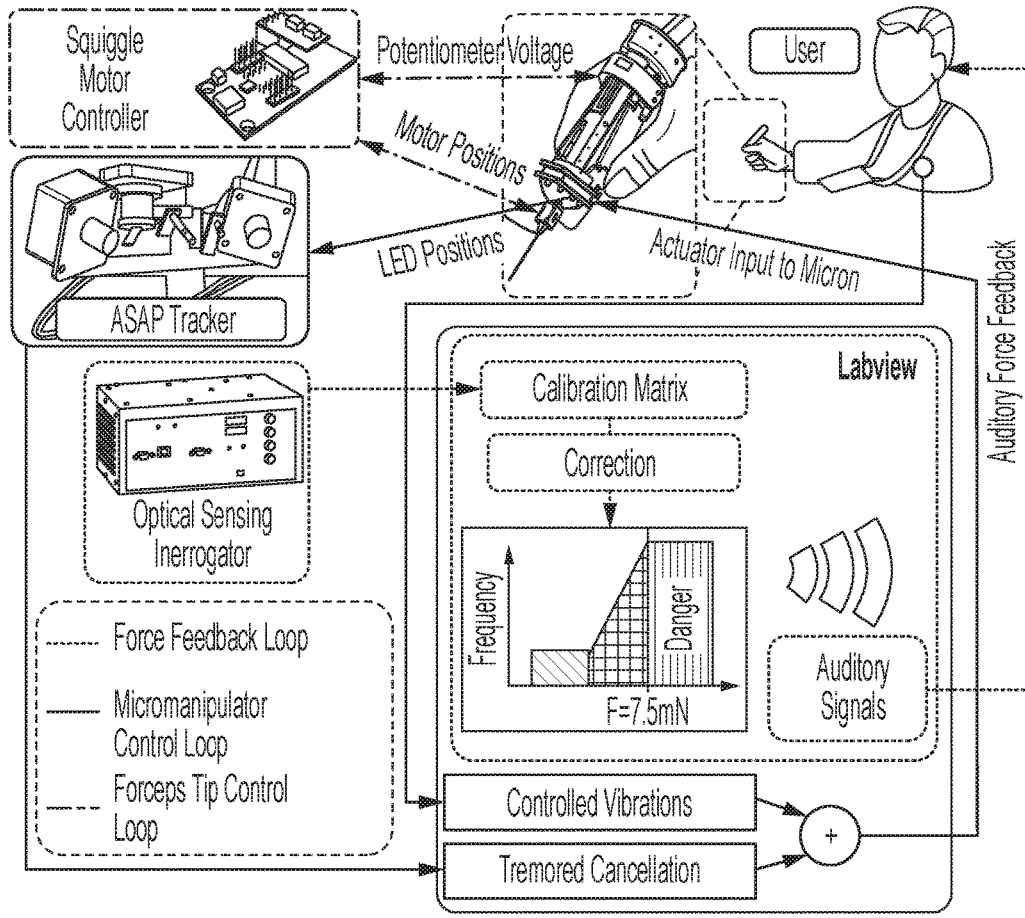
FIG. 17 shows the control scheme of the integrated system.

The control loop associated with the actuation of the forceps is shown in dashed lines in FIG. 17. Accordingly, analog position servo input is provided by the sliding potentiometer on the handle mechanism to the Squiggle motor controller. The magnetic sensor on the forceps tip provides position feedback to accomplish accurate closed loop control, opening or closing the grasper jaws without noticeable delay.

The auditory force feedback loop is shown dotted lines. During operation, the wavelength information from each FBG channel is collected and processed at 1 kHz and transmitted over TCP/IP to the LabVIEW environment. Utilizing the calibration matrix, forces are computed. Based on forceps configuration (linear motor position), the computed force value is corrected to obtain tip forces. These tip forces are then converted into auditory signals. The frequency of these audio signals changes with the level of the applied force [17]. Depending on the frequency of the auditory feedback, the user adjusts tool motion so that the applied forces do not exceed 7.5 mN, which we define as the border for the danger zone in membrane peeling based upon our prior in-vivo experience [20].

To simulate membrane peeling, tests were done on two types of phantoms, which have previously been used in our laboratory and reported to be suitable surrogates for an epiretinal membrane: a bandage phantom, and the inner shell membrane (ISM) of raw chicken eggs. The bandage phantom, comprising 2 mm wide strips cut from 19 mm Clear Bandages (RiteAid brand), provides a very consistent platform, and is easy to obtain enabling ample tests. ISM of raw chicken eggs is a biological tissue exhibiting heterogeneous properties, and thus is a more realistic phantom for membrane peeling trials. However, the number of tests that can be done using ISM is limited since a single egg shell is used for each test.

The goal of the experiments was to test the new micro-forceps tip and observe the effect of the new "controlled vibration mode" at various frequencies in comparison to freehand and regular tremor cancellation performances. For this reason, the tests were done in five sets:
(1) Freehand peeling;
(2) Micron-assisted peeling with regular tremor cancellation; (3, 4, 5) Micron-assisted peeling with tremor cancellation and controlled vibrations at 10 Hz, 30 Hz, and 50 Hz.

In sets 3 to 5, sinusoidal oscillations at the specified frequency were injected to the commanded forceps tip trajectory to oscillate the tool tip back and forth along the peeling direction. The amplitude of vibrations were kept constant at 100 μm.

Figure 18:
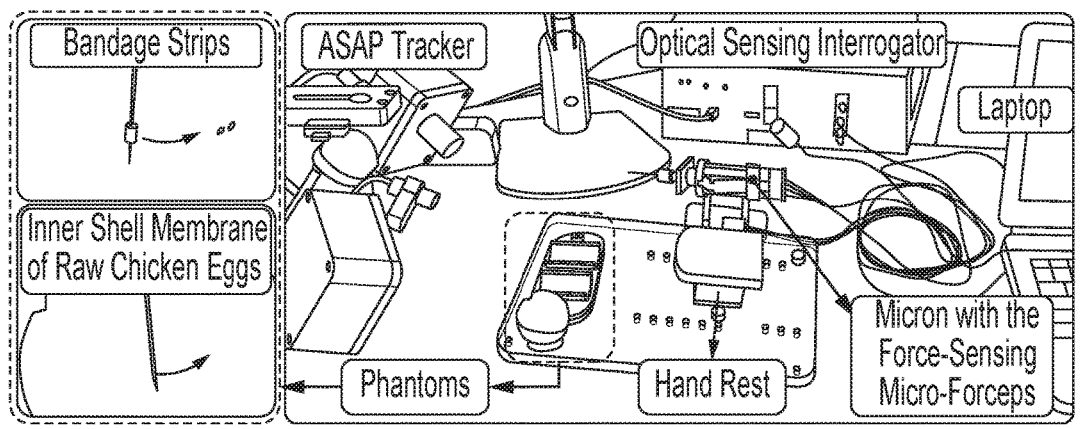
FIG. 18 shows the setup for membrane peeling experiments on a bandage phantom and the inner shell membrane of raw chicken eggs.

Per set 15 trials on the bandage phantom, five trials on ISM were completed. The experiments were performed by a non-surgeon user by alternating the sequence of sets initially on bandage phantom, and then on ISM using the setup shown in FIG. 18. In all cases, the user was provided with auditory force feedback, clearly indicating whether the applied forces are close to or beyond the safety threshold (7.5 mN). The challenge was to peel the membranous layer off as quickly as possible while maintaining the peeling force below the threshold, and thus adjusting the peeling speed based on the force feedback. By fixing the exerted forces at their maximum allowable level, the corresponding peeling speed was observed to evaluate the ease of peel in each set.

Before data collection, an extensive training period (~1 hr) was allowed for the subject to become accustomed to the system and phantoms, and to minimize learning curve effects in the recorded measurements. During data collection, the tool tip force and position and the Squiggle motor position were recorded. Based upon the Squiggle motor position, the starting and ending points of the delamination were identified in the acquired data. The assessment was based upon the applied forces and tool tip positions during this period. Welch's power spectral density estimate was used to verify tremor canceling and vibration behavior. The means of peeling force and speed data were compared using one-way ANOVA followed by Tukey's HSD (honest significant difference) test. Statistical significance was defined as $p<0.05$.

Figure 19:
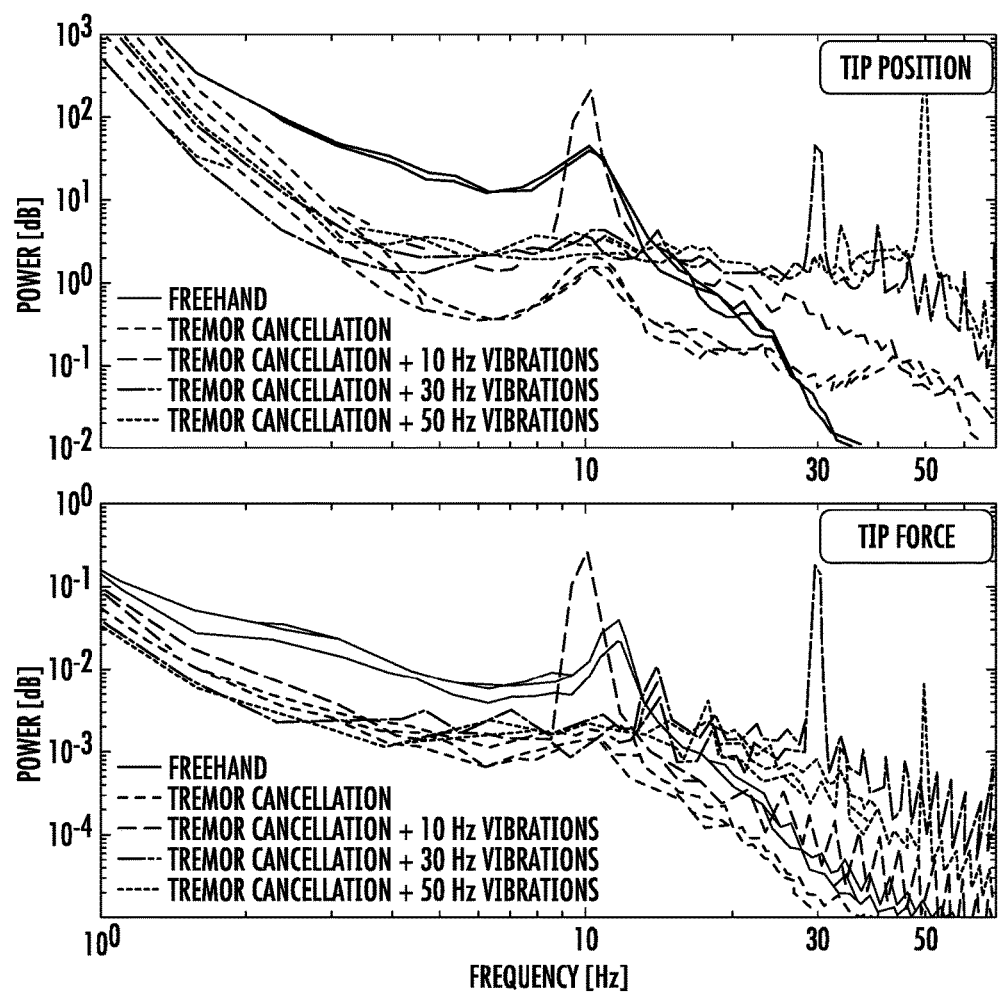
FIG. 19 shows power spectra of tip position and tip forces measure while peeling bandages (three trials per set are shown)

Frequency analyses on tip position and measured peeling forces for three sample trials per set are shown in FIG. 19. The frequency of physiological hand tremor in normal humans ranges from 8 to 12 Hz [22]. The prominence of a peak around 10 Hz in the plots of freehand trials is primarily due to subject's hand tremor. When the tremor cancellation feature of Micron was activated, this peak was largely attenuated and the high frequency components (2-20 Hz) were overall reduced by 80-90% in both position and force spectra. This confirms that the structural modification done for transforming the micromanipulator into a micro-forceps tool, and thus the added inertia at the tip, does not adversely affect the tremor cancelling functionality of Micron. The effect of adding controlled vibrations on tool tip trajectory is clearly visible as peaks at the specified frequencies (10, 30, and 50 Hz), meaning that the low inertia of the designed micro-forceps module allows resonating the tip at high frequencies accurately within Micron's 1N force capability. The common traits between the tip position and the tip force spectra in all cases indicate a rigid connection between the tool tip and the bandage layer provided by strong grasping of forceps, even when the tip is resonating at 50 Hz.

The mean peeling force and speed for each set is displayed in the table in FIG. 21. Within each set, consistent results were obtained as indicated by the low standard deviation values due to high repeatability of tests on this type of phantom. In all sets, the mean peeling force was maintained just below the set safety threshold (7.5 mN) while trying to maximize the peeling speed as required. The variance analysis showed no significant difference in peeling forces among the sets, meaning that the bandages were peeled off by exerting similar forces (around 7 mN) with the help of the auditory force feedback ($p=0.32$). However, there was a statistically significant difference among the means of peeling speed ($p<0.05$). Further analysis with Tukey's HSD revealed that the mean peeling speed significantly increased as higher frequency oscillations were introduced on the tool tip trajectory during delamination. The mean peeling speed was 0.1392 mm/s in freehand trials whereas upon pulsating the tip at 10, 30 and 50 Hz, it rose respectively to 0.1789, 0.2232 and 0.2809 mm/s. Thus, tremor cancellation combined with 50 Hz vibrations enabled significantly faster peeling as compared to all other sets ($p<0.05$), and thus provided easier delamination. There was no statistical difference in terms of peeling speed between the freehand trials and the trials with sole tremor cancellation ($p=0.21$).

Figure 20:
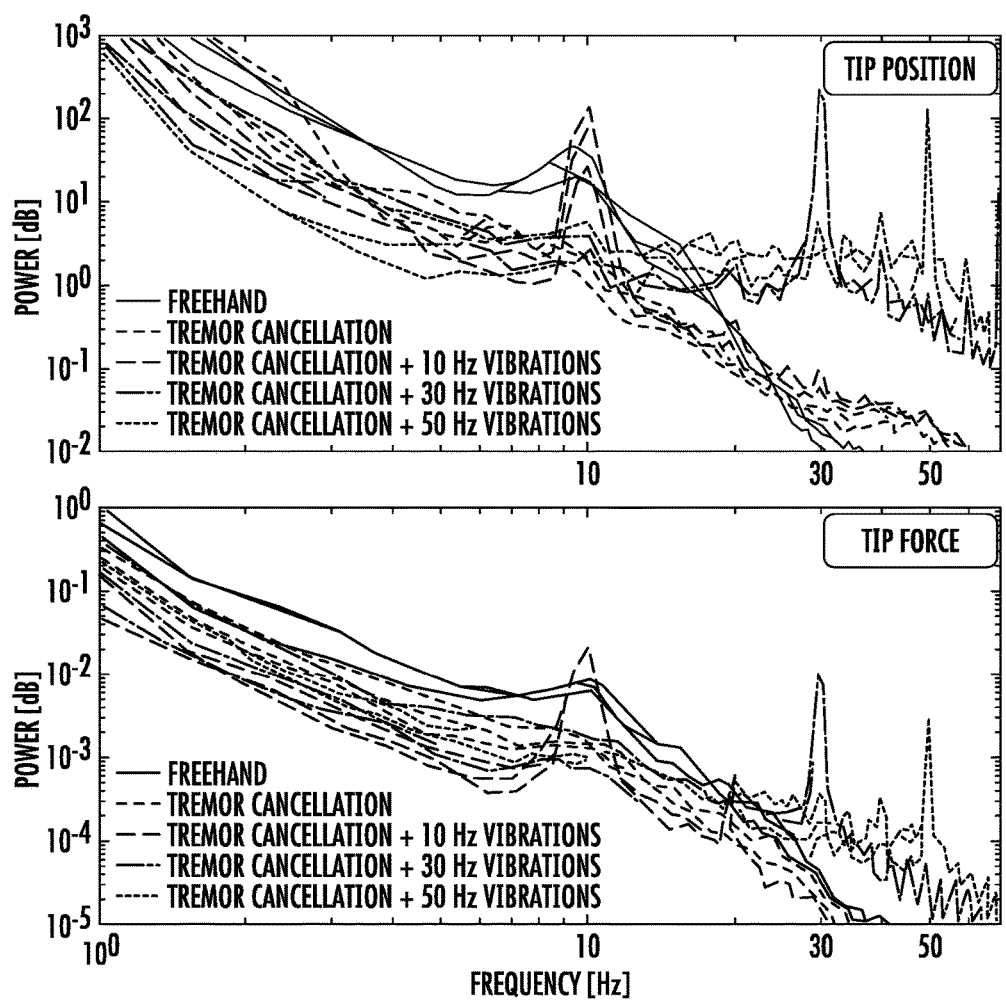
FIG. 20 shows power spectra of tip position and tip forces measure while peeling the inner shell membrane of raw chicken eggs (three trials per set are shown)

Power density spectra of the trials on chicken eggs is shown for three samples per case in FIG. 20. The trend for both the tip position and tip force are similar to those observed on the bandage phantom, though with slightly larger amplitude variation between the sets. The 10 Hz peak due to hand tremor is visible in freehand trials. By tremor cancellation, the oscillations in 2-20 Hz band were reduced by 45-90% and 5-85% respectively in the tip position and tip force spectra.

The common properties of the position and force spectra, and the prominence of 10, 30, and 50 Hz peaks in the trials using the new "controlled vibrations mode" strongly indicate that our micro-forceps is able to provide a rigid connection between the tool and the membrane being peeled also on this biological tissue, even when resonating the tip at high frequencies. Previously, when using a pick instrument instead of a micro-forceps [60], the slippage between the tool and the tissue was causing problems in manipulation of ISM, and such correlation between the tool tip dynamics and tool-to-tissue forces was not possible.

Peeling ISM of chicken eggs requires slightly larger forces than those for the bandage phantom. These forces are in fact a combination of tearing and delaminating forces in contrast to sole delaminating forces involved in bandage peeling. As shown in FIG. 21, in freehand trials, the recorded peeling forces averaged approximately 7.7 mN, which is slightly above the set threshold (7.5 mN). The corresponding mean peeling speed though is very slow (0.0868 mm/s). In these freehand trials, the user tried to stay below 7.5 mN threshold by peeling the membrane as slow as he could. This was however limited by the unintentional tool motion due to hand tremor. In addition, being a biological tissue, ISM exhibits slight variations in tissue properties within the same layer as well as between the eggs. Using ISM, it is harder to adjust peeling forces, since the exerted forces are not only related to tool tip speed, but also depend on local tissue properties. This behavior more closely simulates the real vitreoretinal practice. Due to these variations, the standard deviations in all sets were higher than those for the bandages.

The ANOVA analysis revealed that the difference in the mean peeling force among groups is not statistically significant (p=0.47). However, similar to the results for bandages, the tested cases significantly differ in terms of average peeling speed (p<0.05). Based on Tukey's HSD, controlled micro-vibrations of the tool tip provided ease in peeling, enabling faster delamination at the same force level. The mean peeling speed was 0.0868 mm/s in freehand trials whereas upon pulsating the tip at 10, 30, and 50 Hz, it rose respectively to 0.1416, 0.1850, and 0.2948 mm/s. The difference between freehand trials and trials with sole tremor cancellation was not statistically significant (p=0.20).

The designed micro-forceps module enables easy replacement of the disposable grasper jaws for better surgical performance in prolonged use, and for accommodating various jaw profiles for wider range of applications. FBGs located on the tool shaft sense the forces at the tool tip with a resolution of 0.3 mN. The mechanically decoupled design of the tip module from the handle mechanism, and its low inertia (1.9 g) ensure no adverse effect upon Micron's tremor canceling performance, and make high frequency micro-vibrations possible within the force limits of Micron. This design also provides flexibility in implementation: both the tip module and handle mechanism are not specific to Micron, and can easily be integrated with other handheld micromanipulators.

Experiments on bandages and raw chicken eggs have revealed that controlled micro-vibrations provide ease in delaminating membranes. Applying similar amount of forces, much faster delamination was observed when the frequency of these vibrations were increased (up to 50 Hz) while keeping the amplitude fixed (at 100 μm).

REFERENCES

1. P. S. Schenker, E. C. Barlow, C. D. Boswell, H. Das, S. Lee, T. R. Ohm, E. D. Paljug, G. Rodriguez, and S. T. Charles, "Development of a telemanipulator for dexterity enhanced microsurgery," in *Proc. 2$^{nd}$ Int Symp Med Rob Comput Asst Surg*, 1995, pp. 81-88.
2. I. W. Hunter, L. A. Jones, M. A. Sagar, S. R. Lafontaine, and P. J. Hunter, "Opthalmic microsurgical robot and associated virtual environment," *Comput Biol Med*, vol. 25:2, pp. 173-182, March 1995.
3. T. Ueta, Y. Yamaguchi, Y. Shirakawa, T. Nakano, R. Ideta, Y. Noda, A. Morita, R. Mochizuki, N. Sugita, M. Mituishi, and Y. Tamaki, "Robot-assisted vitreoretinal surgery: Development of a prototype and feasibility studies in an animal model," *Ophthalmology*, vol. 116:8, pp. 1538-1543, August 2009.
4. H. Das, H. Zak, J. Johnson, J. Crouch, and D. Frambach, "Evaluation of a telerobotic system to assist surgeons in microsurgery," *Comput Aided Surg*, vol. 4:1, pp. 15-25, 1999.
5. P. S. Jensen, K. W. Grace, R. Attariwala, J. E. Colgate, and M. R. Glucksberg, "Toward robot-assisted vascular microsurgery in the retina," *Graefes Arch Clin Exp Ophthalmol*, vol. 235:11, pp. 696-701, November 1997.
6. A. P. Mulgaonkar, J. P. Hubschman, J. L. Bourges, B. L. Jordan, C. Cham, J. T. Wilson, T. C. Tsao, and M. O. Culjat, "A prototype surgical manipulator for robotic intraocular micro surgery," *Stud Health Technol Inform*, vol. 142, pp. 215-217, 2009.
7. A. Uneri, M. A. Balicki, J. Handa, P. Gehlbach, R. H. Taylor, and I. Iordachita, "New steady-hand Eye Robot with micro-force sensing for vitreoretinal surgery," in *Proc. 3$^{rd}$ IEEE RAS EMBS Int Conf Biomed Robot Biomechatron (BioRob)*, 2010, pp. 814-819.
8. R. A. MacLachlan, B. C. Becker, J. Cuevas Tabarés, G. W. Podnar, L. A. Lobes, and C. N. Riviere, "Micron: an actively stabilized handheld tool for microsurgery," *IEEE Trans Robot*, vol. 28:1, pp. 195-212, February 2012.
9. W. T. Latt, U. X. Tan, C. Y. Shee, and W. T. Ang, "A compact handheld active physiological tremor compensation instrument," in *Proc. IEEE/Amer. Soc. Mech. Eng. Int. Conf. Adv. Intell. Mechatronics*, 2009, pp. 711-716.
10. C. J. Payne, K. Kwok, and G. Yang, "An ungrounded hand-held surgical device incorporating active constraints with force-feedback," in *Proc. IEEE Int. Conf on Intelligent Robots and Systems (IROS '13)*, 2013, pp. 2559-2565.
11. D. Chang, G. M. Gu, and J. Kim, "Design of a novel tremor suppression device using a linear delta manipulator for micromanipulation," in *Proc. IEEE Int. Conf on Intelligent Robots and Systems (IROS '13)*, 2013, pp. 413-418.
12. A. Saxena and R. V. Patel, "An active handheld device for compensation of physiological tremor using an ionic polymer metallic composite actuator," in *Proc. IEEE Int. Conf on Intelligent Robots and Systems (IROS '13)*, 2013, pp. 4275-4280.
13. B. Gonenc, E. Feldman, P. Gehlbach, J. Handa, R. H. Taylor, and I. Iordachita, "Towards Robot-Assisted Vitreoretinal Surgery: Force-Sensing Micro-Forceps Integrated with a Handheld Micromanipulator," in *IEEE Int. Conf on Robotics and Automation (ICRA '14)*, 2014, accepted.
14. J. Damadian, "Method of conducting a needle biopsy procedure," U.S. Pat. No. 6,702,761, Mar. 6, 2001.
15. Z. Sun, M. Balicki, J. Kang, J. Handa, R. Taylor, and I. Iordachita, "Development and preliminary data of novel integrated optical micro-force sensing tools for retinal microsurgery," in *Proc. IEEE Int. Conf on Robotics and Automation (ICRA '09)*, 2009, pp. 1897-1902.
16. I. Iordachita, Z. Sun, M. Balicki, J. Kang, S. Phee, J. Handa, P. Gehlbach, and R. Taylor, "A sub-millimetric, 0.25 mn resolution fully integrated fiber-optic force-sensing tool for retinal microsurgery," *International Journal of Computer Assisted Radiology and Surgery*, vol. 4, pp. 383-390, June 2009.
17. M. Balicki, A. Uneri, I. Iordachita, J. Handa, P. Gehlbach, and R. Taylor, "Micro-force Sensing in Robot Assisted Membrane Peeling for Vitreoretinal Surgery," *Med Image Comput Assist Interv.*, 2010, pp. 303-310.
18. B. Gonenc, M. A. Balicki, J. Handa, P. Gehlbach, C. N. Riviere, R. H. Taylor, and I. Iordachita, "Preliminary Evaluation of a Micro-Force Sensing Handheld Robot for Vitreoretinal Surgery," in *Proc. IEEE Int. Conf on Intelligent Robots and Systems (IROS '12)*, 2012, pp. 4125-4130.
19. S. Charles, "Techniques and tools for dissection of epiretinal membranes," *Graefe's Archive for Clinical and Experimental Ophthalmology*, vol. 241:5, pp. 347-352, May 2003.
20. X. He, M. A. Balicki, J. U. Kang, P. L. Gehlbach, J. T. Handa, R. H. Taylor, and I. I. Iordachita, "Force sensing micro-forceps with integrated fiber bragg grating for vitreoretinal surgery," in *Proc. of SPIE*, vol. 8218, pp. 82180W 1-7, February 2012.

21. I. Kuru, B. Gonenc, M. Balicki, J. Handa, P. Gehlbach, R. H. Taylor, and I. Iordachita, "Force Sensing Micro-Forceps for Robot Assisted Retinal Surgery," in *Proc. International Conference of the IEEE EMBS (EMBC '12)*, 2012, pp. 1401-1404.
22. R. J. Elble and J. E. Randall, "Mechanistic Components of Normal Hand Tremor," *Electroencephalography and Clinical Neurophysiology*, vol. 44:1, pp. 72-82, January 1978.
23. B. Gonenc, J. Handa, P. Gehlbach, R. H. Taylor, and I. Iordachita, "A Comparative Study for Robot Assisted Vitreoretinal Surgery: Micron vs. the Steady-Hand Robot," in *Proc. IEEE Int. Conf on Robotics and Automation (ICRA '13)*, 2013, pp. 4832-4837.
24. F. Peer, "Instrument for compensating hand tremor during the manipulation of fine structures," U.S. Pat. No. 6,238,384, May 29, 2001.

Example 2—Toward Robot-Assisted Vitreoretinal Surgery

Retinal microsurgery ranks among the most challenging areas of surgical practice, requiring the manipulation of extremely delicate tissues by various micron scale maneuvers and the application of very small forces. Focusing on the lack of force feedback, a family of force-sensing instruments was developed at JHU using fiber Bragg grating (FBG) strain sensors to measure the forces directly at the tool tip. Tool development continued with a manual pair of 2-DOF force-sensing forceps [1], followed by a 2-DOF forceps that can be used with the Steady-Hand Robot [2]. These can sense only the transverse tool-to-tissue interaction forces, which is a limitation for practical use in membrane peeling. For this reason, the design concept of a 3-DOF force-sensing forceps compatible with the Steady-Hand Robot was proposed, but is challenged by the available fabrication techniques [3].

Integrating the developed force-sensing tools with the Steady-Hand Robot and Micron forms two distinctly different assistive systems that can address both tremor and force limitation problems in membrane peeling. In our recent comparison study [4], we evaluated membrane peeling performance using these systems with the latest available force-sensing tool for each manipulator: a 2-DOF forceps for the Steady-Hand Robot, and a 2-DOF pick for Micron. Results showed that Micron performance was significantly challenged by the lack of a forceps tool for this system. Using the micro-forceps with the Steady-Hand Robot has revealed superior performance, as one can hold the tissue firmly and manipulate it more easily without slippage. In order to improve Micron's performance in this task and to make a fair comparison between the two assistive systems, it is crucial to have a compact lightweight force-sensing forceps module. In comparison to a manual or Steady-Hand Robot compatible forceps, this presents a completely different design problem with much stricter constraints.

In this paper, we report a new integrated assistive system for membrane peeling, combining an active tremor-canceling handheld micromanipulator with a force-sensing motorized micro-forceps. We will first present the design and calibration of our new force-sensing tool. This will be followed by system integration steps and the results of peeling experiments on a bandage phantom.

Figures 23A, 23B, 23C:
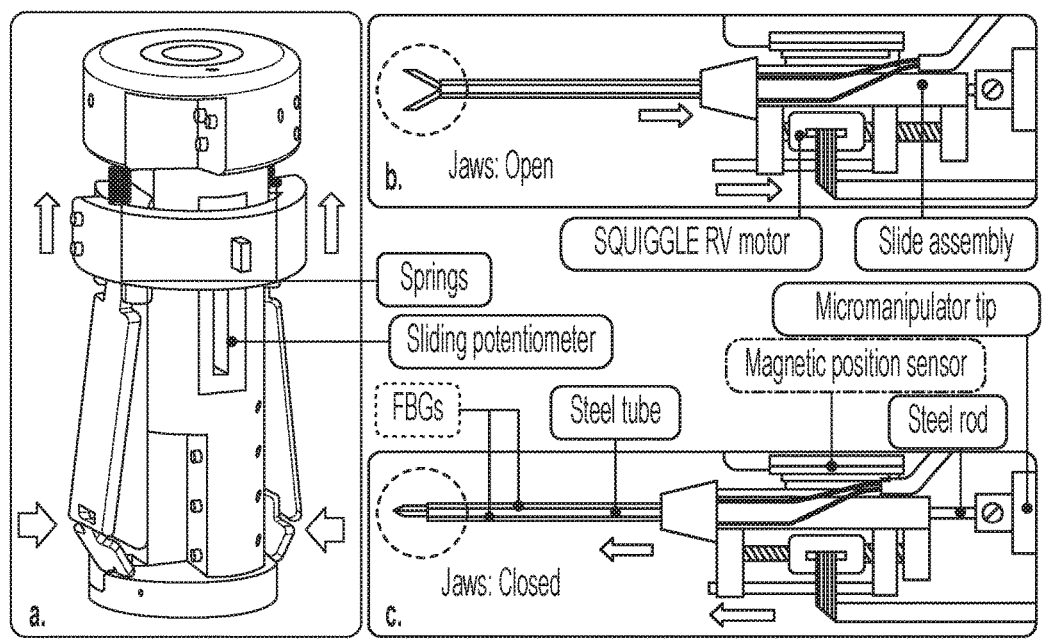
FIG. 23A shows the handheld mechanism for handheld micromanipulators.
FIG. 23B shows the motorized force-sensing tip with jaws open.
FIG. 23C shows the motorized force-sensing tip with jaws closed.

A motorized force-sensing micro-forceps integrated with a handheld micromanipulator (Micron) is shown in FIG. 22. A 2-DOF force-sensing micro-forceps for the Steady Hand Robot [2] is shown in the middle of the right-hand panel of FIG. 22. An original 23GA disposable forceps (Alcon, USA) is shown on the right side of the right-hand panel of FIG. 22. The design of the force-sensing micro-forceps includes two main parts: the handle mechanism (FIG. 23A), and the motorized force-sensing tip (FIGS. 23B and 23C).

For the handle mechanism, it is desirable to preserve the intuitive actuation mechanism on the existing disposable forceps from Alcon, Inc. (Fort Worth, Tex.), which was also used in our previous force-sensing micro-forceps for the Steady-Hand Robot [2]. This mechanism can be actuated simply by squeezing the tool handle. The squeezing motion causes the tube forming the tool shaft to slide in the distal direction to close the graspers. In our case, however, such rigid coupling between handle motion and tip actuation is not possible, since it would significantly interfere with the handheld micromanipulator's actuators. Instead of such a mechanical coupling, we used a sliding potentiometer on the handle to assess forceps closure. The sides of the handle mechanism are normally kept propped open by two springs as shown in FIG. 23A. Compressing the sides causes the sliders to move up along the tool handle (see the video attachment), inducing a voltage change in the potentiometer output. With the help of set screws, this mechanism can clamp onto any cylindrical manipulator handpiece up to 25 mm in diameter, transforming it into a micro-forceps handle.

In designing the motorized force-sensing tip, three main challenges needed to be overcome: (1) integrating force sensing capabilities while preserving the grasping motion of forceps, (2) avoiding interference between the manipulator's own actuation and the opening/closing action of the forceps, and (3) generating a self-standing universal module for compatibility with various handheld manipulators. This requires a very compact and lightweight micro-forceps module that can be actuated independently of the attachment site on the micromanipulator, and that carries all the force-sensing elements on it. Under these constraints we designed our "drop-in" micro-forceps as shown in FIGS. 23B and 23C.

In this concept, the forceps jaws are normally open, and are rigidly attached to the proximal end of the module by a steel rod. This rod lies along the whole tool, initially passing through a 23 gauge (Ga) steel tube in the distal end, and then through the sliding assembly in the proximal end. The 23 Ga stainless steel tube is rigidly attached to the slide assembly. For actuation, a linear micro motor, Squiggle-RV-1.8 by New Scale Technologies Inc., was selected due to its small size (2.8×2.8×6 mm), light weight (0.16 grams), precision (0.5 µm resolution), and high force (up to 0.33 N). The shaft of the motor is housed by the slide assembly at both ends to move it back and forth along the steel rod for opening and closing the forceps jaws (see the video attachment). This requires a travel distance of 1.2 mm, which is well below the motor's limit (6 mm). The position is tracked via the NSE-5310 magnetic position sensor located on the side of the slide assembly for closed-loop control. To integrate force sensing capabilities, FBG strain sensors (Smart Fibers, UK) were preferred mainly due to their small dimension, high sensitivity, biocompatibility, sterilizability, and immunity from electrostatic and electromagnetic noise. Following the fabrication method presented in [5], three FBGs were fixed on the 23 Ga tubular tool shaft axis symmetrically using medical epoxy adhesive. In order to monitor the FBGs, an optical sensing interrogator, sm130-700 from Micron Optics Inc. (Atlanta Ga.), was used. The outer diameter of the finalized tool shaft is approximately 0.9 mm, and is small enough to fit through a 20 Ga trocar. The module weighs less than 2 grams.

The calibration setup and protocol of the new micro-forceps module follow [5]. A linear reproducible behavior was observed for all FBGs during both the x- and y-axis calibration procedures, as shown in FIG. 24.

Figure 24:
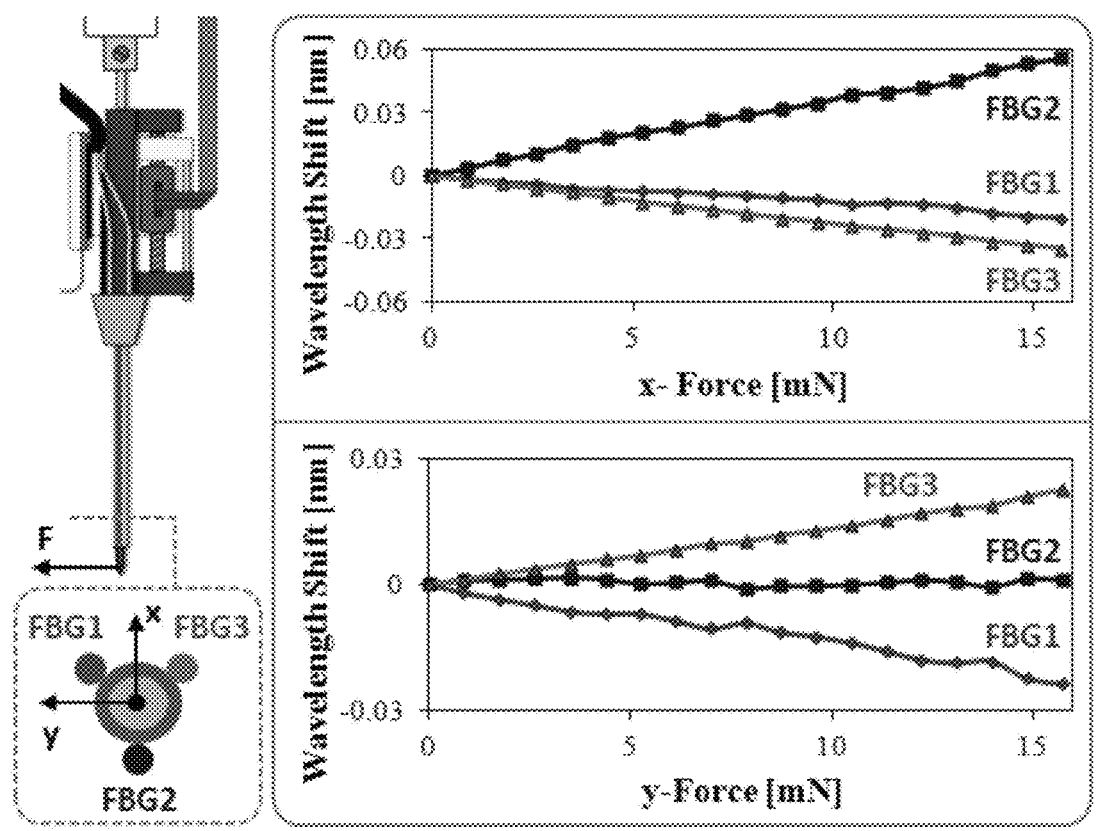
FIG. 24 shows calibration results in the x-axis direction (upper) and in the y-axis direction (lower)

Based on the results in FIG. 24, the following calibration matrix was determined:

$$K = \begin{bmatrix} 0.01084 & 0.01394 \\ -0.03276 & 0.00016 \\ 0.02192 & -0.01410 \end{bmatrix}$$

To compute the tip forces (F) from FBG wavelength shift ($\Delta S$), the pseudo-inverse of the obtained calibration matrix ($K^+$) is used in the linear relationship given by (2.1). This algorithm was previously shown to effectively remove the influence of ambient temperature [5].

$$F = K^+ \Delta S \tag{2.1}$$

The steel tube forming the tool shaft in our design is not only a functional element that provides the grasping action, but is also a structural element that carries the force-sensing FBGs. As the grasper jaws are squeezed and released, various external loads and frictional forces are induced on this tube. FBGs sense a combination of these inner actuation forces and the tip forces. The result is a repeated and consistent shift in force readings as the forceps is closed and opened even when there is no loading on the tip. This is highly undesirable as the maximum amount of shift (around 1 mN for each transverse force as in FIG. 25) is comparable to the amplitude of most forces during vitreoretinal practice (routinely below 7.5 mN).

Figure 25:
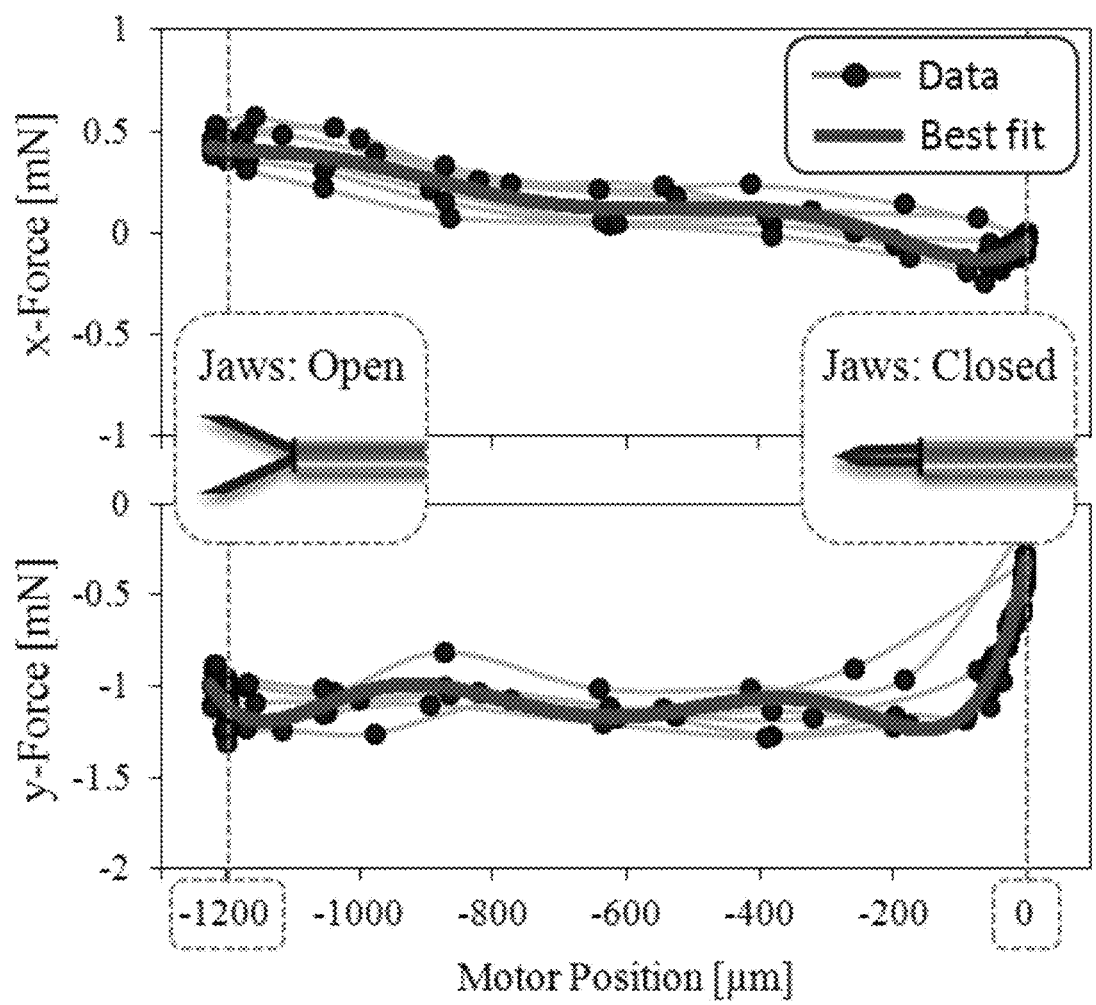
FIG. 25 shows measured forces versus motor position when no external force is applied on the forceps tip.
Figure 26:
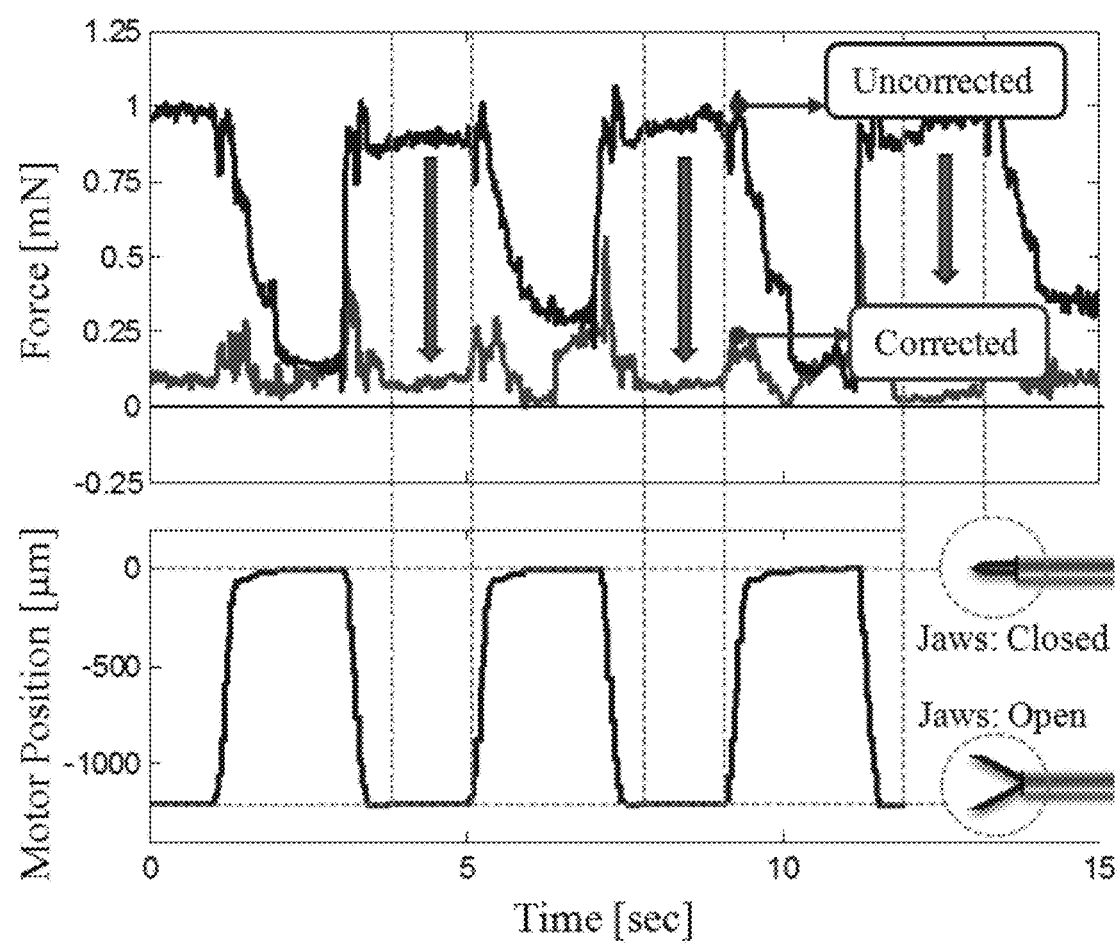
FIG. 26 shows consistent cycles of shift in force as the forceps is opened and closed repeatedly.

In order to model and compensate for this effect, we recorded the force variation with no force applied to the tip during three consecutive opening-closing cycles, which resulted in the mapping shown in FIG. 25. Due to grasper jaw geometry, material properties, and the frictional forces between the steel tube and forceps jaws, the behavior in FIG. 25 is highly nonlinear, yet consistent. This mapping relates the actuation forces to the motor position within ±0.15 mN. Based on the identified best fit and sensed motor position, the induced forces due to actuation can be estimated and subtracted from the measured values to obtain a corrected force reading. This provides a significant reduction in force variation as the forceps is closed and opened repeatedly. FIG. 26 shows cycles of shift in force as the forceps are opened and closed. As shown in FIG. 26, without such correction, the maximum force change is around 1 mN while the correction reduces it to 0.3 mN. This indicates that our tool is able to measure the forces in any direction in the xy-plane with an accuracy of 0.3 mN.

In order to form a complete assistive system for membrane peeling, the elements of the motorized force-sensing micro-forceps were integrated with a handheld micromanipulator, Micron. This device is able to cancel physiological hand tremor by activating three piezoelectric actuators. The position of its handle is determined by ASAP optical sensors [6]. After sensing the tool motion, Micron separates it into voluntary and tremulous components. Then Micron moves its tip to counteract the involuntary motion component within a workspace of approximately a 1×1×0.5 min volume centered on the handle position. The control software for tremor cancellation was implemented in LabVIEW as shown in FIG. 27.

The designed motorized micro-forceps module was mounted on the micromanipulator tip. Micron has about 1 N force capability, which is enough to support and move this additional load (smaller than 2 grams) quickly for effective tremor compensation. Hardware implementations were completed by clamping on the designed handle mechanism to transform the Micron handpiece into a forceps-handle. The control loop associated with the actuation of the forceps is shown in dashed lines in FIG. 27. Accordingly, analog position servo input is provided to the Squiggle motor controller via the sliding potentiometer on the handle mechanism. The magnetic sensor on the forceps tip provides position feedback to accomplish accurate closed loop control, opening or closing the grasper jaws without noticeable delay.

Figure 27:
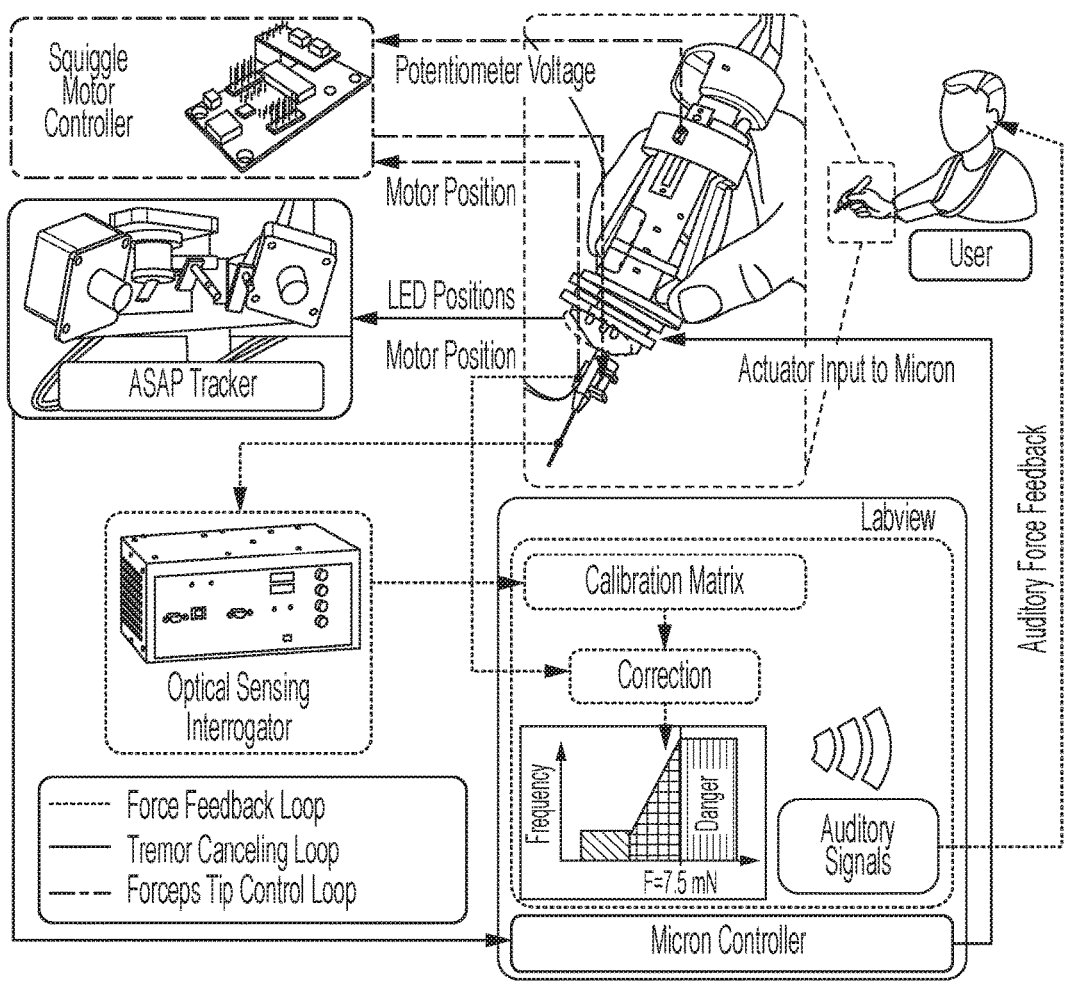
FIG. 27 shows the control scheme of the integrated system.

The existing LabVIEW control software was extended to include a force feedback loop as shown in dotted lines in FIG. 27. During operation, the wavelength information from each FBG channel is collected and processed at 1 kHz and transmitted over TCP/IP to the LabVIEW environment. Forces are then computed utilizing the calibration matrix. Based on forceps configuration (linear motor position), the computed force value is corrected to obtain tip forces. These tip forces are then converted into auditory signals. The frequency of these audio signals changes with the level of the applied force [7]. Depending on the frequency of the auditory feedback (AF), the user adjusts tool motion so that the applied forces do not exceed 7.5 mN, which we define as the danger zone threshold in membrane peeling based upon our prior in-vivo experience [1].

Figure 28:
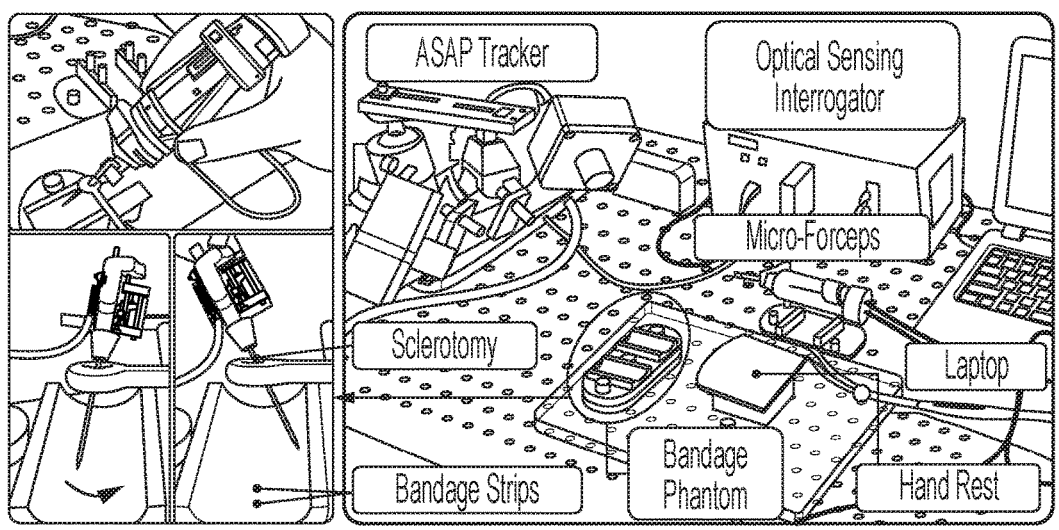
FIG. 28 shows the setup for membrane peeling experiments on bandage phantoms according to some embodiments of the invention.

In order to assess the performance of the developed system, several peeling trials were performed by a single non-surgeon subject on the setup shown in FIG. 28. As a surrogate for epiretinal membrane, 2 mm wide strips were cut from 19 mm Clear Bandages (RiteAid brand), which have previously been reported and used in our laboratory for similar tests [4, 7]. The bandage strips were attached to a plastic base with curvature (Ø 25 mm) resembling the back of the eye. In addition, a rubber sclerotomy constraint was located directly above the bandage strips.

During the experiment, the subject was asked to (1) insert the micro-forceps tool through the sclerotomy point, (2) grasp and lift the bandage edge, and (3) peel the strip off of the plastic surface while keeping the tool velocity as uniform as possible (~0.5 mm/s) and the delaminating forces below the danger threshold (~7.5 mN) based on the provided auditory force feedback. The goal of the experiment is to identify any interference between the micro-forceps and Micron operation, and to determine whether the implemented hardware modifications affect the device's tremor canceling characteristics. For this reason, the experiments were done in two sets by turning the tremor cancellation feature on and off. Five peels were recorded per category, and the tests were performed in alternating order. Before data collection, an extensive training period (~1 hrs) was allowed for the subject to become accustomed to the system and phantom, and to minimize learning curve effects in the recorded measurements. During data collection, the tool tip force and position and the Squiggle motor position were recorded. Based upon the Squiggle motor position, the starting and ending points of the delamination were identified in the acquired data. The assessment was based on the applied forces and tool tip positions during this period.

Figure 29:
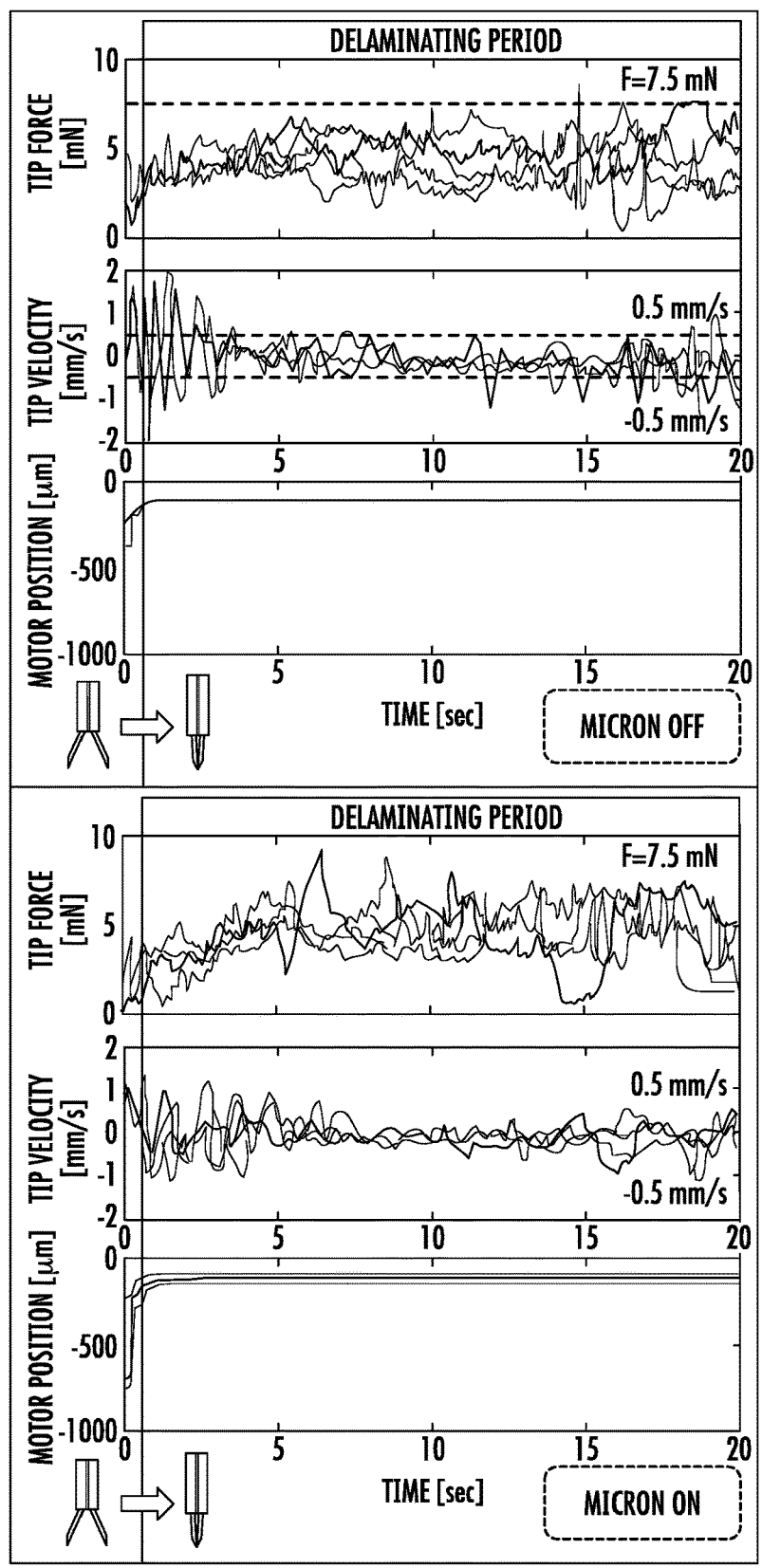
FIG. 29 shows measured peeling forces using a bandage phantom for all trials (5 trials/case)

Measured forces on the bandage phantom are displayed for all trials in FIG. 29. The starting time of the task is set at the point when the user starts closing the grasper jaws. The delaminating period begins after the forceps are closed, and the forces after this time are of interest. During the delaminating period, the exerted forces in all trials remained below the safety threshold (7.5 mN), which displays the effectiveness of the auditory force feedback and agrees with our previous results [4, 8]. On the other hand, high frequency oscillations were visible when the tremor suppression feature of the system was not used. Upon activation of Micron, these oscillations were significantly reduced.

Figure 30:
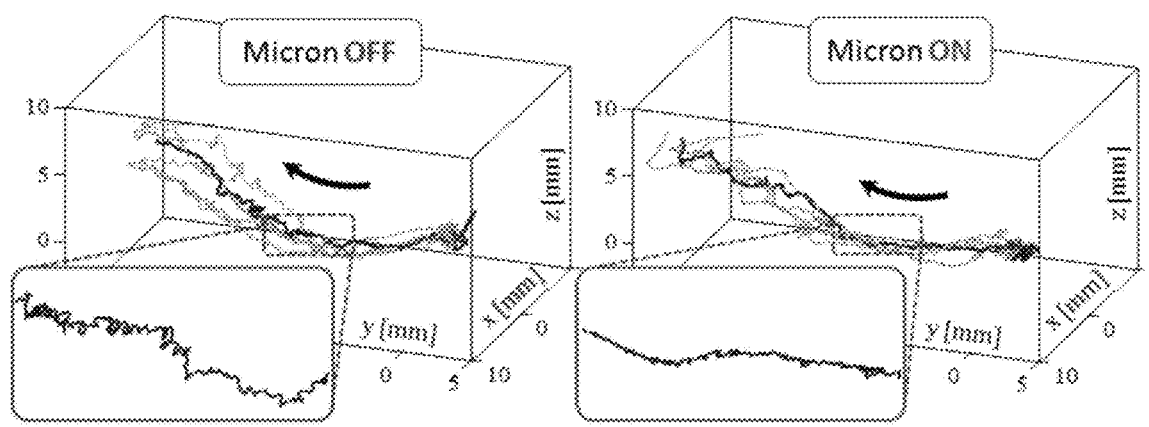
FIG. 30 shows the tool tip trajectory during the delamination period, with the arrow indicating the peeling direction.

The effect of physiological hand tremor is also visible in velocity and tip position plots. The tip position trajectory is shown in FIG. 30. In all trials, the user managed to keep the peeling speed around 0.5 mm/s as desired; however, oscillations and difficulty increased in the absence of Micron tremor aid. FIG. 30 shows that the tool tip in Micron-assisted trials followed a much smoother trajectory with higher positioning accuracy in comparison to the cases without tremor cancellation.

Figure 31:
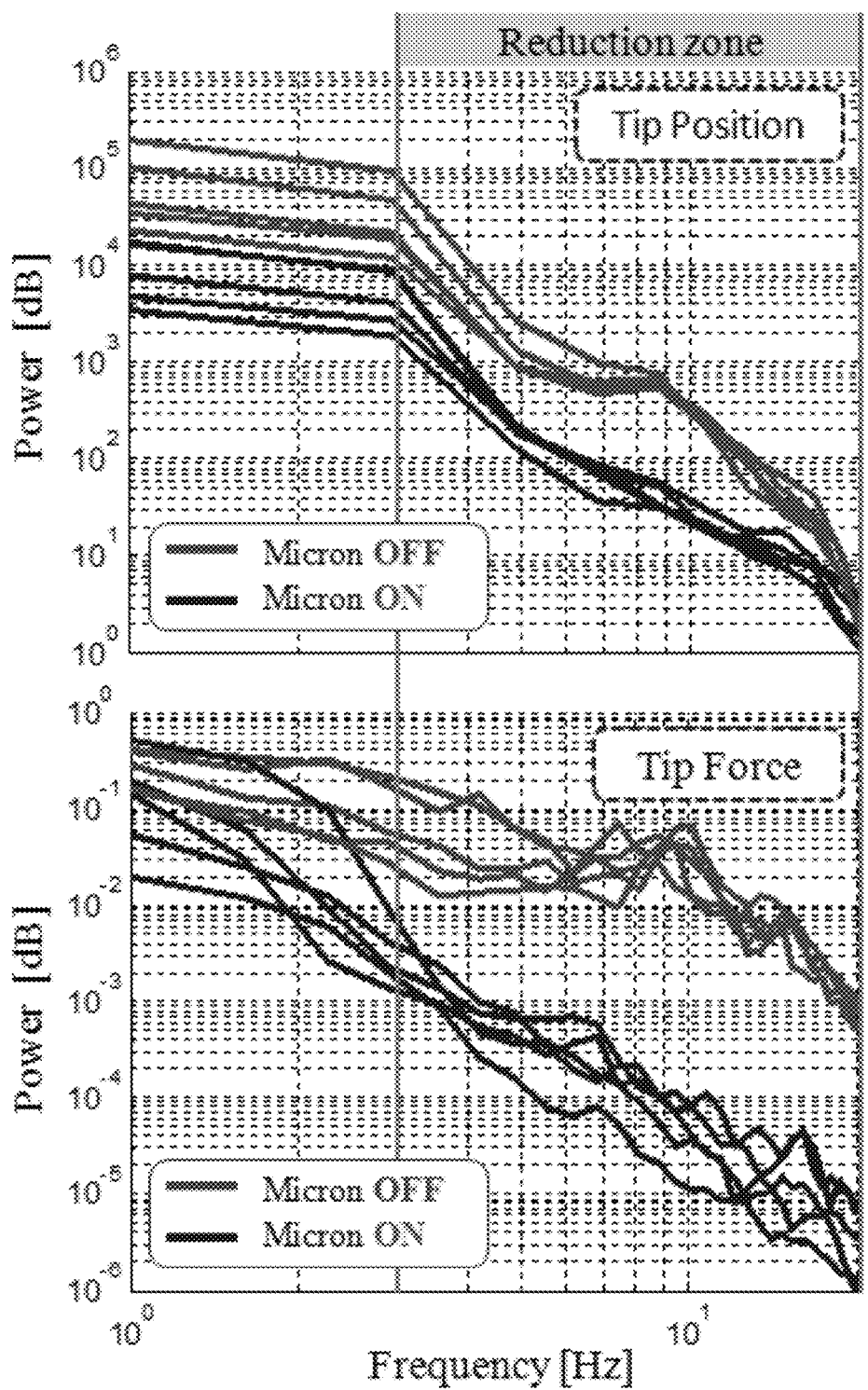
FIG. 31 displays a frequency analysis of tip position and peeling forces.

In order to assess the tremor canceling effect of Micron in our tests, we performed frequency analyses based on both position and force measurements. The results are presented in FIG. 31. The bandwidth of human hand-eye feedback usually is from 0.5 Hz to 2 Hz [9]. Below 0.5 Hz, hand-eye feedback becomes effective. Thus, the regions below 0.5 Hz in these figures represent controlled actions, whereas frequencies above 2 Hz indicate the unintentional motion of the user. The postural hand tremor frequency in normal humans is approximately 8-10 Hz [9]. The prominence of a peak around 9 Hz in Micron-off trials is primarily due to the subject's hand tremor. When the tremor suppression feature is activated, this peak is eliminated and the high-frequency components (2-20 Hz) are overall reduced by 60-95% in both the tip force and tip position spectra.

The significant reduction in the 2-20 Hz band and percentages comparable to our previous results with Micron [4, 8] confirm that there is no adverse effect in tremor suppression characteristics due to the newly-introduced micro-forceps tip module. On the contrary, the forceps allow for grasping—and thus a more rigid connection between the tool tip and membrane—which now enables us to relate the characteristics of the measured forces to the tool tip dynamics. The common power spectral density traits in FIG. 30 strongly indicate this connection. Previously, when using the pick instrument, such direct comparison did not yield reliable results, especially during trials in biological phantoms such as chick embryos, due to slippage between the tool and the tissue [4]. Furthermore, with the new forceps tip, the user can accomplish the peeling task in a single attempt, whereas a pick instrument could necessitate multiple attempts due to associated challenges in tissue manipulation. This is not only important for ease of use, but also significantly increases safety, since multiple delamination attempts intensify the risk of retinal damage.

Described herein is an integrated assistive system for membrane peeling that combines an active tremor-canceling handheld micromanipulator, Micron, with a force-sensing motorized micro-forceps. Our system addresses two of the most critical requirements of vitreoretinal surgery: tremor-free tool motion and limitation of applied forces.

Herein, we first developed a compact, lightweight, force-sensing micro-forceps module with an intuitive handle mechanism. The tip was motorized so that there is no mechanical coupling required between the handle mechanism and the forceps tip. Three FBGs were incorporated onto the tip module to provide 2-DOF force sensing capability with a resolution of 0.3 mN. In order to form a complete system, the module was integrated onto Micron. Membrane peeling tests were performed on a bandage phantom to monitor performance and identify any advantages or disadvantages regarding the integration. Analyses revealed no adverse effect upon Micron's performance due to the added inertia of the forceps module. Compared to a pick instrument, the micro-forceps provided an easier and safer operation by facilitating better tissue manipulation and enabling peeling to be accomplished in a single attempt. In addition, the slippage problem in pick usage was eliminated. Consequently the measured tool-to-tissue forces and tool-tip dynamics were more highly correlated.

1. X. He, M. A. Balicki, J. U. Kang, P. L. Gehlbach, J. T. Handa, R. H. Taylor, and I. I. Iordachita, "Force sensing micro-forceps with integrated fiber bragg grating for vitreoretinal surgery," in *Proc. of SPIE*, vol. 8218, pp. 82180W 1-7, February 2012.
2. I. Kuru, B. Gonenc, M. Balicki, J. Handa, P. Gehlbach, R. H. Taylor, and I. Iordachita, "Force Sensing Micro-Forceps for Robot Assisted Retinal Surgery," in *Proc. International Conference of the IEEE EMBS (EMBC '12)*, 2012, pp. 1401-1404.
3. B. Gonenc, J. Handa, P. Gehlbach, R. H. Taylor, and I. Iordachita, "Design of 3-DOF Force Sensing Micro-Forceps for Robot Assisted Vitreoretinal Surgery," in *Proc. International Conference of the IEEE EMBS (EMBC '13)*, 2013, pp. 5686-5689.
4. B. Gonenc, J. Handa, P. Gehlbach, R. H. Taylor, and I. Iordachita, "A Comparative Study for Robot Assisted Vitreoretinal Surgery: Micron vs. the Steady-Hand Robot," in *Proc. IEEE Int. Conf on Robotics and Automation (ICRA '13)*, 2013, pp. 4832-4837.
5. I. Iordachita, Z. Sun, M. Balicki, J. Kang, S. Phee, J. Handa, P. Gehlbach, and R. Taylor, "A sub-millimetric, 0.25 mn resolution fully integrated fiber-optic force-sensing tool for retinal microsurgery," *International Journal of Computer Assisted Radiology and Surgery*, vol. 4, pp. 383-390, 2009.
6. R. A. MacLachlan, B. C. Becker, J. Cuevas Tabarés, G. W. Podnar, L. A. Lobes, and C. N. Riviere, "Micron: an actively stabilized handheld tool for microsurgery," *IEEE Trans Robot*, vol. 28:1, pp. 195-212, February 2012.
7. M. Balicki, A. Uneri, I. Iordachita, J. Handa, P. Gehlbach, and R. Taylor, "Micro-force Sensing in Robot Assisted Membrane Peeling for Vitreoretinal Surgery," *Med Image Comput Comput Assist Interv.*, vol. 13, pp. 303-310, 2010.
8. B. Gonenc, M. A. Balicki, J. Handa, P. Gehlbach, C. N. Riviere, R. H. Taylor, and I. Iordachita, "Preliminary Evaluation of a Micro-Force Sensing Handheld Robot for Vitreoretinal Surgery," in *Proc. IEEE Int. Conf on Intelligent Robots and Systems (IROS '12)*, 2012, pp. 4125-4130.
9. R. N. Stiles, "Mechanical and neural feedback factors in postural hand tremor of normal subjects," *J. Neurophysiol.*, vol. 44, pp. 40-59, July 1980.

Example 3—Effects of Micro-Vibratory Modulation During Robot-Assisted Membrane Peeling Several studies have explored the addition of haptic feedback and force feedback substitution to laparoscopic and robotic surgery, and have demonstrated better results with these methods. Similar studies focusing on microsurgery are few. In simulated ophthalmic procedures, auditory force feedback was shown to help in maintaining the exerted forces below potentially dangerous levels [1, 2]. In addition, there are motivating applications in other fields that may help in reducing forces, such as inserting a biopsy needle, where reciprocation of the needle was shown to facilitate the advance of the needle through tissue and penetration of the site of interest [3]. Recently, we have shown that inducing micro-vibrations on the tool tip can facilitate delamination of membranes as well [4]. However, deciding on the optimal frequency and amplitude of these vibrations during the surgical operation, and updating this information based on exerted forces in real time is not trivial.

Figure 32:
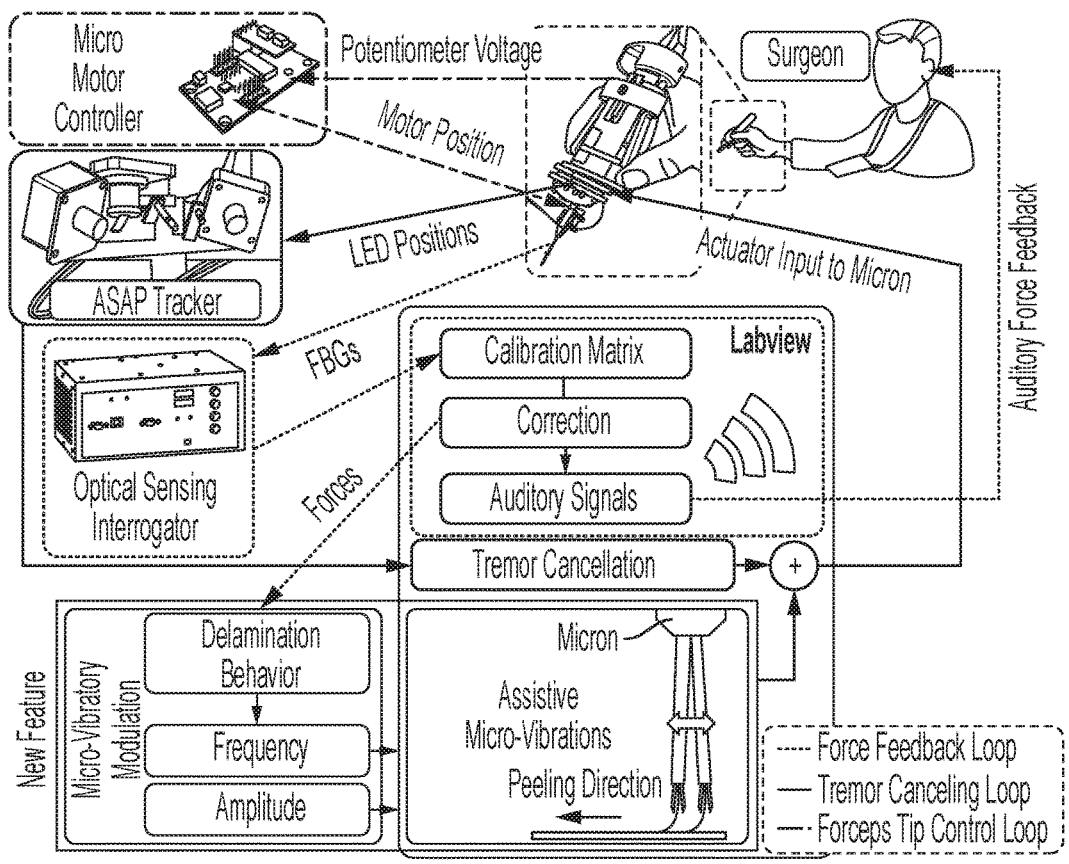
FIG. 32 shows a system overview, wherein a handheld micromanipulator is combined with a force-sensing microforceps with vibrations at the tool tip to assist membrane peeling.

We describe herein the effect of the main micro-vibration parameters on membrane peeling forces, and establish an adaptive control algorithm for regulating micro-vibrations during the procedure. FIG. 32 shows a system overview, wherein a handheld micromanipulator is combined with a force-sensing micro-forceps with vibrations at the tool tip to assist membrane peeling. We will first present the force-sensing micro-forceps system. This will be followed by the experimental investigation of micro-vibrations during membrane peeling on two types of phantoms: artificial bandages and raw chicken eggs.

In order to suppress involuntary hand motion, and induce assistive micro-vibrations during membrane peeling, our system uses a handheld micromanipulator: Micron [5]. This device is normally designed to cancel the physiological hand tremor of the surgeon. The position of its handle is determined by ASAP optical sensors. After sensing the tool motion, it is filtered into voluntary and tremulous components. Then activating its three piezoelectric actuators, Micron moves its tip to counteract the involuntary motion component within a workspace of approximately a 1×1×0.5 mm volume centered on the handle position. The control software for this operation mode was already implemented in LabVIEW. For our system, we extended the existing control loop by injecting controlled pulses to tool tip trajectory with variable frequency and amplitude (FIG. 32). In order to identify the individual effect of each parameter on delamination forces, these variables are currently set manually. But the ultimate aim is to develop an adaptive control law—based upon the delamination response to each parameter—that will tune the frequency and amplitude automatically according to measured tool-to-tissue forces.

Figures 33A, 33B:
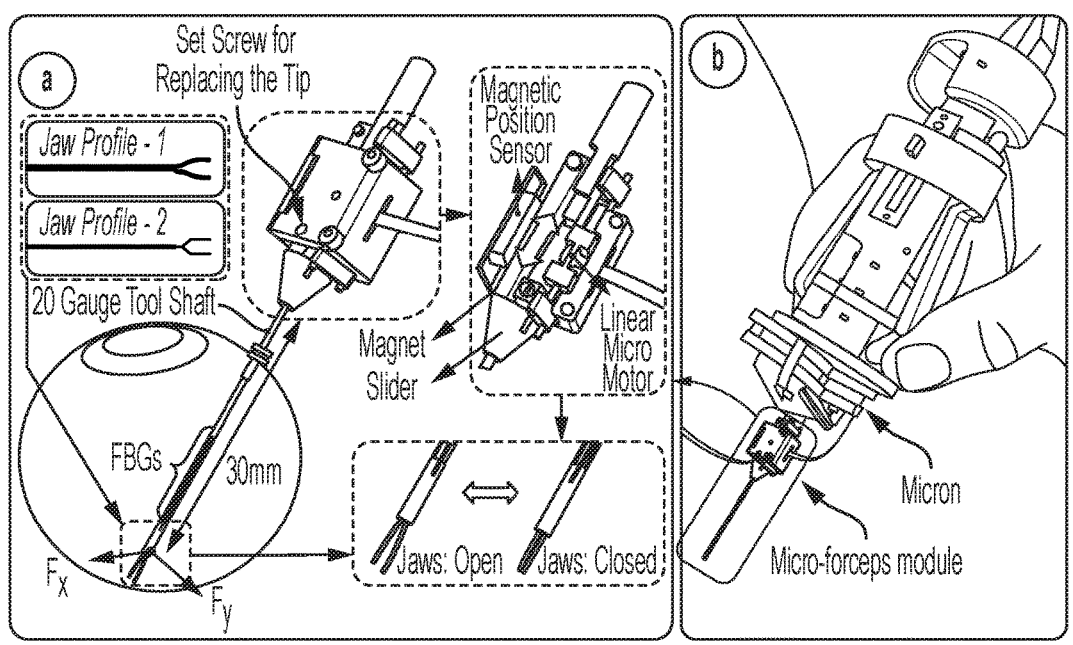
FIG. 33A shows the motorized force-sensing micro-forceps module [4]
FIG. 33B illustrates how the micro-forceps module is compatible with the handheld micromanipulator.

For accurate manipulation of the tissue, a firm grasping mechanism is necessary. In our previous work, we developed a motorized force-sensing micro-forceps module that fits onto Micron without interfering with its operation [4]. The unit is a "drop-in" module carrying all the necessary actuators and sensors, as shown in FIGS. 33A and 33B. The actuation is provided by a linear micro motor (Squiggle-RV-1.8 by New Scale Technologies Inc., Victor, N.Y.), which slides the tubular tool shaft up and down along the tool axis to respectively open and close the forceps jaws. This motion is tracked by the magnetic position sensor fixed on the side of the module base for accurate closure and opening despite the potentially variable friction around the tool shaft. The forceps jaws are fixed to the module body via a set screw, and can easily be replaced. This enables the use of various jaw profiles for handling various surgical tasks, such as the thicker profile-1 in FIG. 33A for peeling dense epiretinal membranes and the slimmer profile-2 for delamination of finer internal limiting membranes. In addition, since the forceps jaws can wear and deform with use, easy jaw replacement enables use in prolonged or repeated tests without deterioration of the grasping quality.

Figures 34A, 34B, 34C:
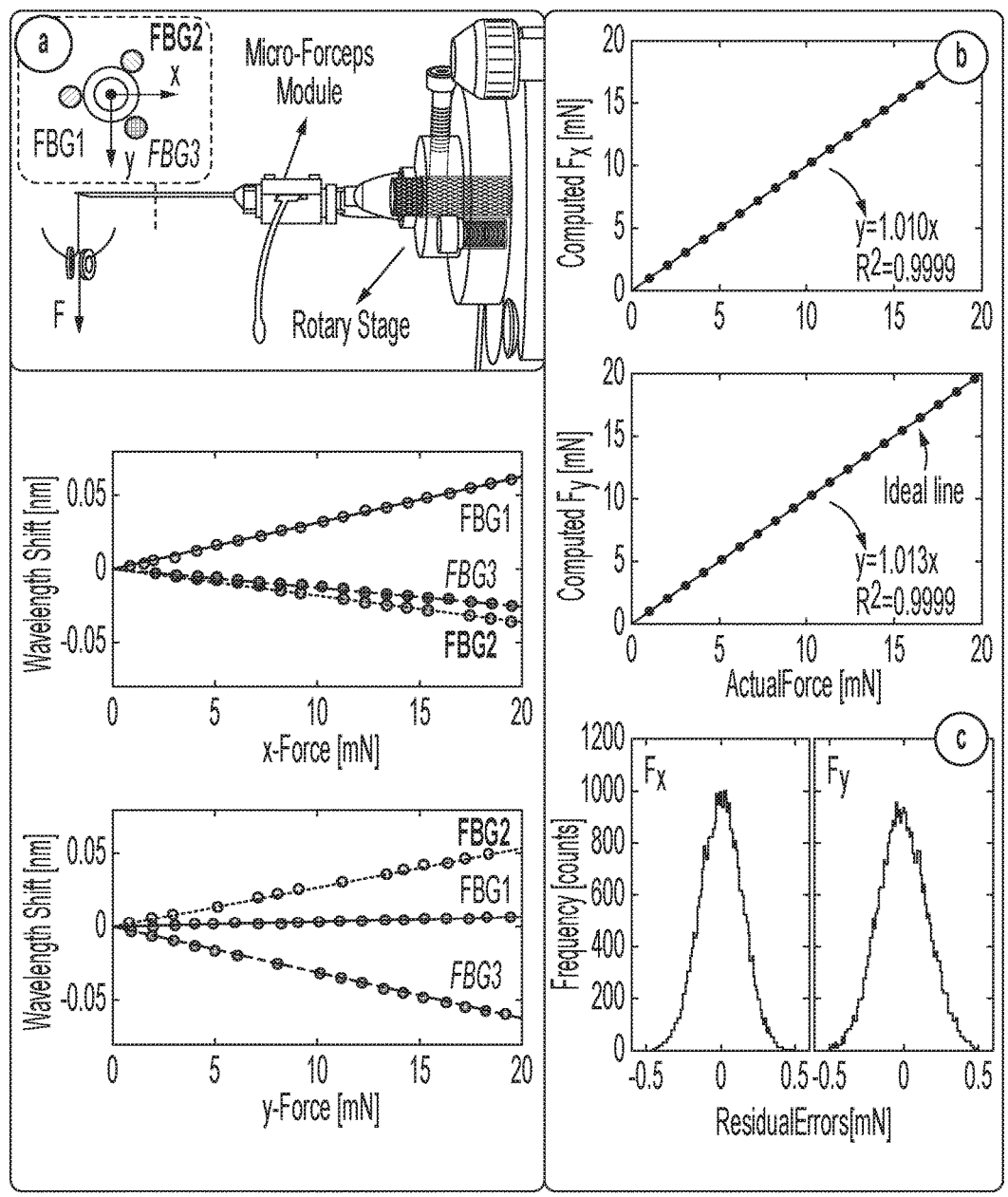
FIG. 34A shows calibration results for FBGs when the tip is loaded along the x and y axes.
FIG. 34B shows the computed forces versus the actual forces along the x and y axes.
FIG. 34C shows a histogram of the residual error.

The micro-forceps module is capable of sensing the transverse forces exerted at its tip via the three FBG strain sensors attached evenly around the tool shaft. The calibration setup and protocol of the force sensor follow [6]. The wavelength shift in each FBG sensor normally depends linearly on both the local strain and the temperature variation. During calibration, the effect of temperature change was removed by subtracting the mean wavelength shift from each sensor measurement. Resulting temperature-compensated sensor readings exhibit a linear reproducible behavior during both the x- and y-axis calibration procedures, as shown in FIG. 34A. The slopes of the response curves form the calibration matrix (K). The Moore-Penrose pseudo-inverse of this matrix ($K^+$) is used in the linear relationship (3.1) to compute the transverse tool tip forces ($F_x$ and $F_y$) from FBG wavelength shifts ($\Delta S$) during the operation.

$$\begin{bmatrix} F_x \\ F_y \end{bmatrix} = K^+ \cdot \Delta S \text{ where } K = \begin{bmatrix} 0.0031 & 0.0004 \\ -0.0018 & 0.0027 \\ -0.0013 & -0.0031 \end{bmatrix} \quad (3.1)$$

In order to monitor the FBGs, we use an optical sensing interrogator (sm130-700 from Micron Optics Inc., Atlanta, Ga.). The wavelength resolution of the interrogator is 1 pm. Based upon the obtained calibration matrix, this corresponds to a transverse force resolution of about 0.21 mN. To verify sensor operation, the tool tip was loaded and unloaded repeatedly in different angles (0°, 45° and 90°), and the computed forces were compared with the actual tip loading. Results showed consistency with the actual values for both $F_x$ and $F_y$, and a close fit to the ideal straight line (slope=1) passing through the origin (FIG. 34B). The root mean square error was 0.14 mN and 0.17 mN respectively for $F_x$ and $F_y$. The histogram of the residual errors in FIG. 34C shows that the probability of errors beyond 0.5 mN is very low.

Figures 35A, 35B:
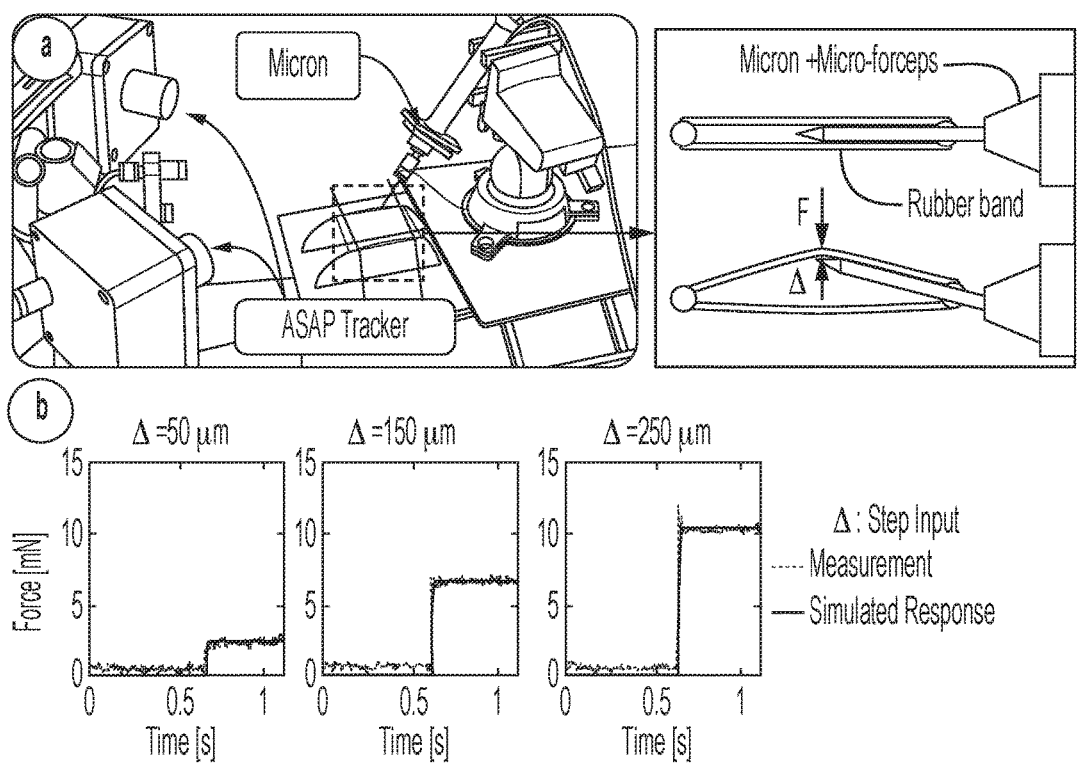
FIG. 35A shows the setup for monitoring the transient response of the force-sensing tip.
FIG. 35B shows the step response of the sensor.

Accurate measurement of membrane peeling forces in the presence of micro-vibrations requires not only sub-mN force-sensing resolution but also a very fast responding force sensor. The transient response of the force-sensing tip was monitored using the setup shown in FIG. 35A. First, the micro-forceps module was mounted onto Micron, and the forceps tip was held between two elastic rubber bands. Then, Micron was given a step input to move the tool tip towards one side laterally while the resulting reaction force was recorded. The tests were repeated for three levels of step amplitude (50, 150 and 250 µm). In all case, the measured force profile matched a first order system response with 0.005 s time constant as shown in FIG. 35B, proving a fast enough response to track rapid force variations even in the presence of high frequency micro-vibrations (in our case up to 50 Hz).

There are various factors affecting the forces in membrane peeling. Some of these pertain to tissue properties, such as tissue width and thickness, while some are related to the motion of the peeling instrument, such as the peeling speed. In order to isolate the influence of micro-vibrations, all other factors affecting the peeling force need to be eliminated in a very reproducible experimental setup. Using a handheld micromanipulator, it is hard to keep the peeling speed constant. To avoid peeling speed alterations during and between trials, we fixed the Micron handle to a clamp, and used a linear stage to drive phantoms relative to Micron (FIGS. 36A-36D). The micro-forceps module was attached onto Micron for grasping the phantom before peeling.

Figures 36A, 36B, 36C, 36D:
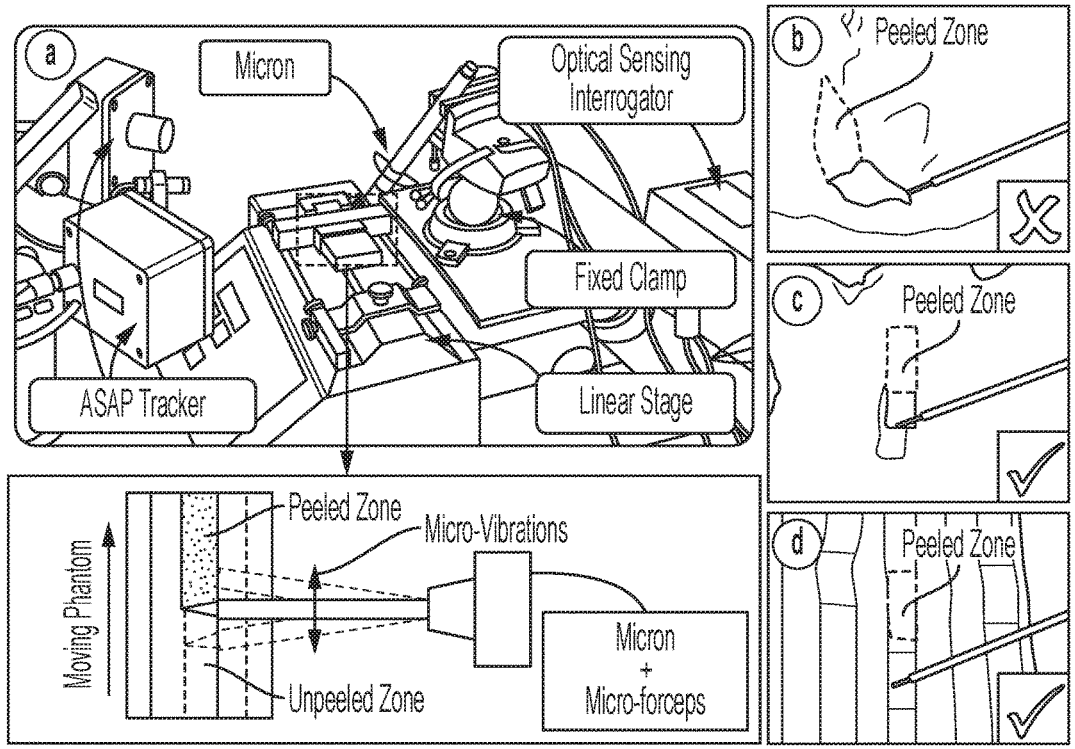
FIG. 36A shows the experimental setup with the phantoms moved on a linear stage.
FIG. 36B illustrates how peeling the inner shell membrane of the raw eggs produces triangular shaped strips, and requires both tearing and delaminating forces.
FIG. 36C illustrates how the effect of tearing forces and varying membrane width throughout delamination were avoided using sliced egg shell membranes.
FIG. 36D illustrates how the effect of tearing forces and varying membrane width throughout delamination were avoided using sliced bandages.

To simulate an epiretinal membrane, the inner shell membrane (ISM) of raw chicken eggs can normally be used. However, in this phantom, the membrane routinely comes off the egg shell creating a non-uniform triangular piece of membrane if a linear peeling trajectory is followed (FIG. 36B). The varying width of the peeled tissue significantly affects the forces, and the dimensions of this wedge shape varies between the phantoms. To peel consistent and constant width membrane strips, a helical trajectory needs to be followed. However, such dexterous motion is not possible using a linear stage. Furthermore, while peeling the ISM, the measured forces stem from two main sources: (1) the tearing force between the peeled section and the surrounding membrane; (2) the delaminating force due to the adhesion between the peeled section and the underlying shell. Of these components—for purposes of epiretinal and/or internal limiting membrane peeling—we believe the delaminating force is more critical, and needs to be reduced/limited as it is the force that is directly applied onto the delicate retinal surface. In order (1) to eliminate the tearing forces and focus purely on the delaminating forces, and (2) to fix the width of the peeled layers for consistency between trials, we used two different phantoms: sliced bandages and sliced shell membranes of raw chicken eggs.

Figure 37:
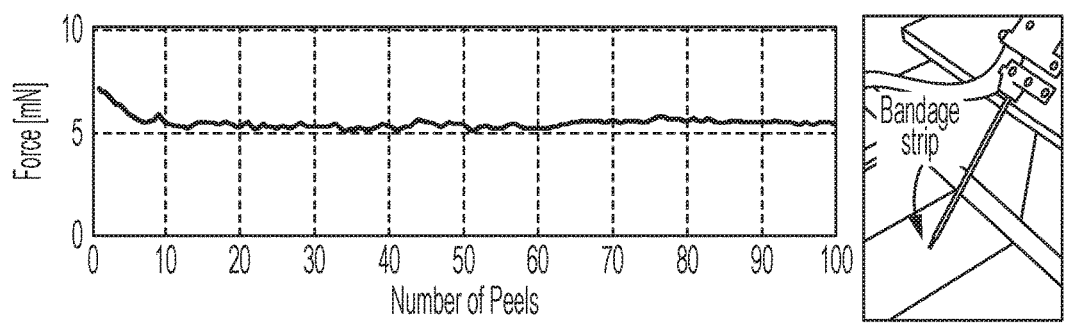
FIG. 37 shows force per peels for a single bandage strip that was peeled at a constant speed (0.15 mm/s) and brushed back on several times.

The bandage phantom was prepared by slicing sticky tabs from 19 mm Clear Bandages (Rite Aid Corp.) into 2 mm wide strips (FIG. 36D). Repeated peeling tests using a single bandage strip on the setup shown in FIG. 36A revealed that the adhesion between the bandage strip and its backing decays with each peel initially (FIG. 37). However, after approximately the 10th peel, the bandage sticks back on consistently, requiring similar amount of delamination force for a prolonged time. This enables the use of each strip numerous times by brushing it back in place with its consistent level of adhesion after each peel, and provides a very repeatable platform for conducting multiple tests.

The membrane inside the raw chicken egg shell was sliced similarly using a razor (FIG. 36C). Both the inner and the adherent outer shell membranes are cut together. Thus, while peeling the cut strips, both membranes need to be delaminated off the egg shell surface, which requires a larger force as compared to the removal of ISM alone. In contrast to the bandage phantom, each membrane strip can be used only once, limiting the total number of tests on this phantom. Yet, assuming that the membrane structure does not vary significantly between the eggs, this phantom provides a consistent platform for studying the effect of micro-vibrations on peeling biological tissue.

Peeling tests on the bandage phantom were done in two sets, each set having a different speed setting (0.15 mm/s and 0.3 mm/s). In each set, a total of ten operational modes were examined. In the first mode, delaminating forces during regular peeling were monitored. The remaining modes explored the effect of micro-vibrations at three frequencies (10, 30 and 50 Hz) and three amplitudes (50, 100 and 150 μm). Fifteen trials per mode were completed using a single bandage strip for each speed setting. Each bandage was peeled and brushed back ten times before starting the trials, so that the adhesion between the bandage and its backing remained consistent throughout the experiments (FIG. 37). For the egg trials, the experimental conditions were limited to one speed setting (0.15 mm/s), two frequencies (30 and 50 Hz) and two amplitudes (100 and 150 μm). Ten shell membrane strips were peeled for each setting, and each strip was used only once.

The experiments were conducted by alternating the order of experimental modes. Each strip was peeled continuously for a 60 second period. The measured tool tip force was acquired at 1 kHz. The average and maximum peeling force ($F_{average}$ and $F_{peak}$) for each mode were analyzed using one-way ANOVA followed by a t-test assuming unequal variance. Statistical significance was defined as $p<0.05$.

Figure 38:
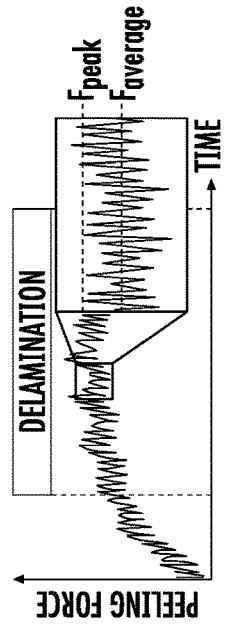
FIG. 38 shows the variation in delaminating forces with respect to micro-vibration frequency.
Figure 39A:
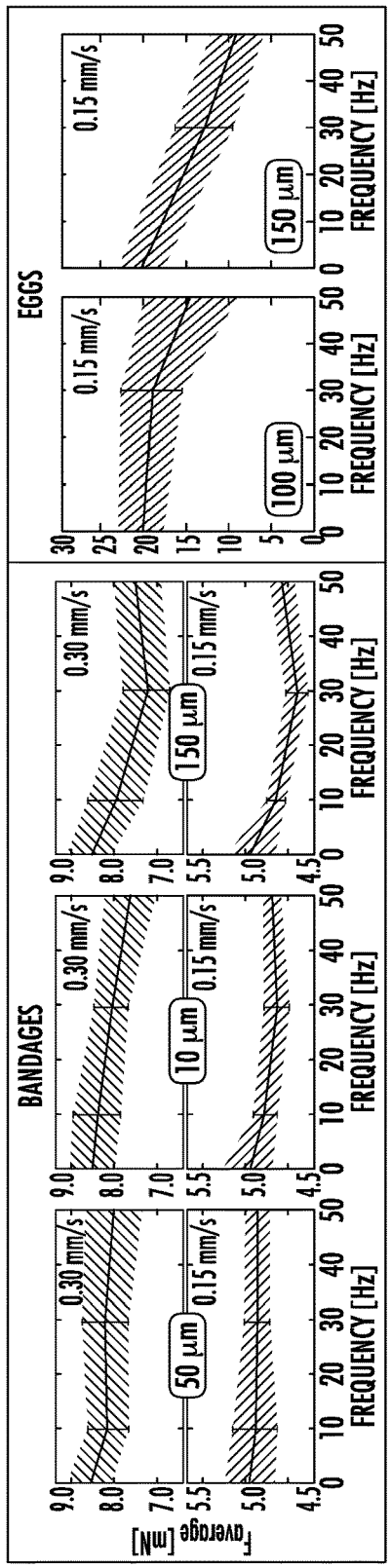
FIG. 39A shows the variation of the average peeling force ($F_{average}$) with respect to the frequency, where dotted lines represent the mean, and the shaded region is ±1 standard deviation.

The variation of delaminating forces with respect to micro-vibration frequency is shown in the table in FIG. 38 and in FIG. 39A for both phantoms. For $F_{average}$, no statistically significant difference was identified between the different frequency settings with a 50 μm amplitude ($p=0.62$). $F_{average}$ remained around 5 mN and 8 mN respectively for 0.15 mm/s and 0.30 mm/s speed settings regardless of the induced micro-vibrations. However, at larger amplitudes (100 and 150 μm), the change in force was significant. In the slower speed setting, $F_{average}$ was minimized at 30 Hz to 4.80 mN and 4.64 mN respectively for 100 μm and 150 μm vibrations ($p<0.05$). Doubling the speed changed this profile to a monotonically decreasing curve for 100 μm vibrations, but a similar concave trend with a minimum (7.19 mN) at 30 Hz appeared for 150 μm vibrations ($p<0.05$). $F_{average}$ for shell membranes (20.2 mN) was much larger as compared to bandages (5.02 mN). Introducing micro-vibrations with increasing frequency gradually decreased this force, down to 9.02 mN at 50 Hz. The drop was statistically significant for all settings ($p<0.05$) except for 30 Hz vibrations at 100 μm ($p=0.24$). The change in $F_{average}$ combined with the amplitude of force fluctuations due to induced vibrations affected $F_{peak}$ as well. Peeling bandages with 10 Hz vibrations resulted in a reduced $F_{peak}$ for the slower speed setting. Though for the faster peeling case, only 10 Hz and 50 μm vibrations produced this result. In most cases—excluding the slower peeling tests with 150 μm vibrations—$F_{peak}$ gradually rose as the frequency was increased ($p<0.05$).

Figure 39B:
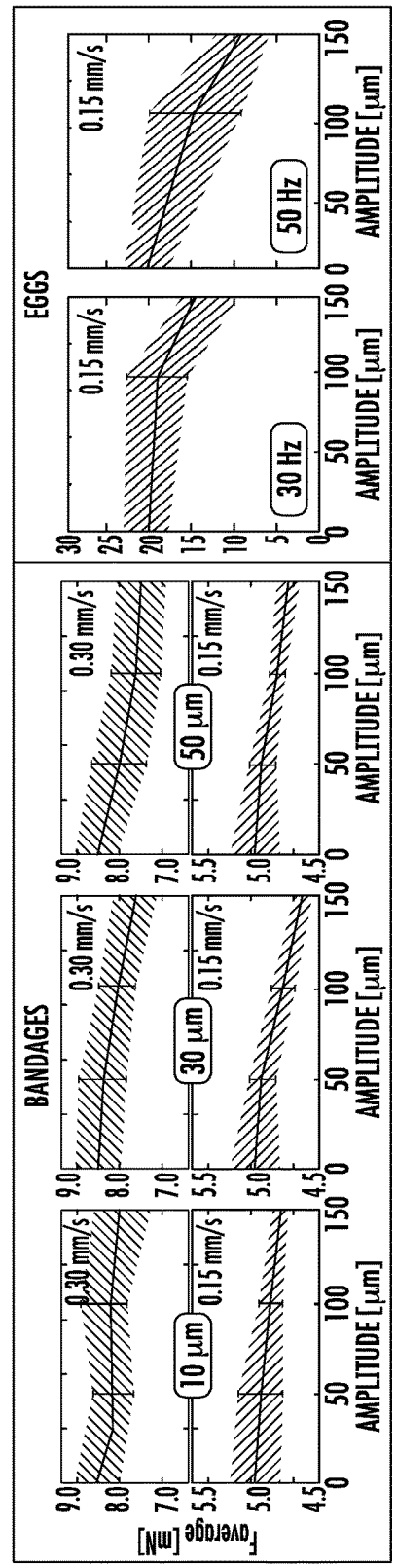
FIG. 39B variation of delaminating forces with respect to micro-vibration amplitude, where dotted lines represent the mean, and the shaded region is ±1 standard deviation.
Figure 40:
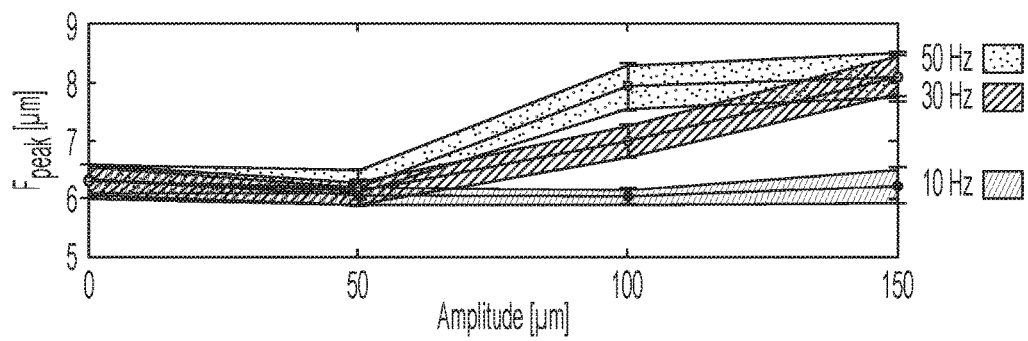
FIG. 40 shows the variation in the maximum peeling force ($F_{peak}$) with respect to the micro-vibration amplitude at different frequencies while peeling bandages with 0.15 mm/s speed.

The effect of vibration amplitude on $F_{average}$ is shown in FIG. 39B. On bandages, introducing 50 and 100 μm vibrations did not change $F_{average}$ significantly at 10 Hz ($p=0.13$). However, when keeping the frequency at 10 Hz, and increasing the amplitude to 150 μm, the force for both speed settings was lowered ($p<0.05$). At 30 Hz and 50 Hz, a common trend was observed in both bandages and eggs: $F_{average}$ monotonically decreased with larger amplitude. This decay was more significant in shell membrane and faster (0.30 mm/s) bandage peeling trials. Despite the inverse relation between the vibration amplitude and $F_{average}$, the cost of using larger vibrations is increased force fluctuation, which may in fact result in larger $F_{peak}$ (FIG. 38). This trend can clearly be seen in slower (0.15 mm/s) bandage peeling trials (FIG. 40). At 10 Hz trials, no significant change in $F_{peak}$ can be observed since the reduction in $F_{average}$ was greater than the amount of force fluctuation even for 150 μm oscillations. However, at 30 and 50 Hz, as the vibration amplitude is increased, the drop in $F_{average}$ fails to compensate for the resulting force fluctuation, producing a larger $F_{peak}$. This implies that the amplitude of micro-vibrations cannot simply be maximized to reduce $F_{average}$, but rather requires careful tuning to produce a smaller $F_{average}$ while keeping $F_{peak}$ below dangerous levels.

Herein we have described the influence of the micro-vibration parameters on average and maximum membrane peeling force in two peeling models; one a dry phantom and the other a biological model. We combined a force-sensing micro-forceps tool with a micromanipulator, Micron, to provide firm tissue grasping and vibratory tool motion at three levels of frequency (10, 30 and 50 Hz) and amplitude (50, 100 and 150 μm). Our observations are focused on tool-to-tissue interactions, which are not specific to the used system (Micron), and remain still valid with the other available robotic systems, such as the Steady-Hand Robot. Upon introducing micro-vibrations, the average peeling forces were lowered for both the bandages and the egg shell membranes, reaching a minimum mostly at 30 Hz for the bandages and at 50 Hz for the egg shell membranes. The force-frequency trend varied depending on the phantom type, peeling speed and the vibration amplitude. Increasing the vibration amplitude within the explored range (50-150

μm) resulted in a consistent decay in the average peeling force at higher frequencies (30 and 50 Hz). Nevertheless, because larger vibrations result in higher force fluctuations, there remains a potential risk that the peak force value may exceed the safety limits (even when the average force is lower) if the vibration amplitude is not carefully tuned.

REFERENCES

1. B. Gonenc, M. A. Balicki, J. Handa, P. Gehlbach, C. N. Riviere, R. H. Taylor, and I. Iordachita, "Preliminary Evaluation of a Micro-Force Sensing Handheld Robot for Vitreoretinal Surgery," in *Proc. IEEE Int. Conf on Intelligent Robots and Systems (IROS '12)*, 2012, pp. 4125-4130.
2. N. Cutler, M. Balicki, M. Finkelstein, J. Wang, P. Gehlbach, J. Mc-Gready, I. Iordachita, R. Taylor, and J. T. Handa, "Auditory force feedback substitution improves surgical precision during simulated ophthalmic surgery," *Investigative Ophthalmology & Visual Science*, vol. 54, no. 2, pp. 1316-1324, February 2013.
3. J. Damadian, "Method of conducting a needle biopsy procedure," U.S. Pat. No. 6,702,761, Mar. 6, 2001.
4. B. Gonenc, P. Gehlbach, J. Handa, R. H. Taylor, and I. Iordachita, "Motorized Force-Sensing Micro-Forceps with Tremor Cancelling and Controlled Micro-Vibrations for Easier Membrane Peeling," in *Proc. IEEE RAS EMBS Int. Conf. Biomed. Robot. Biomechatron. (BioRob '14)*, 2014, pp. 244-251.
5. R. A. MacLachlan, B. C. Becker, J. Cuevas Tabarés, G. W. Podnar, L. A. Lobes, and C. N. Riviere, "Micron: an actively stabilized handheld tool for microsurgery," *IEEE Trans Robot*, vol. 28:1, pp. 195-212, February 2012.
6. I. Iordachita, Z. Sun, M. Balicki, J. Kang, S. Phee, J. Handa, P. Gehlbach, and R. Taylor, "A sub-millimetric, 0.25 mn resolution fully integrated fiber-optic force-sensing tool for retinal microsurgery," *International Journal of Computer Assisted Radiology and Surgery*, vol. 4, pp. 383-390, June 2009.

Example 4—Force-Sensing Microneedle for Assisted Retinal Vein Cannulation

There are three main challenges associated with Retinal Vein Cannulation (RVC): (1) guiding the tool tip onto the target retinal vein accurately, (2) piercing the vein wall and stopping the cannula insertion at the correct depth, and (3) maintaining the needle tip inside of the vessel during drug injection. Retinal veins are very small structures (Ø 60-100 μm) and injection into these veins requires the use of even smaller microneedles. On the other hand, the physiological hand tremor of vitreoretinal surgeons has been measured at over 100 μm in amplitude [1], which significantly hinders accurate aiming during needle insertion as well as the ability to maintain cannulation during injection. As a remedy, teleoperated [2], cooperatively controlled [3], and handheld [4] robotic devices were proposed for RVC. Although smooth and accurate tool motion is achieved via these robotic systems, challenges to identifying the vessel puncture, establishing cannulation and maintaining it during drug injection persists.

In other applications involving needle insertion into blood vessels, such as sampling blood from the forearm, much larger forces compared to retinal microsurgery are applied, which enables the clinician to sense puncture and identify the moment at which the needle enters the blood vessel [5]. In contrast, the required forces for cannulating human retinal veins are almost imperceptible. Tests on chorioallantoic membrane (CAM) of chicken embryos, have been reported to be a valid in vivo model for human RVC studies [6], and have confirmed that most RVC forces are below the human perception threshold [7], yet with similar force variation trends observed in forearm blood sampling [8]. Thus, feedback based on the applied forces can potentially indicate the moment of vessel puncture in RVC as well, thereby allowing the operator to appropriately begin drug injection without causing further damage to the vasculature. Utilization of such force signatures though requires the ability to measure micro-forces inside of the eye.

To provide force feedback in retinal microsurgery, a family of force-sensing instruments was developed at JHU using fiber Bragg grating (FBG) strain sensors. These tools were developed in two forms, hook [9, 10] or micro-forceps [11-13], to assist specifically membrane peeling in vitreoretinal practice. The force sensing architecture in these designs enables accurate measurement of micro-forces directly at the tool tip with sub-mN resolution. This paper reports a new force-sensing RVC instrument that can easily be integrated with the existing manual tools, and robotic devices. The tool enables (1) the measurement of the forces required for puncturing retinal veins in vivo and (2) an assistive method to inform the operator of the needle piercing the vessel wall. We will first present the design of our tool. This will be followed by cannulation experiments using CAM of fertilized chicken eggs.

Figures 41A, 41B, 41C:
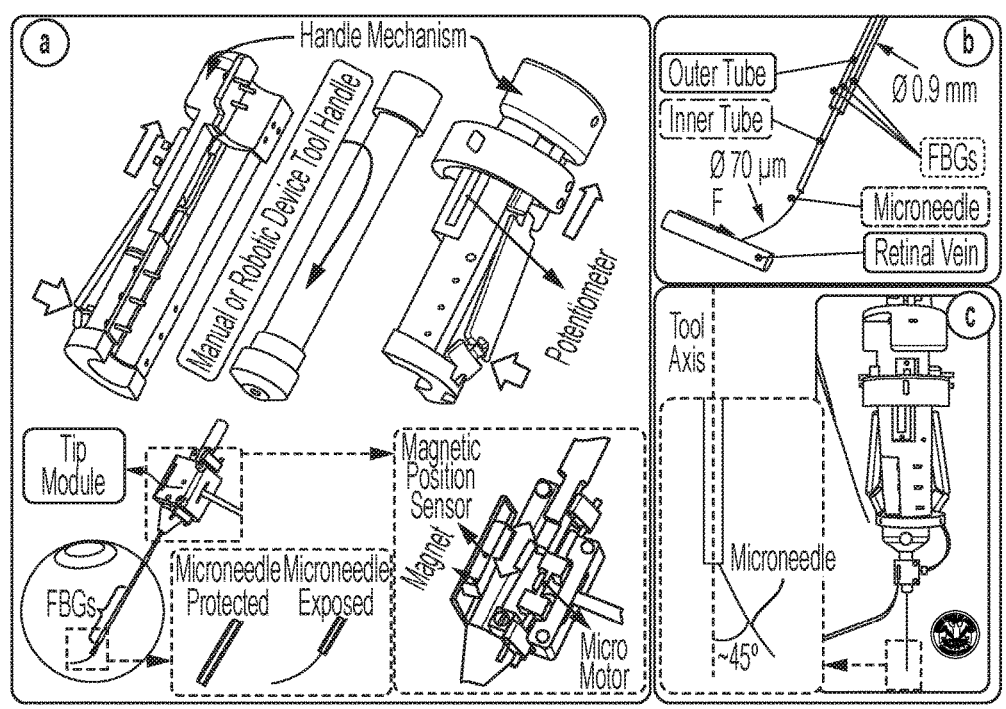
FIG. 41A illustrates the force-sensing microneedle tool concept with the tip module and the handle mechanism.
FIG. 41B shows how the inner tube of the tool shaft delivers the injection fluid, while three FBG sensors on the outer tube sense transverse forces on the microneedle tip.
FIG. 41C shows a microneedle system according to some embodiments of the invention, wherein the microneedle tip is pre-bent 45° relative to the tool axis to enable more gradual approach to the retina surface.

The design consists of two units: tip module, and the handle mechanism (FIG. 41A). The tip module carries a linear micro motor, Squiggle-RV-1.8 by New Scale Technologies Inc., driving a slider back and forth along the pins of the base. The tool shaft is formed by two concentric steel tubes (FIG. 41B). The outer 23 Ga tube is attached to the slider and performs two main functions: (1) it carries the force sensing FBGs which will be described in more detail below; (2) it functions as a mobile protective cover for the microneedle. The inner 30 Ga tube is fixed relative to the base, carries the injection fluid, and is connected to the microneedle at the tool apex. The microneedle has a beveled tip and is pre-bent, 45° relative to the tool axis, to enable more gradual and thus safer approach to the retina surface. The needle tip has an outer diameter of 70 μm for injection into very small retinal veins (~Ø 100 μm). It is kept protected and straight inside the outer tube before insertion into the eye. Upon reaching the target vessel site, the outer tube, attached to the slider mechanism, is retracted back via the linear micro motor, and the sharp microneedle tip is exposed for cannulation (FIG. 41A). Fully covering and exposing the microneedle requires a travel of 5 mm. The selected micro motor supplies enough force and travel for this task in a very small (2.8×2.8×6 mm), and light weight (0.16 grams) package. There is a bar magnet located on the side of the slider. The position of the slider, and thus of the micro motor, is tracked via the position sensor fixed on the side of the base to enable closed loop position control of the motor. This ensures accurate motion of the outer tube despite the potentially variable friction at the insertion port through the sclera. The outer diameter of the tip module tool shaft is small enough to fit through a Ø 0.9 mm incision on the sclera.

The handle mechanism is a simple interface for controlling the motor actuation. It can clamp around any cylindrical manual or robotic tool handle up to 25 mm in diameter. The spring loaded sides of the mechanism are normally kept propped open. Squeezing the sides pushes the sliders up, and changes the voltage output of the connected potentiometer to drive the micro motor back, thus retracts the outer tube and exposes the microneedle tip (FIG. 41A).

Detection of vessel puncture while cannulating vessels on CAM, and similarly retinal veins, requires the integration of a very sensitive force sensor with sub-mN resolution on the described tip module. Since the forces at the sclera insertion port can be much larger than the typical cannulation forces at the tool tip, the force sensing elements need to be located close to the tool apex and inside of the eye. FBG strain sensors (Smart Fibers, UK), with their small dimension, high sensitivity, biocompatibility, sterilizability, and immunity from electrostatic and electromagnetic noise satisfy these criteria.

Figures 42A, 42B:
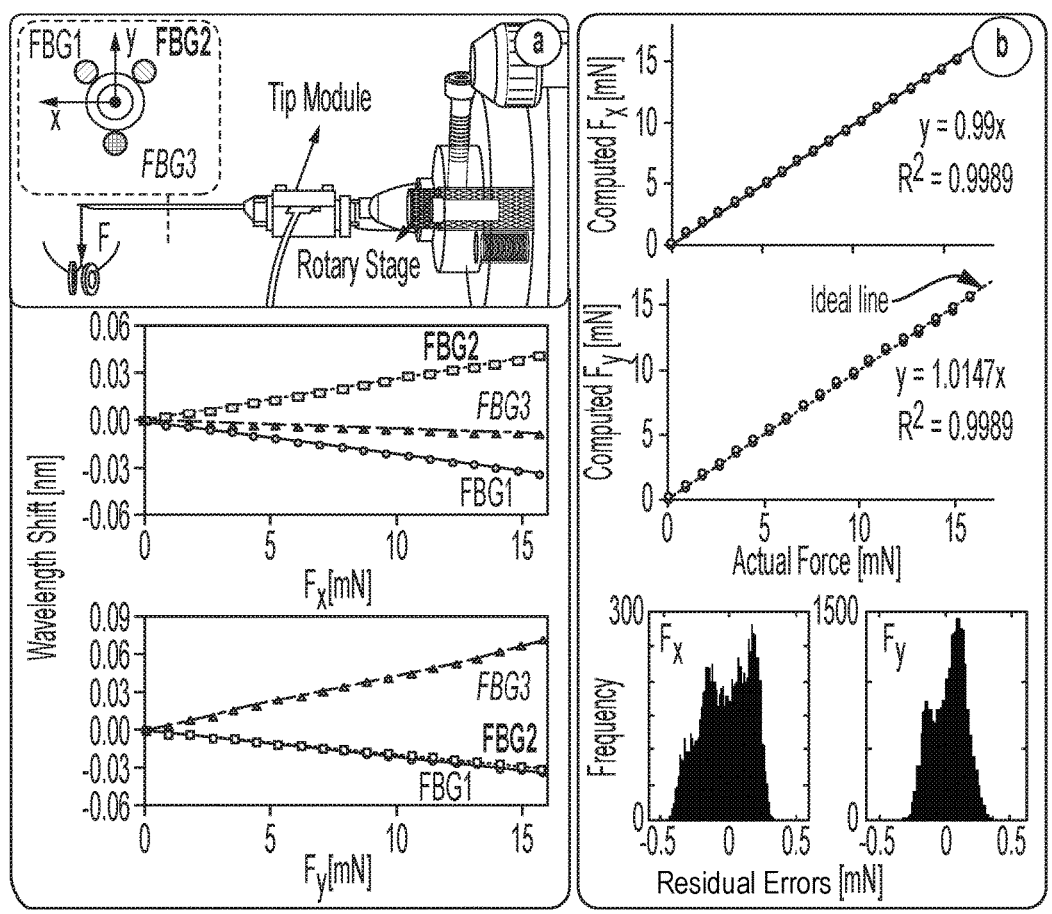
FIG. 42A shows calibration results for FBGs when the tip is loaded along the x and y axes.
FIG. 42B shows computed forces versus actual forces along the x and y axes (upper plots) and a histogram of the residual errors (lower plot)

Sensing only the transverse loads on the tool tip is sufficient for RVC since due to design (bent tip), forces induced on the tool tip during insertion will be mostly lateral. To integrate this capability onto the tip module, 3 FBGs were fixed evenly around the 23 Ga outer tube (FIG. 41B) using medical epoxy adhesive following the fabrication method presented in [9]. The calibration setup and protocol of the force sensor also follow [9]. All FBGs exhibit a linear reproducible behavior during both the x- and y-axis calibration procedures, as shown in FIG. 42A. The slopes of the response curves form the calibration matrix (K). The pseudo-inverse of this matrix ($K^+$) is used in the linear relationship (4.1) to compute the transverse tool tip forces ($F_x$ and $F_y$) from FBG wavelength shifts ($\Delta S$) during the operation.

$$\begin{bmatrix} F_X \\ F_Y \end{bmatrix} = K^+ \cdot \Delta S \text{ where } K = \begin{bmatrix} -0.00211 & -0.00264 \\ 0.00262 & -0.00184 \\ -0.00052 & 0.00448 \end{bmatrix}. \quad (4.1)$$

In order to monitor the FBGs, an optical sensing interrogator, sm130-700 from Micron Optics Inc. (Atlanta Ga.), was used. The wavelength resolution of the interrogator is 1 pm. Based upon the obtained calibration matrix, this corresponds to a transverse force resolution of about 0.22 mN, which is sufficient to detect the very fine changes in RVC. For verification, computed forces were compared with actual forces while the tip was loaded and unloaded repeatedly in different angles, as illustrated in FIG. 42A. Results showed consistency with the actual force values for both $F_x$ and $F_y$, and a close fit to the ideal straight line (slope=1) through the origin (FIG. 42B). The root mean square (RMS) error is 0.18 mN and 0.21 mN respectively for $F_x$ and $F_y$. The histogram of the residual errors in FIG. 42B show that the probability of errors beyond 0.5 mN for $F_x$ and $F_y$ is very low.

Figure 43:
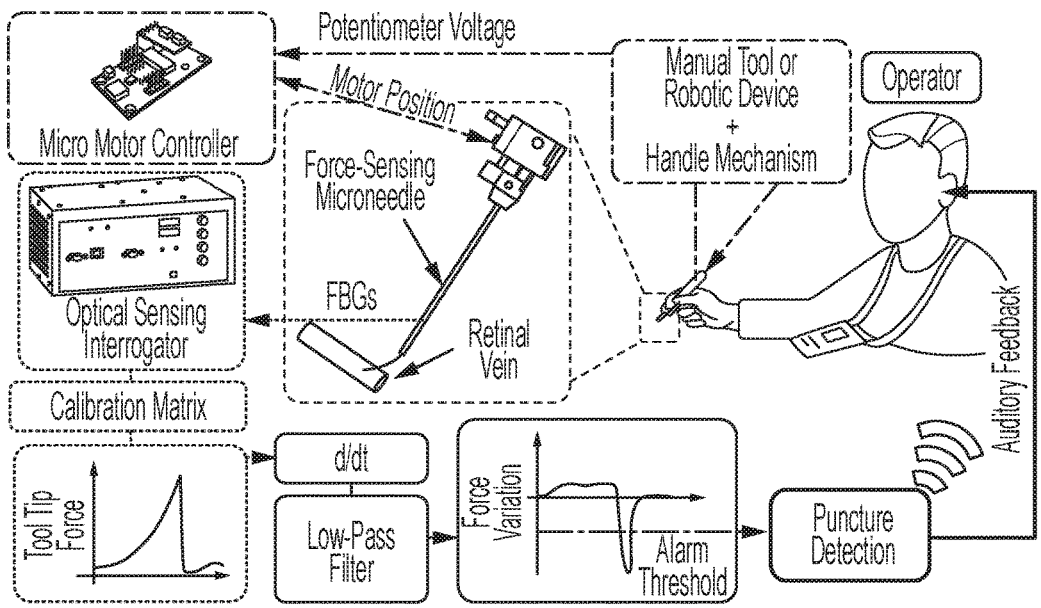
FIG. 43 illustrates a control scheme, wherein the potentiometer of the handle mechanism drives the motor of the tip module, and thus exposes the microneedle tip.

The tip module in this design packs its own actuator and sensors in a single compact independently actuated unit. In addition, the tip module and the handle mechanism are mechanically decoupled from each other. This enables easy integration with the existing manual tools and robotic devices such as in [2-4]. The control scheme of the force-sensing microneedle does not interfere with the operation of the integrated tool, and consists of two independent loops: micro motor control loop, and force feedback loop (FIG. 43).

Analog position servo input to the motor controller is provided by the sliding potentiometer on the handle mechanism. The magnetic sensor on the tip module feeds the motor position back to the controller to accomplish accurate closed loop control, exposing or protecting the microneedle tip without noticeable delay. In earlier needle puncture studies using rabbit ear veins [5] and CAM of fertilized chicken eggs [7], a characteristic force behavior was reported. After the needle tip touched the tissue surface, the insertion force gradually rose until a sharp drop signaling the entrance of needle tip into the vein. The force feedback control loop in our control scheme aims to identify this instant and alert the operator so that the needle does not overshoot and stays inside of the vessel. For this aim, a custom LabVIEW program was developed. During the operation, first, the wavelength information from each FBG channel is collected and processed at 1 kHz and transmitted over TCP/IP to the LabVIEW environment. Using the calibration matrix, the transverse force at the tool tip is obtained. Then, the time derivative of tip force is computed and passed through a second-order low-pass filter. The optimal filter parameters (cutoff frequency and damping coefficient) were tuned based on measured force profiles in [7] so that the sharp drop, thus the vessel puncture, could be detected with minimal delay. If the filtered derivative of force is less than a certain threshold (0.005 mN/s for CAM), then the operator is warned with an alarm sound so that the needle advancement is stopped.

Figure 44:
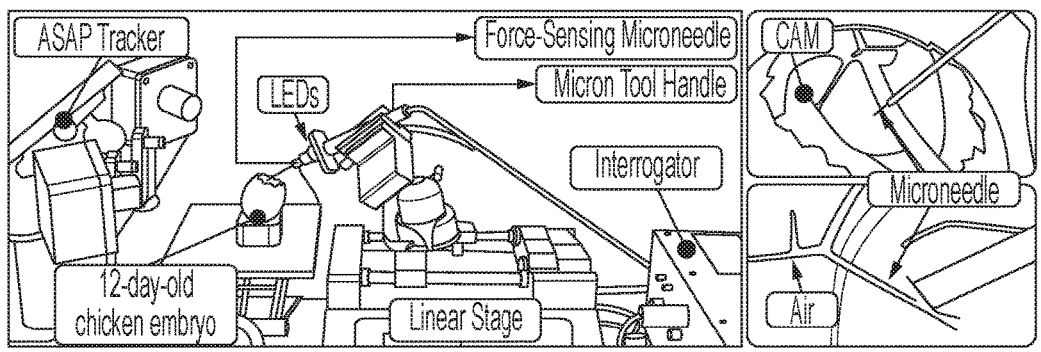
FIG. 44 shows the setup for vein cannulation experiments on CAM of 12-day fertilized chicken eggs, wherein the force-sensing microneedle is driven by a linear stage at constant speed while its position is recorded by an ASAP tracker.

To assess the feasibility of force-sensing microneedle, vein cannulation experiments were performed on the setup shown in FIG. 44 by a non-surgeon subject with no prior cannulation experience. To simulate the retina and its vasculature, CAM of 12-day-old chicken embryos were used due to their similar anatomical features and histological properties [6]. The tip module with the force-sensing microneedle was mounted on the handle of an optically tracked micromanipulator, Micron [4]. The Micron manipulator in the current tests was used as a passive tool handle only for the purpose of accurate tool tip tracking due its embedded infrared light-emitting diodes (LEDs) and the position-sensitive-detector cameras, namely the ASAP tracker. The Micron handle was fixed on a linear stage for driving the needle tip at constant speed along a straight trajectory. The microneedle was kept exposed at all times so that the use of the handle mechanism was not needed.

Before starting the experiment, the eggshell was partially removed to access the inner shell membrane (ISM). Then, the ISM was carefully peeled off using fine forceps to remove any variability in tests due to ISM thickness, and directly expose CAM. Tests were done driving the microneedle at two different levels of speed in alternating sequence: 0.3 mm/s and 0.5 mm/s. 8 trials were completed for each speed level. The task in each test was to cannulate a small vessel and inject air into it. The target vessels on CAM were chosen to be within 100-140 μm in diameter using a fine fiber (Ø 125 μm) for reference. After identifying the target, the microneedle was aimed and driven toward the vessel using the linear stage. The tip forces were monitored and an alarm sound was provided by the system upon sensing a puncture event. After hearing the alarm sound, the linear stage was stopped by the operator, and air injection was started. The success of vessel puncture, thus the implemented force feedback mechanism, was assessed based on the observation of air bubbles flowing in the vessel. For statistical analyses t-test assuming unequal variances was used with $p<0.05$ for statistical significance.

Figures 45A, 45B, 45C:
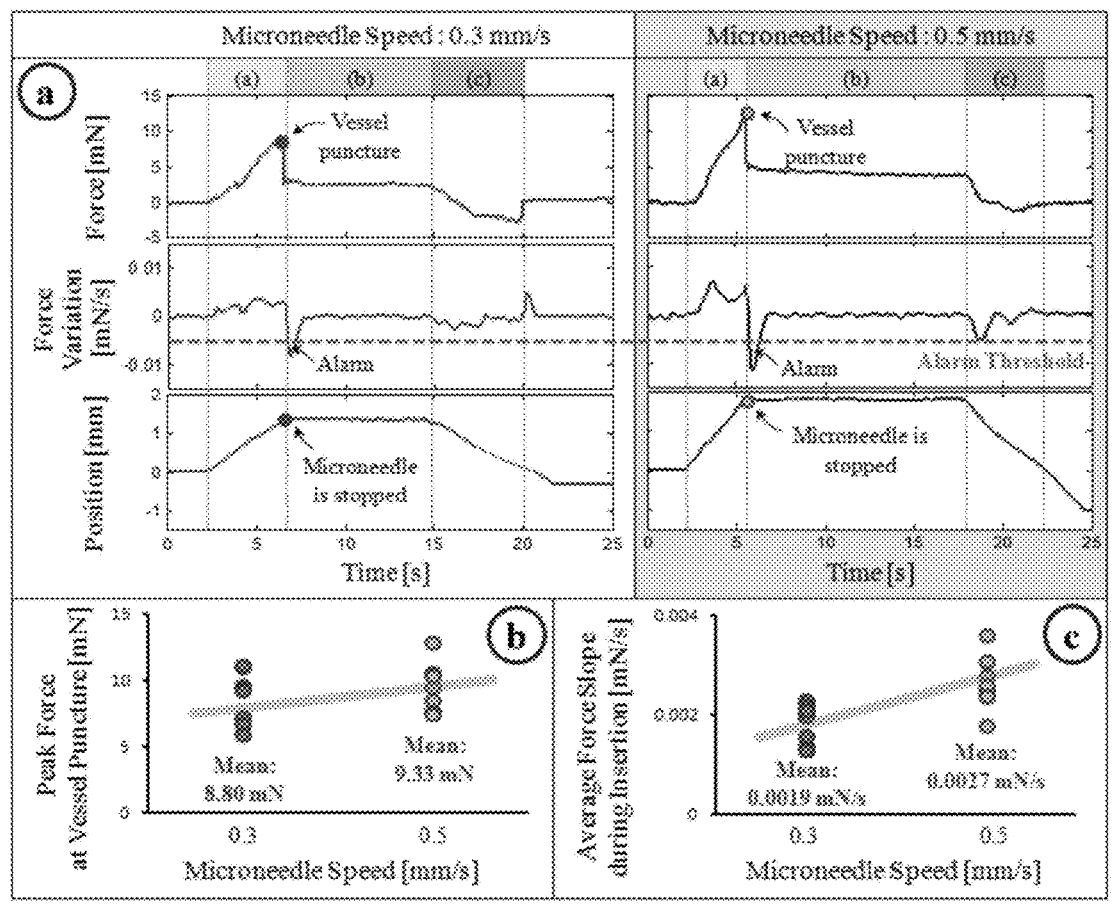
FIG. 45A shows data from a representative cannulation trial from each speed setting, wherein the sharp drop in force signifies vessel puncture and generates an alarm to warn the operator; (b,c) Force statistics for 8 trials per speed setting.
FIG. 45B shows the peak force at vessel puncture for eight trials per speed setting.
FIG. 45C shows the average force slope during insertion for eight trials per speed setting.

Typical results for each speed level are shown in FIG. 45A. After the microneedle touched the CAM surface, a gradually rising force, thus a positive force gradient was observed. At the end of phase (a), the microneedle pierced the vessel wall, which caused a sharp drop in the force and a sudden negative gradient triggering the auditory feedback mechanism. After the alarm sound, the stage was stopped manually and the needle was held in place during phase (b) while the operator started air injection to verify successful cannulation. During this time, the tool tip force remained the same. Then, the needle was retracted back while smaller forces in the opposite direction were measured at the tool tip.

In all trials, successful cannulation was achieved regardless of the speed setting. Although the overall force trend remained the same, statistical analyses revealed the effect of linear stage speed on the observed force variation and peak force values. As shown in FIG. 45B, the mean rate of change in force during phase (a) was higher in 0.5 mm/s setting (0.0027 mN/s) than the 0.3 mm/s setting (0.0019 mN/s) (p=0.0043). The mean peak force also increased with higher insertion speed (FIG. 45C), yet this was not a statistically significant difference (p=0.588). In both FIGS. 45B and 45C, the variation among the tests within each speed setting is mainly due to minor differences between embryos and selected vessel diameters.

We described herein a force-sensing microneedle tool enabling an assistive feedback mechanism for cannulating retinal veins more easily. The designed hardware is compatible and can easily be integrated onto many of the existing assistive robotic devices without interfering with their own control system. The force-sensing tip module is able to detect transverse forces on the tool tip with a resolution below 0.25 mN. The implemented feedback mechanism informs the operator upon vessel puncture and prevents overshoot based on the time derivative of sensed tool tip forces. Experiments on fertilized chicken eggs have shown 100% success in cannulating Ø 100-140 µm vessels, validating the use of such feedback based on force signatures in cannulation. In these experiments, the microneedle was driven by a linear stage at constant speed providing ease in testing such a time derivative based function. For practical use, similar tool stability and cannulation success with the same feedback mechanism can be achieved by integrating the developed force-sensing microneedle with one of the existing tremor-canceling robotic devices.

REFERENCES

1. S. P. N. Singh and C. N. Riviere, "Physiological tremor amplitude during retinal microsurgery," in Proc IEEE 28th Annu Northeast Bioeng. Conf., 2002, pp. 171-172.
2. T. Ueta, Y. Yamaguchi, Y. Shirakawa, T. Nakano, R. Ideta, Y. Noda, A. Morita, R. Mochizuki, N. Sugita, and M. Mitsuishi, "Robot-assisted vitreoretinal surgery: Development of a prototype and feasibility studies in an animal model," Ophthalmology, vol. 116:8, pp. 1538-1543, August 2009.
3. I. Fleming, M. Balicki, J. Koo, I. Iordachita, B. Mitchell, J. Handa, G. Hager, and R. Taylor, "Cooperative robot assistant for retinal microsurgery," Med. Image Comput. Comput. Assist. Interv., vol. 5242, 2008, pp. 543-550.
4. B. C. Becker, S. Yang, R. A. MacLachlan, and C. N. Riviere, "Towards vision-based control of a handheld micromanipulator for retinal cannulation in an eyeball phantom," in Proc. 4th IEEE RAS EMBS Int. Conf. Biomed. Robot. Biomechatron. (BioRob), 2012, pp. 44-49.
5. H. Saito, and T. Togawa, "Detection of needle puncture to blood vessel using puncture force measurement," Med. Biol. Eng. Comput., vol. 43:2, pp. 240-244, March 2005.
6. T. Leng, J. M. Miller, K. V. Bilbao, D. V. Palanker, P. Huie, and M. S. Blumenkranz, "The chick chorioallantoic membrane as a model tissue for surgical retinal research and simulation," Retina, vol. 24:3, pp. 427-434, June 2004.
7. O. Ergeneman, J. Pokki, V. Pocepcova, H. Hall, J. J. Abbott, and B. J. Nelson, "Characterization of puncture forces for retinal vein cannulation," J. Med. Dev., vol. 5:4, pp. 044504, December 2011.
8. A. Zivanovic, and B. L. Davies, "A robotic system for blood sampling," IEEE Trans. Inf. Technol. Biomed., vol. 4:1, pp. 8-14, March 2000.
9. I. Iordachita, Z. Sun, M. Balicki, J. Kang, S. Phee, J. Handa, P. Gehlbach, and R. Taylor, "A sub-millimetric, 0.25 mn resolution fully integrated fiber-optic force-sensing tool for retinal microsurgery," International Journal of Computer Assisted Radiology and Surgery, vol. 4, pp. 383-390, June 2009.
10. X. He, J. Handa, P. Gehlbach, R. Taylor, and I. Iordachita, "A sub-milimetric 3-dof force sensing instrument with integrated fiber Bragg grating for retinal microsurgery," IEEE Trans. Biomed. Eng., vol. 61:2, pp. 522-534, February 2014.
11. X. He, M. A. Balicki, J. U. Kang, P. L. Gehlbach, J. T. Handa, R. H. Taylor, and I. I. Iordachita, "Force sensing micro-forceps with integrated fiber bragg grating for vitreoretinal surgery," in Proc. of SPIE, vol. 8218, pp. 82180W 1-7, February 2012.
12. I. Kuru, B. Gonenc, M. Balicki, J. Handa, P. Gehlbach, R. H. Taylor, and I. Iordachita, "Force Sensing Micro-Forceps for Robot Assisted Retinal Surgery," in Proc. International Conference of the IEEE EMBS (EMBC '12), 2012, pp. 1401-1404.
13. B. Gonenc, E. Feldman, P. Gehlbach, J. Handa, R. H. Taylor, and I. Iordachita, "Towards Robot-Assisted Vitreoretinal Surgery: Force-Sensing Micro-Forceps Integrated with a Handheld Micromanipulator," in Proc. IEEE Int. Conf. on Robotics and Automation (ICRA '14), 2014, pp. 1399-1404.
14. B. Gonenc, J. Handa, P. Gehlbach, R. H. Taylor, and I. Iordachita, "A Comparative Study for Robot Assisted Vitreoretinal Surgery: Micron vs. the Steady-Hand Robot," in Proc. IEEE Int. Conf. on Robotics and Automation (ICRA '13), 2013, pp. 4832-4837.

Example 5—Force-Based Puncture Detection and Active Position Holding for Assisted Retinal Vein Cannulation Retinal vein occlusion (RVO) is the second most prevalent retinovascular disease affecting an estimated 16.4 million adults worldwide [1]. It is caused by intraluminal venous thrombosis, which obstructs the blood flow in the central retinal vein and/or its branches leading to potentially severe damage to the retina and vision loss. Retinal vein cannulation (RVC) is still an experimental surgical procedure proposed to treat RVO by direct therapeutic agent delivery methods. The procedure has historically involved the injection of clot-dissolving tissue plasminogen activator (t-PA) directly into the occluded vein [2].

Conventional venipuncture occurs on larger structures and the resulting tactile forces are both perceptible and familiar to experienced phlebotomists. Specifically the clinician can feel the moment of vessel puncture (the time at which the resistance force suddenly drops as the vein wall ruptures and the needle tip enters into the blood vessel) [3]. Unlike a routine venipuncture, cannulating human retinal veins occurs at forces that are almost imperceptible to humans. Tests in the chorioallantoic membrane (CAM)

model using chicken embryos—an accepted in vivo model for human RVC studies [4]—have confirmed that most RVC forces lie below the human perception threshold, yet there is still a sharp force drop upon venous puncture, as observed in a conventional venipuncture [5]. Continuous monitoring of these small forces therefore have the potential to inform the operator of the moment of vein puncture during RVC, thereby allowing the operator to halt needle advancement and appropriately begin drug injection minimizing damage to the delicate retinal vasculature. Utilization of such force signatures requires the ability to continuously measure micro-scale forces inside of the eye in real time.

To provide force feedback in retinal microsurgery, we developed a family of force-sensing instruments using fiber Bragg grating (FBG) strain sensors. These tools were originally designed in two forms (hook [6] and micro-forceps [7-9]) with a common sensor architecture, which was shown to accurately measure the micro-forces directly at the tool tip without significant degradation due to varying ambient temperature or the forces at the sclerotomy port. Following a similar approach, we developed a force-sensing microneedle with a thin (Ø70 µm), easily replaceable pre-bent (45°) tip for a safe RVC without overshoot [10]. This tool was driven on a linear stage and provided auditory feedback upon sensing the event of vessel puncture. When tested on CAM, the method led to successful cannulation of very thin veins (Ø<200 µm) without significant trauma in most of the trials.

This disclosure builds on our previous work, and combines our force-sensing microneedle with a micromanipulator, Micron. The microneedle (1) measures the tool-to-tissue interaction forces, and (2) informs the operator upon the event of vein puncture via auditory feedback. Micron (1) attenuates hand-tremor of the operator to provide a smoother and safer approach to the vein surface, and (2) holds the needle tip position fixed after venous puncture by actively compensating the unintentional movements of the operator to help maintain cannulation for a longer time. This is, to the best of our knowledge, the first handheld assistive RVC system that can detect venous puncture and act automatically.

Figures 46A, 46B:
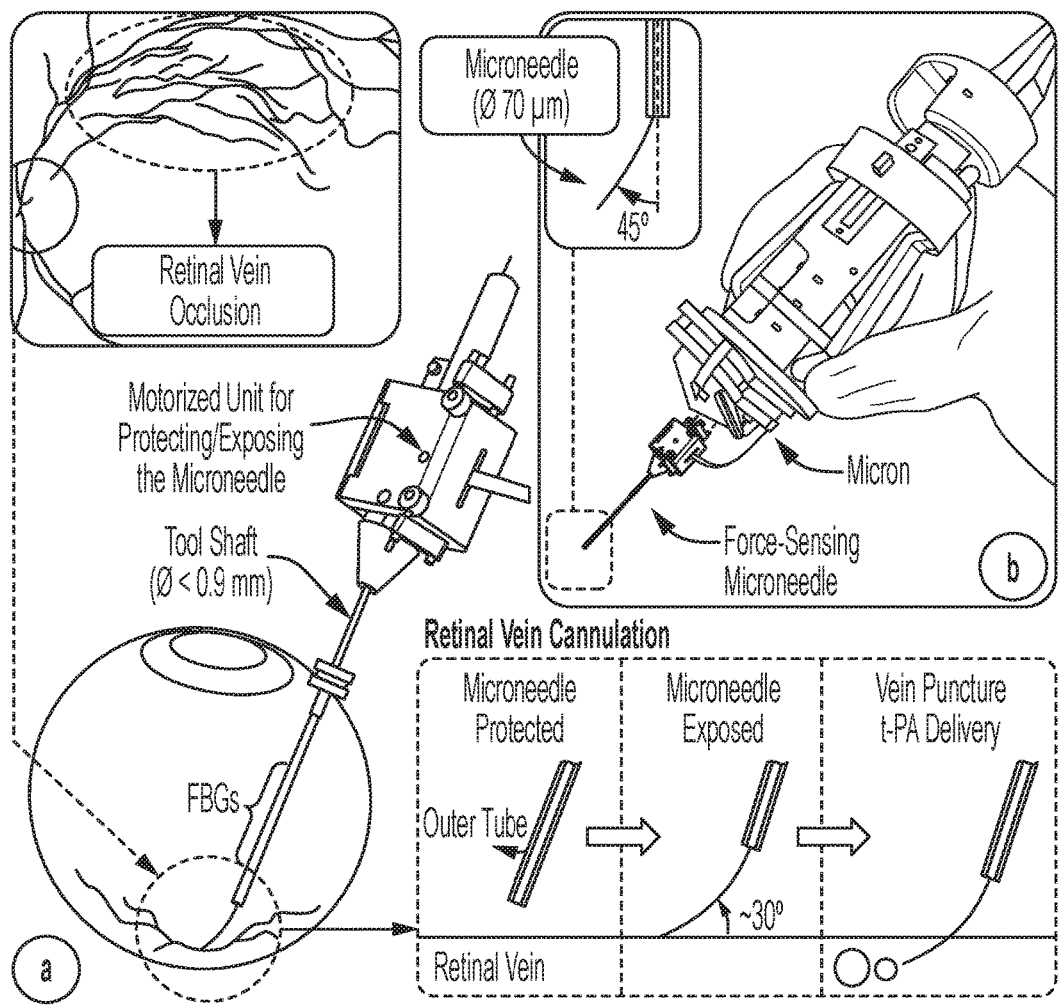
FIG. 46A gives a conceptual overview of assisted retinal vein cannulation.
FIG. 46B shows a micromanipulator according to some embodiments of the invention.

FIG. 46A gives a conceptual overview of assisted retinal vein cannulation. FIG. 46B shows a micromanipulator according to some embodiments of the invention. Injecting t-PA into thin branch retinal veins (Ø<200 µm) requires the use of even thinner and sharper tipped cannulae. Targeting Ø100-500 µm veins, we used a microneedle with an outer diameter of 70 µm (FIG. 46B). The microneedle has a sharp beveled (15°) and bent tip. If a straight microneedle were used, overshooting the target vein would be almost inevitable as the insertion forces would push the vein walls towards each other and make the already thin lumen even smaller. To avoid overshoot, it is important to approach the vein wall at an angle, and move the needle tip almost horizontally along the vein with minimal vertical motion into the vein. This is possible using a bent microneedle. However, due to its small size, bending the needle too much in order to achieve a very small and safe approach angle (1) causes excessive deformation of the needle before it can puncture through the vein, and (2) requires too much pressure to inject t-PA through. The optimal approach angle while cannulating the vasculature on CAM was previously studied, and was found to range from 25-35 degrees [11]. Considering the pars plana position for tool insertion, the size of the typical adult eye, and an ideal approach of ~30°, we bent the needle tip 45° relative to the tool shaft. In order to keep the sharp and bent microneedle protected and straight while inserting it through the sclera, we devised a motorized unit, which slides the outer tube in FIG. 46A along the tool shaft as a protective sheath to hide or expose the needle tip. This actuation is independent of the site of attachment, so that the microneedle can easily be used on any of the existing assistive robots [12-16] without interfering with their operation. The design and control mechanism of this part are further detailed in [10].

Detection of vessel puncture while cannulating retinal veins requires the use of a very sensitive force sensor with sub-mN resolution. Since the forces at the sclera insertion port can be much larger than the typical cannulation forces at the tool tip, the force sensing elements need to be located close to the tool apex and inside of the eye. FBG strain sensors (Smart Fibers, UK), with their small dimension, high sensitivity, biocompatibility, sterilizability, and immunity from electrostatic and electromagnetic noise satisfy these criteria. Sensing only the transverse loads on the tool tip can be sufficient for RVC since, due to design (bent tip), forces induced on the tool tip during insertion will be mostly lateral. This feature was added by fixing three FBGs evenly around the protective outer tube (FIG. 46A) using medical epoxy adhesive. This results in a total tool shaft diameter less than 0.9 mm, which is sufficiently small for insertion through the sclera.

Figures 47A, 47B, 47C:
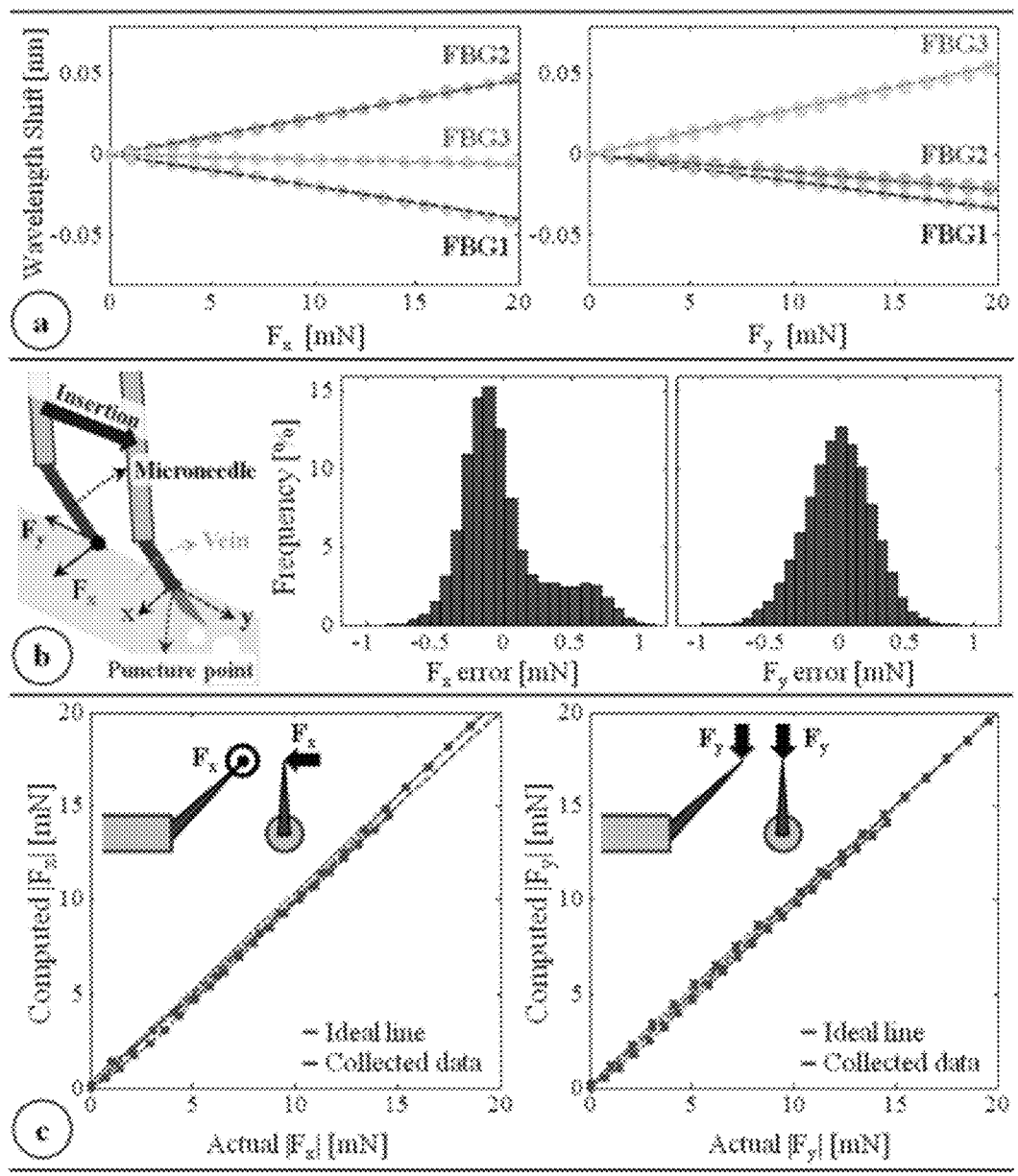
FIG. 47A shows calibration results for the FBGs when the needle is loaded along the x and y axes.
FIG. 47B shows the force-sensing coordinates relative to the target vein and a histogram of residual errors in each direction.
FIG. 47C shows computed forces versus actual forces along the x and y axes.

The calibration setup and protocol of the force sensors follow reference [6]. FIGS. 47A-47C show the calibration results. All FBGs exhibit a linear reproducible behavior during both the x- and y-axis calibration procedures, as shown in FIG. 47A. The pseudo-inverse of the resulting calibration matrix ($K^+$) is used in the linear relationship (5.1) to compute the transverse tool tip forces ($F_x$ and $F_y$) from the FBG wavelength shifts ($\Delta S$) during the operation:

$$\begin{bmatrix} F_x \\ F_y \end{bmatrix} = K^+ \cdot \Delta S \text{ where } K = \begin{bmatrix} -0.0020 & -0.0017 \\ 0.0023 & -0.0011 \\ -0.0003 & 0.0028 \end{bmatrix}. \quad (5.1)$$

In order to measure $\Delta S$, we use an optical sensing interrogator, sm130-700 from Micron Optics Inc. (Atlanta Ga.). The wavelength resolution of the interrogator is 1 pm. Based upon the obtained calibration matrix, this corresponds to a transverse force resolution of about 0.25 mN. To verify sensor operation, the tool tip was loaded and unloaded repeatedly in different angles (0°, 45° and 90°), and the computed forces were compared with the actual tip loading. The root mean square error was 0.31 mN and 0.24 mN respectively for $F_x$ and $F_y$. The histogram of the residual errors shown in FIG. 47B indicates that the probability of errors beyond 0.5 mN is very low. For 0-10 mN range, computed forces match the actual values for both $F_x$ and $F_y$, producing a close fit to the ideal straight line (slope=1) passing through the origin in FIG. 47C. Above 10 mN, although $F_y$ accuracy is preserved, $F_x$ is observed to slightly deviate from the ideal line as the loading is increased. This is the effect of torque generated due to the distance between the tip of bent needle and the tool shaft center as illustrated in FIG. 47C. Such error can in theory be corrected by modeling the error. However during RVC, since the needle insertion will take place mostly along the needle axis (y-axis of the tool), forces exceeding 10 mN along the x-axis are highly unexpected. Thus, the slight deviation in $F_x$ at larger amplitudes is not a major concern.

In order to suppress involuntary hand motion, and maintain the cannula inside the vein for a longer time while minimizing trauma to the vasculature, various robotic surgical systems can be used. Most of the existing platforms for intraocular surgery are mechanically grounded systems [11-15]. Alternative to these approaches is a handheld micromanipulator, Micron c[6, 7], which preserves the intuitive feel of manual handheld tools. It is normally designed to actively attenuate the physiological hand tremor of the surgeon. The position of its handle is determined by its custom microscale optical tracking system, namely the ASAP (Apparatus to Sense Accuracy of Position) [18]. After sensing the tool motion, it is filtered into its voluntary and involuntary (tremulous) components. Then activating its three piezoelectric actuators, Micron moves its tip to counteract the involuntary motion component within a workspace of approximately a 1×1×0.5 mm volume centered on the handle position. The control software for this operation mode is implemented in LabVIEW, and can be altered to perform other micromanipulation goals rather than solely tremor canceling.

In earlier needle puncture studies using rabbit ear veins [3] and CAM of fertilized chicken eggs [5], a characteristic force behavior was reported: after the needle tip touches the vein surface, the insertion force gradually rises until a sharp drop signaling the entrance of needle tip into the vein. Our team showed the feasibility of identifying this instant based on the time derivative of measured forces, and alerting the operator via auditory feedback earlier [10]. In [10], the microneedle was driven into the target vein using a linear stage, which provided a unidirectional continuous needle motion at a fixed speed. In this case, checking only the time derivative of force was sufficient and any drop in force $(d|\vec{F}_{needle}|/dt<0)$ could easily be related to a puncture event. Using a linear stage to drive the microneedle though, does not provide the necessary dexterity required while working on a real eye, which is thus replaced with Micron in this work.

Using a handheld tremor-canceling micromanipulator, it is difficult to guarantee a constant insertion speed. While pushing the needle against the vein wall, moving the tool slightly slower or backing up before puncture can cause a drop in force magnitude ($|\vec{F}_{needle}|$), which can be misinterpreted as a puncture event if the sensing system is checking only the time derivative of forces $(d|\vec{F}_{needle}|/dt)$. To avoid this error, it is important to define a puncture detection criterion based on both the measured tool tip position ($\vec{p}_{needle}$) and force ($\vec{F}_{needle}$). When the needle tip is in contact with the vein wall, the time derivative of the sensed force normally opposes the needle velocity direction. In other words, if the needle is moved into the vein deforming but not puncturing it, the derivative of the measured reaction force will be pointing out of the vein. Upon piercing the vein, however, this vector ($d\vec{F}_{needle}/dt$) instantaneously flips its orientation and points in the same direction as the velocity vector ($d\vec{p}_{needle}/dt$). This can easily be detected by checking the inner product of the two vectors. Since the microneedle is bent 45° relative to the tool shaft, the insertion will induce mostly transverse (negligible axial) forces at the tool tip. Thus, although the force sensing properties of our microneedle are limited to only two dimensions ($F_{needle}^x$ and $F_{needle}^y$), puncture of the vein can still be captured effectively by taking $dF_{needle}^z/dt=0$.

Figures 48, 49:
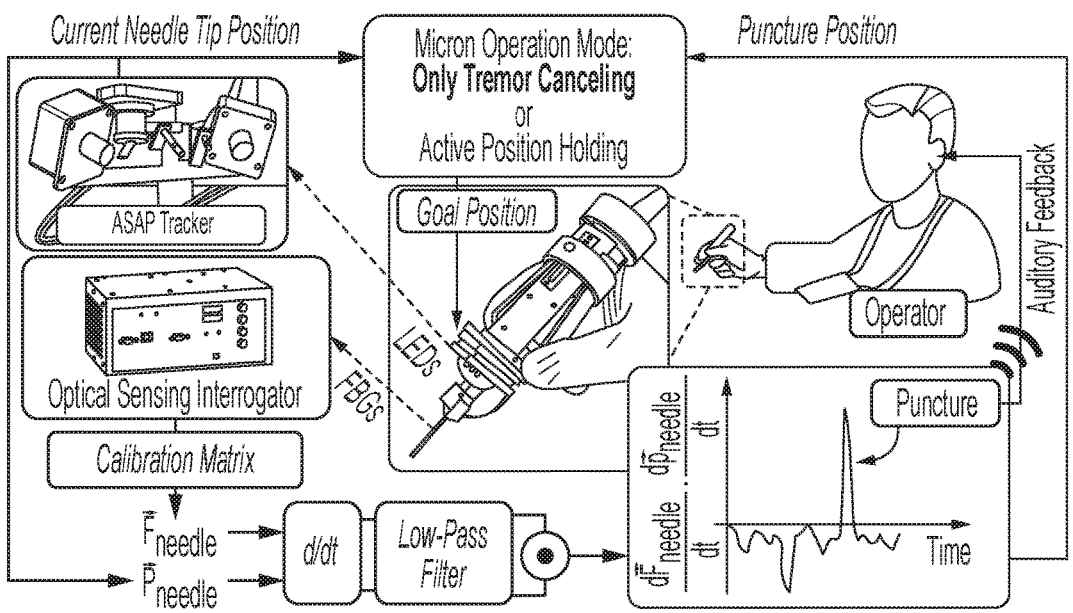
FIG. 48 shows the logic upon which the operation mode of Micron is regulated.
FIG. 49 shows a control scheme for the micromanipulation system.

The puncture detection algorithm was integrated with the Micron software via a custom LabVIEW program to provide auditory feedback to the operator and to hold the needle tip fixed with the aid of Micron upon venous puncture. The operation mode of Micron is regulated based on the logic presented in the table in FIG. 48. In the control scheme, which is illustrated in FIG. 49, the wavelength information from each FBG sensor is collected and processed at 1 kHz and transmitted over TCP/IP to the LabVIEW environment. Using the calibration matrix, the transverse force at the tool tip is obtained. Then, the time derivative of tip force is computed and passed through a second-order low-pass filter. The optimal filter parameters were tuned based on measured force profiles in [5] so that the sharp drop, thus the vessel puncture, could be detected with minimal delay. The tool tip position is acquired from the ASAP tracker at a sampling rate of 1 kHz, and the tip velocity is computed. During the needle insertion phase, Micron works in its regular tremor-canceling mode, filtering out the high frequency components of the sensed motion. When puncture is detected, an alarm sound is generated to inform the operator of the puncture event, and Micron locks its goal position to the tip position recorded at this instant (puncture position). In this mode of operation, even if the user unintentionally moves the Micron handle, Micron deflects its tip to actively compensate the motion so that the tip is held fixed right at the puncture point. This active position holding mode is functional within the limits of Micron's actuators (within a sphere of ~0.5 mm radius). Deviating from the puncture point beyond these limits will saturate the actuators, and thus may not be compensated. The operator still maintains the gross positioning control while Micron makes fine adjustments to fixate the tool tip. In this way, Micron actuation can be overridden if needed, in case the needle needs to be quickly removed from the tissue.

Figure 50:
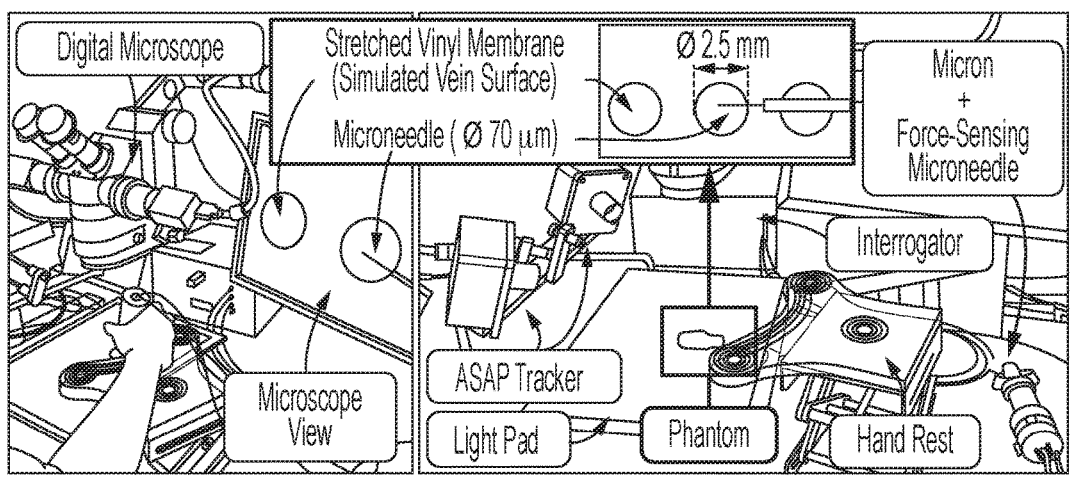
FIG. 50 shows the setup for evaluating the performance of system on an artificial phantom.

We performed a preliminary trial to quantify the effects of our system on operator performance during simulated cannulation trials. The setup, shown in FIG. 50, was designed to replicate the main challenges of RVC, and as a very consistent platform to enable testing. To simulate the retina and its vasculature, CAM is an anatomically similar model in both scale and the composition of structure and morphology [4]. However, using CAM, it is hard to guarantee phantom consistency throughout the trials due to slight differences in the size of cannulated veins, and the anatomical variation between the eggs. To simulate the vein wall with consistent mechanical behavior, we created an artificial phantom with thin membranes by stretching a vinyl layer onto an acrylic plate with circular holes (analogous to the polydimethyl siloxane sheet used in [13]). The force required for puncturing a vinyl layer with a needle highly depends on how much it is stretched. After studying the literature on the force magnitudes needed to puncture CAM vasculature, we adjusted the stretch amount so that the puncture force is about 20-25 mN. The corresponding vinyl layer thickness was measured with a micrometer to vary within 20-25 μm. The diameter of the holes on the acrylic plate (Ø=2.5 mm) was selected small enough to create the necessary support for a firm tensioned membrane, and large enough to prevent any collision between the plate and the microneedle during insertion. The phantom was fixed on a light pad to clearly visualize the membrane loci under a digital microscope The microscope view was displayed on a monitor providing only the top view of the phantom to the operator as in the case of a real RVC.

Tests were done by a non-surgeon subject with no prior cannulation experience, but with extensive training on the Micron system. The task in each trial was to puncture the vinyl membrane by moving the microneedle almost entirely laterally, in the direction the needle tip is pointing, and hold the needle fixed for 45 seconds after the event of puncture. Two cases were experimented by altering the operation mode of Micron: (1) only tremor canceling, and (2) active position holding. In either case, the operator was informed upon vein puncture via auditory feedback. The needle trajectory after this instant was recorded for analysis. In order to prevent significant performance degradation in time due to fatigue, tests were completed in 3 periods, each period involving a total of 8 trials (4 trials per case), with a 10 minute break between the periods. During the trials, Micron mode was altered in random order. Since each puncture causes the membrane to lose its tension locally, every new trial was done at a sufficiently distant location from the previous puncture loci. Performance assessment was based upon the recorded deviation from the point of puncture. Analyses were done by a t-test assuming unequal variance. Statistical significance was defined as $p<0.05$.

Figure 51A:
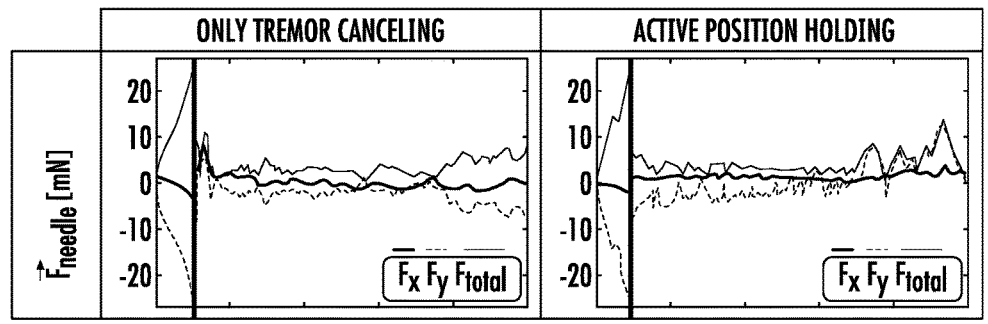
FIG. 51A shows the forces on the needle as a function of time during trials with only tremor canceling (left) and with active position holding (right)
Figure 51B:
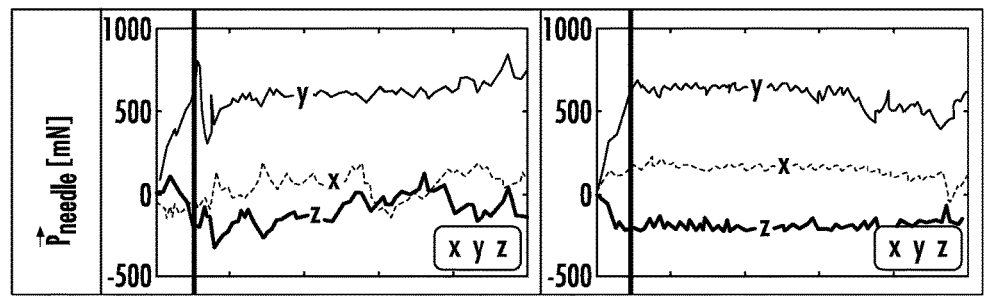
FIG. 51B shows the position of the needle as a function of time during trials with only tremor canceling (left) and with active position holding (right)
Figure 51C:
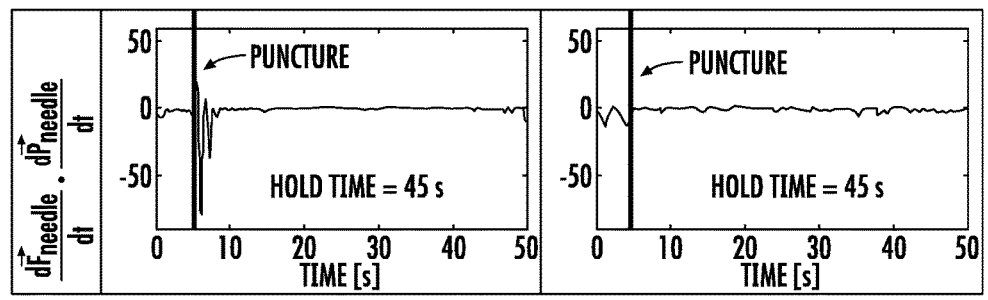
FIG. 51C shows the event of puncture as indicated by a positive peak in the inner product of the needle velocity and force variation vectors during trials with only tremor canceling (left) and with active position holding (right)

The measurements from a typical trial with only tremor canceling (OTC) and with active position holding (APH) are shown in FIGS. 51A-51D. In all trials, after the microneedle touched the membrane surface (the simulated vein wall), a gradual rise in force was observed. FIG. 51A shows the gradual rise in force during insertion, as well as a sharp drop at the instant of puncture. Most of the forces were exerted along the y-axis (all of the measured x-axis forces were below 3 mN) since the insertion was performed by moving the tool mostly laterally along the needle axis (y-axis) (FIG. 51B). The puncture force was 23.47±2.79 mN with OTC, and 23.24±2.67 mN with APH, revealing no statistically significant difference ($p=0.83$) between the mechanical behavior of the membranes used in either case. The event of puncture was successfully detected from the sharp positive peak in the inner product of needle velocity and force variation vectors, as shown in FIG. 51C. Throughout the 45-second period following this instant, the difference in tool tip travel between OTC and APH trials is clearly visible in FIG. 51B. In OTC, all components of the position vector fluctuated, especially the z-component due to operator's poor depth perception with the provided 2D microscope view. Using APH, the tool motion after the puncture was significantly lowered. The reduced deviation from the puncture point with APH can clearly be seen in FIG. 51D, which includes the needle tip trajectories recorded during three sample trials of each operation mode.

Figure 51D:
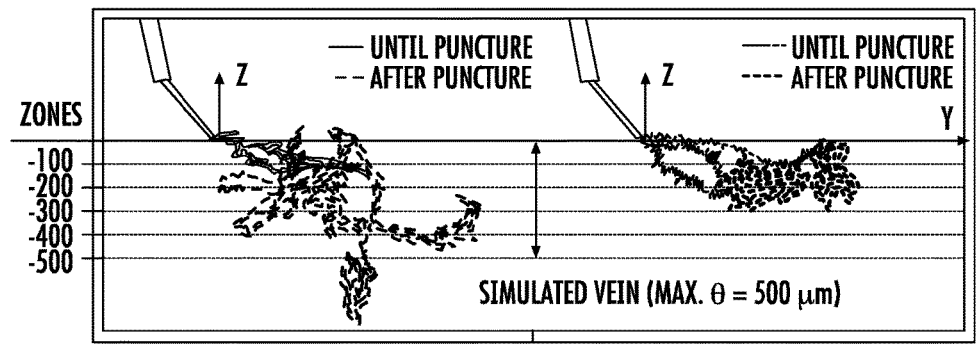
FIG. 51D shows the needle tip trajectories for during three trials with only tremor canceling (left) and during three trials with active position holding (right)
Figure 52:
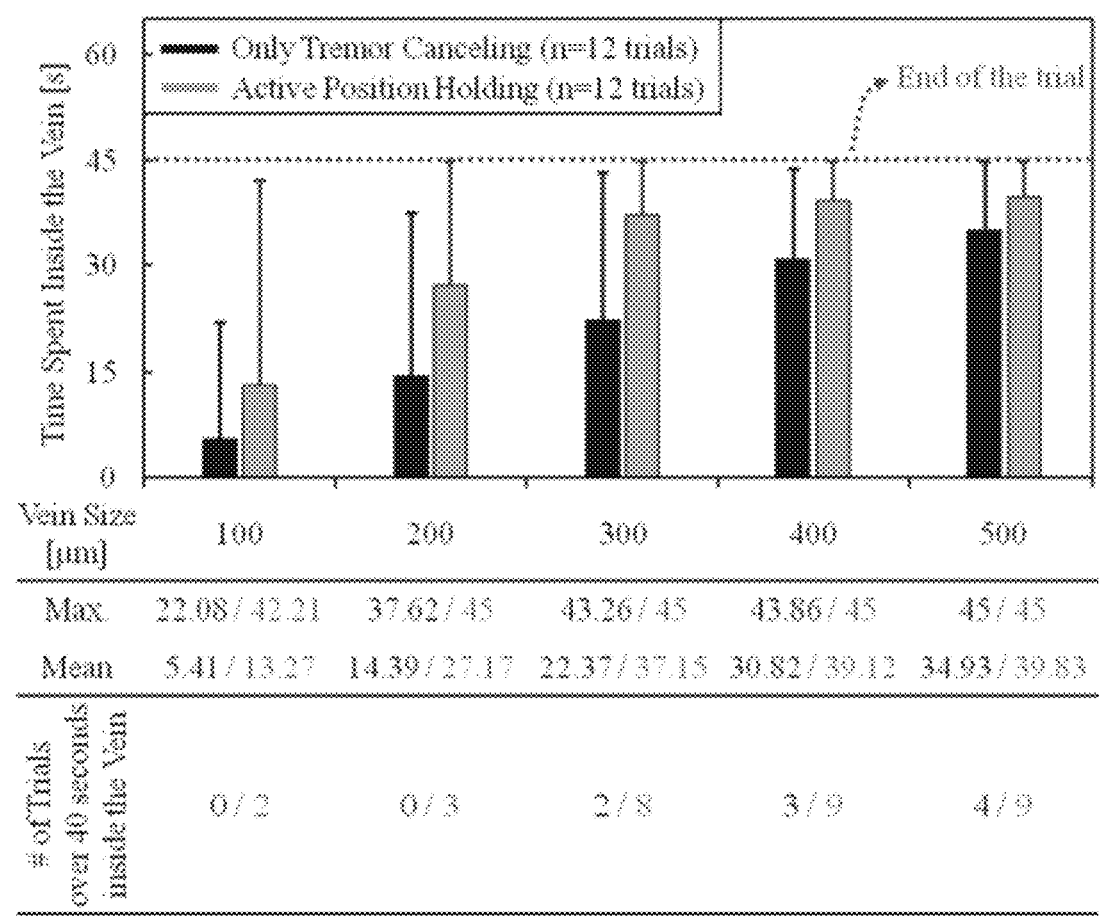
FIG. 52 shows the total time that the needle tip was maintained inside the vein versus the vein size.

In order to assess the ability to maintain cannulation in veins of different sizes, using the measured tool tip position throughout the entire hold time (45 seconds), we computed the time spent inside five different zones with varying distance from the puncture point (FIG. 51D). The size of each zone represents a vein diameter, and was decided based upon the typical vein sizes encountered in RVC (Ø 100-500 µm). The results shown in FIG. 52 indicate that, compared with the OTC trials, using APH enabled the operator to maintain the tip within the zone (thus the vein) for a significantly longer time for veins up to 300 µm ($p<0.05$). For instance, with OTC, the average time that the tip was maintained within a 100 µm distance from the puncture point was measured to be only 5.41 seconds with a peak value of 22.08 seconds out of the 45 second total test duration. In none of the 12 OTC trials could this duration exceed 40 seconds. However, upon using APH, the mean time was raised to 13.27 seconds, with 2 trials reaching a hold time over 40 seconds. Similar performance improvement with APH was observed in the 200 and 300 µm zones. For the 400 and 500 µm zones, in terms of the average time maintained inside, no statistically significant difference between OTC and APH could be identified ($p=0.07$ for 400 µm, $p=0.26$ for 500 µm). However, even for the 500 µm zone, where the performance of OTC and APH is closest, the number of trials with successful "in-zone" hold time over 40 seconds was still 50% greater in APH than OTC.

Figure 53:
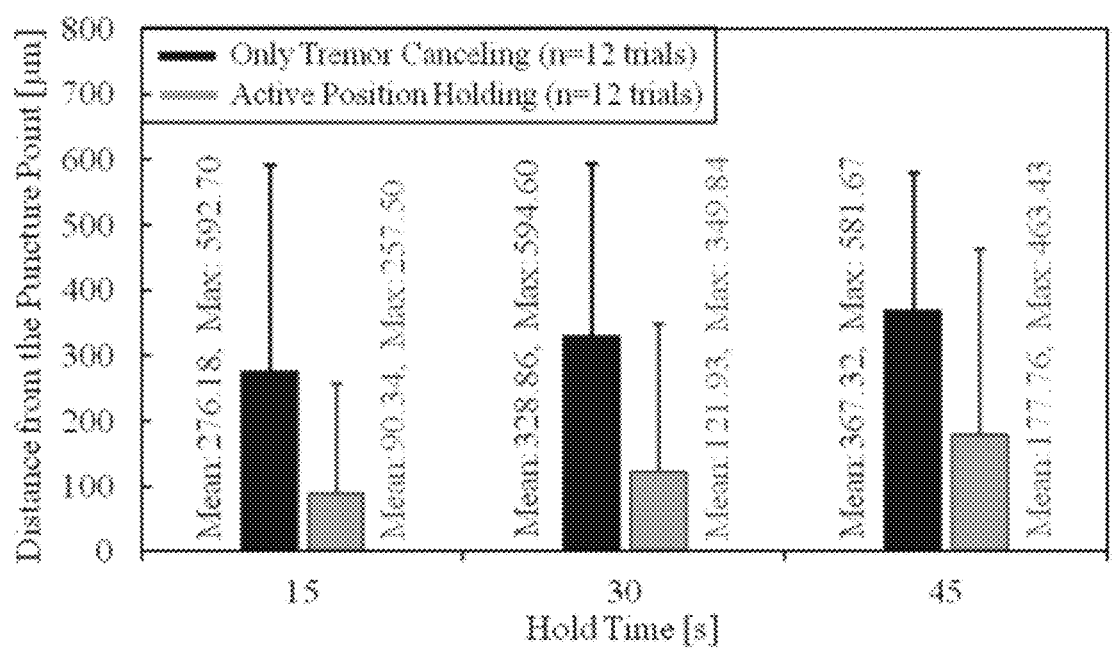
FIG. 53 shows the deviation from the puncture point versus hold time.

Our second performance metric was based on the range of needle tip travel after puncture—which needs to be minimized to reduce trauma—as a function of the hold time. For this, we analyzed the tip deviation during the first 15, 30 and 45 seconds after the puncture. The results are shown in FIG. 53. Accordingly, the almost linear rise in the maximum and mean tip travel as the needle is held for longer periods was inevitable, regardless of whether OTC or APH was used. Nevertheless, for all hold times, when APH was used, both the mean and the maximum distance from the puncture point was significantly lowered ($p<0.05$). In case of a 15-second hold time, the mean tip travel was reduced by more than 65% (from 276.18 µm to 90.34 µm). The decay was similar for the 30 and 45-second hold periods. The mean deviation from the puncture point during a 45-second hold exceeded 350 µm with OTC, whereas APH lowered it to below 200 µm, which shows that APH can potentially enable the cannulation of smaller veins, minimize trauma, and provide an extended period of intravenous cannula stability, potentially sufficient to allow sustained periods of drug delivery at tolerable pressures.

We describe herein an assistive system combining a handheld micromanipulator with a force-sensing microneedle. The system helped the operator detect the instant of puncture during RVC, and maintain cannulation for a longer period by actively holding the microneedle tip fixed inside the vein lumen. The event of puncture was sensed by continuously tracking the inner product of needle tip velocity and force derivative vectors. Our work using artificial phantoms, stretched vinyl membranes, has shown that the puncture detection algorithm combined with active positive holding can maintain the needle tip inside the vein for a much longer time, especially for smaller veins, and that it significantly attenuates the tool motion in the vein following venipuncture and cannulation.

The system described in this work employed an existing handheld micromanipulator for "active" tremor canceling and position holding purposes. The operation principle is easily integrable with the other existing cooperatively-controlled or teleoperated assistive devices to provide "passive" position holding instead. The range of motion that Micron can provide to actively compensate needle travel is limited (around 500 µm in each direction). Without proper training, an inexperienced user can easily saturate the device by unintentionally moving the instrument beyond this limit while trying to hold it still. Whilst a handheld device like Micron may be preferable to more experienced and skilled operators, the grounded robotic systems with their larger range of motion can potentially be a better option for novice users to learn and execute demanding tasks such as RVC.

REFERENCES

1. S. Rogers, R. L. McIntosh, N. Cheung, L. Lim, J. J. Wang, P. Mitchell, J. W. Kowalski, H. Nguyen, and T. Y. Wong, "The prevalence of retinal vein occlusion: Pooled data from population studies from the United States, Europe, Asia, and Australia," *Ophthalmology*, vol. 117, no. 2, pp. 313-19.e1, February 2010.
2. J. N. Weiss, and L. A. Bynoe, "Injection of tissue plasminogen activator into a branch retinal vein in eyes with central vein occlusion," *Ophthalmology*, vol. 108, no. 12, pp. 2249-2257, July 2001.

3. H. Saito, and T. Togawa, "Detection of needle puncture to blood vessel using puncture force measurement," *Med. Biol. Eng. Comput.*, vol. 43, no. 2, pp. 240-244, March 2005.
4. T. Leng, J. M. Miller, K. V. Bilbao, D. V. Palanker, P. Huie, and M. S. Blumenkranz, "The chick chorioallantoic membrane as a model tissue for surgical retinal research and simulation," *Retina*, vol. 24, no. 3, pp. 427-434, June 2004.
5. O. Ergeneman, J. Pokki, V. Pocepcova, H. Hall, J. J. Abbott, and B. J. Nelson, "Characterization of puncture forces for retinal vein cannulation," *J. Med. Dev.*, vol. 5, no. 4, pp. 044504, December 2011.
6. I. Iordachita, Z. Sun, M. Balicki, J. Kang, S. Phee, J. Handa, P. Gehlbach, and R. Taylor, "A sub-millimetric, 0.25 mn resolution fully integrated fiber-optic force-sensing tool for retinal microsurgery," *Int J Comput Assist Radiol Surg.*, vol. 4, no. 4, pp. 383-390, June 2009.
7. I. Kuru, B. Gonenc, M. Balicki, J. Handa, P. Gehlbach, R. H. Taylor, and I. Iordachita, "Force Sensing Micro-Forceps for Robot Assisted Retinal Surgery," in *Proc. International Conference of the IEEE EMBS*, San Diego, 2012, pp. 1401-1404.
8. B. Gonenc, J. Handa, P. Gehlbach, R. H. Taylor, and I. Iordachita, "Design of 3-DOF Force Sensing Micro-Forceps for Robot Assisted Vitreoretinal Surgery," in *Proc. International Conference of the IEEE EMBS*, Osaka, 2013, pp. 5686-5689.
9. B. Gonenc, P. Gehlbach, J. Handa, R. H. Taylor, and I. Iordachita, "Motorized Force-Sensing Micro-Forceps with Tremor Cancelling and Controlled Micro-Vibrations for Easier Membrane Peeling," in *Proc. IEEE RAS EMBS Int. Conf Biomed. Robot. Biomechatron.*, Sao Paulo, 2014, pp. 244-251.
10. B. Gonenc, P. Gehlbach, J. Handa, R. H. Taylor, and I. Iordachita, "Force-Sensing Microneedle for Assisted Retinal Vein Cannulation," in *Proc. IEEE SENSORS*, Valencia, 2014, pp. 698-701.
11. W. Wei, C. Popplewell, S. Chang, H. F. Fine, N. Simaan, "Enabling technology for microvascular stenting in ophthalmic surgery," *Journal of Medical Devices*, vol. 4, no. 1, March 2010.
12. P. S. Jensen, K. W. Grace, R. Attariwala, J. E. Colgate, and M. R. Glucksberg, "Toward robot-assisted vascular in the retina," *Graefe's Arch Clin Exp Ophthalmol*, vol. 235, no. 11, pp. 696-701, November 1997.
13. S. Tanaka et al., "Quantitative assessment of manual and robotic microcannulation for eye surgery using new eye model," *Int J Med Robotics Comput Assist Surg*, April 2014.
14. I. Fleming, M. Balicki, J. Koo, I. Iordachita, B. Mitchell, J. Handa, G. Hager, and R. Taylor, "Cooperative robot assistant for retinal microsurgery," *Med. Image Comput. Comput. Assist. Interv.*, vol. 5242, 2008, pp. 543-550.
15. A. Gijbels, N. Wouters, P. Stalmans, H. Van Brussel, D. Reynaerts, and E. Vander Poorten, "Design and realisation of a novel robotic manipulator for retinal surgery," in *Proc. IEEE Int. Conf on Intelligent Robots and Systems*, Tokyo, 2013, pp. 3598-3603.
16. B. C. Becker, S. Yang, R. A. MacLachlan, and C. N. Riviere, "Towards vision-based control of a handheld micromanipulator for retinal cannulation in an eyeball phantom," in *Proc. 4th IEEE RAS EMBS Int. Conf Biomed. Robot. Biomechatron.*, Rome, 2012, pp. 44-49.
17. B. C. Becker, R. A. MacLachlan, L. A. Lobes, G. D. Hager, C. N. Riviere, "Vision-based control of a handheld surgical micromanipulator with virtual fixtures," *IEEE Trans. Robotics*, vol. 29, no. 3, pp. 674-683, June 2013.
18. R. A. MacLachlan, C. N. Riviere, "High-speed microscale optical tracking using digital frequency-domain multiplexing," *IEEE Trans. Instrumentation and Measurement*, vol. 58, no. 9, pp. 1991-2001, June 2009.

We claim:
1. A micromanipulation system, comprising:
    a micromanipulator, comprising:
        a handpiece;
        an actuator assembly coupled to the micromanipulator; and
        a tool vibrating system comprising a vibrator assembly and a vibration controller;
    a micromanipulation tool operatively connected to said handpiece, the micromanipulation tool comprising:
        a tool shaft comprising a connecting end for coupling the micromanipulation tool to the handpiece and a manipulation end;
        wherein the actuator assembly is further connected to said micromanipulation tool to provide manual control of said micromanipulation tool during use; and
    a force sensing system comprising a force sensor attached to said tool shaft of said micromanipulation tool, said force sensing system being configured to provide an output signal that indicates a force imposed on the manipulation end of said tool shaft, and indicate a force imposed along the tool shaft; and
    a processor in communication with said force sensing system,
    wherein said processor is configured to receive said output signal from said force sensing system and compensate for forces due to actuation of said micromanipulation tool to determine a force due to interaction of said micromanipulation tool with a region of interest,
    wherein the vibration controller is configured to communicate with said processor to receive an indication of at least one of a magnitude and a direction of said force due to interaction of said micromanipulation tool with a region of interest and to cause said vibration controller to impose a vibration to said tool shaft along said direction of said force due to interaction of said micromanipulation tool with a region of interest imposed on said tool shaft, wherein said vibration to said tool shaft facilitates a function of the manipulation end of the micromanipulation tool to manipulate an object; and
    wherein said processor is further configured to output the indication of at least one of a magnitude and a direction of said force due to interaction of said micromanipulation tool with a region of interest.
2. The micromanipulation system according to claim 1, wherein said force sensor takes the form of a fiber optic sensor.
3. The micromanipulation system according to claim 1, wherein said micromanipulator further comprises a tremor cancellation system comprising a motor within said handpiece, said motor being operatively attached to said micromanipulation tool to provide active cancellation of tremor on said micromanipulator during use independently of vibrations from said tool vibrating system.
4. The micromanipulation system according to claim 1, further comprising a position detection system configured to detect a position of said micromanipulator and transmit a signal to said processor indicating said detected position.

5. The micromanipulation system according to claim 4, wherein said micromanipulation tool is a microneedle, wherein said processor is configured to detect a puncture of said region of interest by said microneedle based on said signal indicating said detected position and said force due to interaction of said micromanipulator with said region of interest, and provide an indication of said puncture.

6. The micromanipulation system according to claim 5, wherein said indication of said puncture is a type of user feedback.

7. The micromanipulation system according to claim 5, wherein said micromanipulator further comprises a position holding system comprising a motor within said handpiece, said motor being operatively attached to said micromanipulation tool to maintain a position of said microneedle with respect to said puncture of said region of interest.

8. The micromanipulation system according to claim 7, wherein said position holding system is configured to receive said indication of said puncture from said processor and automatically maintain said position of said microneedle with respect to said puncture.

9. The micromanipulation system according to claim 7, wherein said actuator assembly comprises a motor operatively coupled to said tool shaft, wherein said motor changes a position of said tool shaft with respect to said handpiece to actuate said micromanipulation tool.

10. The micromanipulation system according to claim 1, wherein said actuator assembly is an electro-mechanical actuator assembly.

11. The micromanipulation system according to claim 1, wherein said actuator assembly comprises modular components for retrofitting micromanipulation tools.

12. The micromanipulation system according to claim 1, wherein said micromanipulation tool comprises a removable and replaceable component.

13. The micromanipulation system according to claim 1, wherein said micromanipulation tool is a surgical tool comprising one of a forceps, a needle, a pick, or a scalpel.

14. The micromanipulation system according to claim 1, wherein said micromanipulator is a manually operable smart tool.

15. The micromanipulation system according to claim 1, wherein said micromanipulator is adapted to be used with a cooperative control robotic system.

16. The micromanipulation system according to claim 1, wherein said micromanipulator is adapted to be used with a teleoperated robotic system.

17. A method of performing a micromanipulation, comprising:
    actuating a manual operation of a micromanipulation tool comprising a tool shaft, the tool shaft comprising a manipulation end to manipulate an object, wherein the micromanipulation tool is coupled to a micromanipulator;
    detecting a force imposed on the manipulation end of the tool shaft of said micromanipulation tool as a result of said manipulation;
    detecting a force imposed along the tool shaft of said micromanipulation tool as a result of said manipulation;
    determining a force due to interaction of said micromanipulation tool with said object based on the detected force imposed on the manipulation end of the tool shaft and the detected force imposed along the tool shaft and compensating for forces due to actuation of said micromanipulation tool;
    providing an indication of at least one of a magnitude and a direction of said force due to interaction of said micromanipulation tool with said object; and
    vibrating the tool shaft along the direction of the determined force due to interaction of said micromanipulation tool with said object,
    wherein said vibrating said tool shaft facilitates a function of the manipulation end of the micromanipulation tool to manipulate said object.

18. The method of performing a micromanipulation according to claim 17, further comprising: detecting a tremor on said micromanipulation tool; and
    cancelling said detected tremor using an automatic tremor cancellation system,
    wherein said cancelling said tremor is independent of said imposing said vibration to permit simultaneous tremor cancellation and vibrating of said micromanipulation tool.

19. The method of performing a micromanipulation according to claim 18, further comprising:
    wherein said actuating said manual operation of said micromanipulation tool comprising actuating using an electro-mechanical actuation system,
    wherein said actuating said manual operation of said micromanipulation tool is independent of said imposing said vibration and independent of said cancelling said tremor to permit simultaneous manual actuation, tremor cancellation and vibrating of said micromanipulation tool.

* * * * *